(12) United States Patent
Ii et al.

(10) Patent No.: US 11,369,412 B2
(45) Date of Patent: Jun. 28, 2022

(54) SENSOR INSERTION DEVICE AND BIOSENSOR

(71) Applicant: PHC Holdings Corporation, Tokyo (JP)

(72) Inventors: Yoshiteru Ii, Ehime (JP); Kenichi Hamanaka, Ehime (JP); Ryuji Shimizu, Ehime (JP); Akira Nishio, Ehime (JP); Takashi Endoh, Ehime (JP); Kazuaki Edagawa, Ehime (JP); Tetsuya Norikane, Ehime (JP); Junko Ikeda, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 913 days.

(21) Appl. No.: 16/094,329

(22) PCT Filed: Apr. 7, 2017

(86) PCT No.: PCT/JP2017/014565
§ 371 (c)(1),
(2) Date: Oct. 17, 2018

(87) PCT Pub. No.: WO2017/187943
PCT Pub. Date: Nov. 2, 2017

(65) Prior Publication Data
US 2019/0133638 A1      May 9, 2019

(30) Foreign Application Priority Data

Apr. 27, 2016   (JP) .............................. JP2016-089607
Apr. 27, 2016   (JP) .............................. JP2016-089608
(Continued)

(51) Int. Cl.
*A61B 5/1486*      (2006.01)
*A61B 5/145*       (2006.01)
(Continued)

(52) U.S. Cl.
CPC ........ *A61B 17/3468* (2013.01); *A61B 5/0004* (2013.01); *A61B 5/1473* (2013.01);
(Continued)

(58) Field of Classification Search
CPC ............ A61B 5/14532; A61B 5/14546; A61B 5/14865; A61B 5/15101; A61B 5/15107;
(Continued)

(56) References Cited

U.S. PATENT DOCUMENTS 4,442,836 A * 4/1984 Meinecke .......... A61B 5/15194
                                                 604/137
5,165,407 A    11/1992 Wilson et al.
(Continued)

FOREIGN PATENT DOCUMENTS

EP     2 327 984     6/2011
EP     2 329 770     6/2011
(Continued)

OTHER PUBLICATIONS

International Search Report dated Jul. 4, 2017 in International (PCT) Application No. PCT/JP2017/014565.
(Continued)

*Primary Examiner* — Eric F Winakur
*Assistant Examiner* — Alice Ling Zou
(74) *Attorney, Agent, or Firm* — Wenderoth, Lind & Ponack, L.L.P.

(57) ABSTRACT

A sensor insertion device comprises a main body, needle slider, disposal slider, spring, puncture knob, and opening mechanism (window member and handle). The needle slider grips a needle and a sensor on a first end side, and is slidable inside the main body. The disposal slider is slidable inside the main body. The puncture knob has an insertion hole into which the rear end portion of the needle slider can be inserted. The opening mechanism puts the insertion hole into
(Continued)

a closed state when the needle slider is being slid in the sensor insertion direction, and, puts the insertion hole in an open state in which the second end side of the needle slider has been inserted into the insertion hole by opening up the contact portion between the puncture knob and the second end side of the needle slider when the puncture operation is complete.

24 Claims, 47 Drawing Sheets

(30) Foreign Application Priority Data

| Apr. 27, 2016 | (JP) | JP2016-089609 |
|---|---|---|
| Apr. 27, 2016 | (JP) | JP2016-089610 |
| Apr. 27, 2016 | (JP) | JP2016-089611 |
| Apr. 27, 2016 | (JP) | JP2016-089663 |
| Apr. 27, 2016 | (JP) | JP2016-089664 |
| Apr. 27, 2016 | (JP) | JP2016-089665 |
| Apr. 27, 2016 | (JP) | JP2016-089666 |
| Apr. 27, 2016 | (JP) | JP2016-089667 |
| Apr. 27, 2016 | (JP) | JP2016-089712 |
| Apr. 27, 2016 | (JP) | JP2016-089713 |
| Apr. 27, 2016 | (JP) | JP2016-089714 |
| Apr. 27, 2016 | (JP) | JP2016-089715 |
| Apr. 27, 2016 | (JP) | JP2016-089716 |
| Apr. 28, 2016 | (JP) | JP2016-090460 |
| Apr. 28, 2016 | (JP) | JP2016-090544 |
| Apr. 28, 2016 | (JP) | JP2016-090579 |
| Jul. 6, 2016 | (JP) | JP2016-133985 |
| Jul. 6, 2016 | (JP) | JP2016-134002 |

(51) Int. Cl.
    *A61B 17/34*     (2006.01)
    *A61B 5/1473*     (2006.01)
    *A61B 5/00*     (2006.01)
    *G01N 27/327*     (2006.01)

(52) U.S. Cl.
    CPC ........ *A61B 5/1486* (2013.01); *A61B 5/14532* (2013.01); *A61B 5/14865* (2013.01); *A61B 5/6849* (2013.01); *A61B 17/3496* (2013.01); *G01N 27/3272* (2013.01); *A61B 2560/063* (2013.01)

(58) Field of Classification Search
    CPC .............. A61B 5/15113; A61B 5/1513; A61B 5/15142–15144; A61B 5/15186–15194; A61B 2560/063; A61B 5/1451; A61B 5/1459; A61B 5/1473–14735; A61B 5/15105; A61B 5/6849; A61B 17/3468; A61M 5/14248–2005/14256; A61M 2005/14284; A61M 2005/1585; A61M 2005/14252; A61M 2005/1583; A61M 5/3287

See application file for complete search history.

(56) References Cited

U.S. PATENT DOCUMENTS

| 6,197,040 | B1 | 3/2001 | LeVaughn et al. |
|---|---|---|---|
| 6,293,925 | B1 | 9/2001 | Safabash et al. |
| 2003/0088166 | A1 | 5/2003 | Say et al. |
| 2004/0133164 | A1 | 7/2004 | Funderburk et al. |
| 2004/0180391 | A1 | 9/2004 | Gratzl et al. |
| 2006/0036187 | A1 | 2/2006 | Vos et al. |
| 2006/0118415 | A1 | 6/2006 | Say et al. |
| 2008/0248514 | A1 | 10/2008 | Inamori et al. |
| 2009/0000947 | A1 | 1/2009 | Akahori et al. |
| 2009/0299301 | A1 | 12/2009 | Gottlieb et al. |
| 2010/0204554 | A1 | 8/2010 | Say et al. |
| 2010/0228149 | A1 | 9/2010 | Fujimura et al. |
| 2010/0305422 | A1 | 12/2010 | Say et al. |
| 2012/0303043 | A1 | 11/2012 | Donnay |
| 2013/0150691 | A1 | 6/2013 | Pace et al. |
| 2013/0274574 | A1 | 10/2013 | Say et al. |
| 2014/0124384 | A1 | 5/2014 | Gerber et al. |
| 2014/0221801 | A1 | 8/2014 | Say et al. |
| 2015/0051457 | A1* | 2/2015 | Matsumoto ........ A61B 5/14503 702/183 |
| 2015/0190076 | A1* | 7/2015 | Ohkoshi ............. A61B 5/6849 600/309 |
| 2017/0042457 | A1 | 2/2017 | Pace et al. |
| 2017/0188912 | A1* | 7/2017 | Halac ................... A61B 5/6849 |
| 2017/0202491 | A1 | 7/2017 | Heller et al. |
| 2017/0265791 | A1 | 9/2017 | Pace et al. |
| 2017/0290533 | A1* | 10/2017 | Antonio .............. A61B 5/0022 |

FOREIGN PATENT DOCUMENTS

| EP | 2 329 771 | 6/2011 |
|---|---|---|
| EP | 2 332 466 | 6/2011 |
| EP | 2 335 581 | 6/2011 |
| EP | 2 335 582 | 6/2011 |
| EP | 2 335 583 | 6/2011 |
| EP | 2 335 584 | 6/2011 |
| EP | 2 335 585 | 6/2011 |
| EP | 2 335 586 | 6/2011 |
| EP | 2 335 587 | 6/2011 |
| EP | 3 001 952 | 4/2016 |
| EP | 3 111 832 | 1/2017 |
| JP | 5-506172 | 9/1993 |
| JP | 07-155310 | 6/1995 |
| JP | 2000-262498 | 9/2000 |
| JP | 2002-65646 | 3/2002 |
| JP | 2003-190122 | 7/2003 |
| JP | 2003-527138 | 9/2003 |
| JP | 2004-033438 | 2/2004 |
| JP | 2006-15147 | 1/2006 |
| JP | 2011-13072 | 1/2011 |
| JP | 2013-121521 | 6/2013 |
| JP | 5306521 | 7/2013 |
| JP | 2015-509011 | 3/2015 |
| JP | 2015-186625 | 10/2015 |
| WO | 2002/054953 | 7/2002 |
| WO | 2008/102639 | 8/2008 |
| WO | 2013/035455 | 3/2013 |

OTHER PUBLICATIONS

Extended European Search Report dated Feb. 26, 2019 in European Patent Application 17789230.4.

Office Action dated Oct. 27, 2020 in corresponding Japanese Patent Application No. 2019-212939 with English-language translation.

Extended European Search Report dated Jun. 2, 2020 in corresponding European Patent Application No. 20166404.2.

* cited by examiner

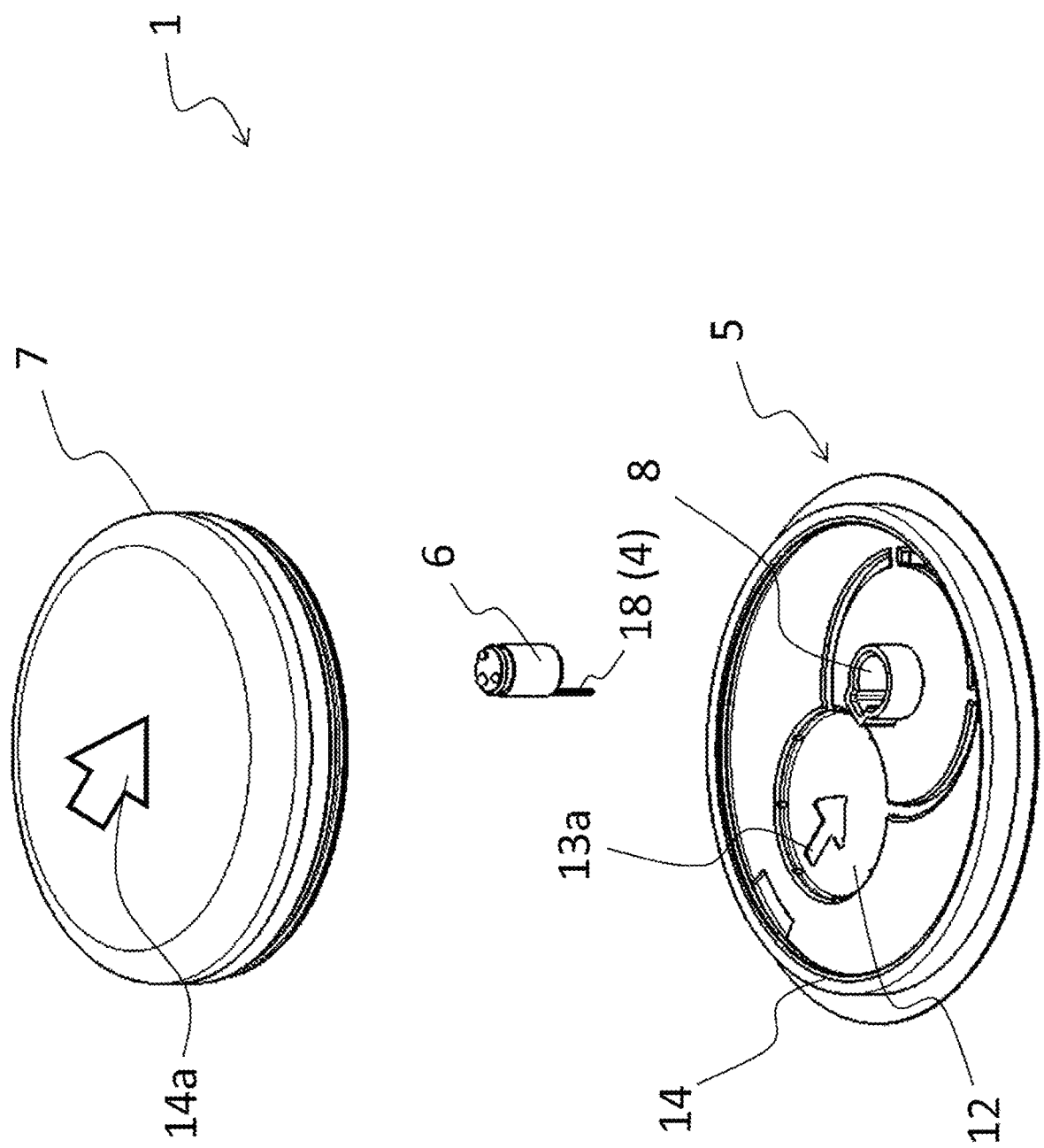

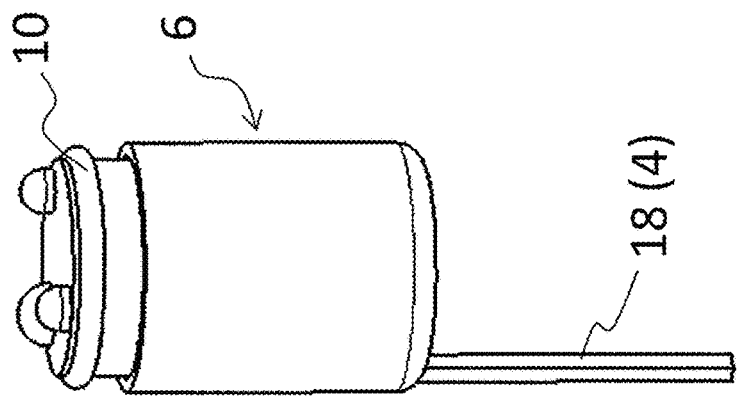
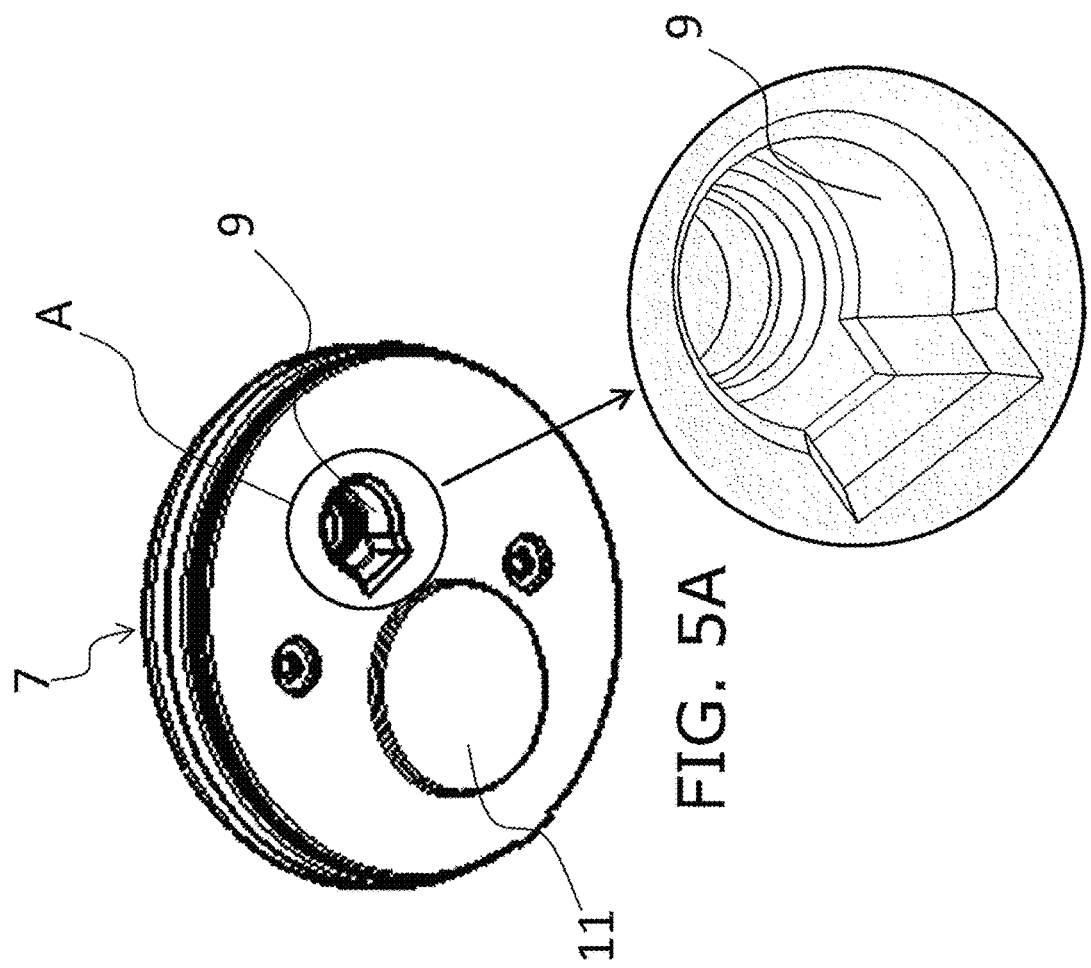

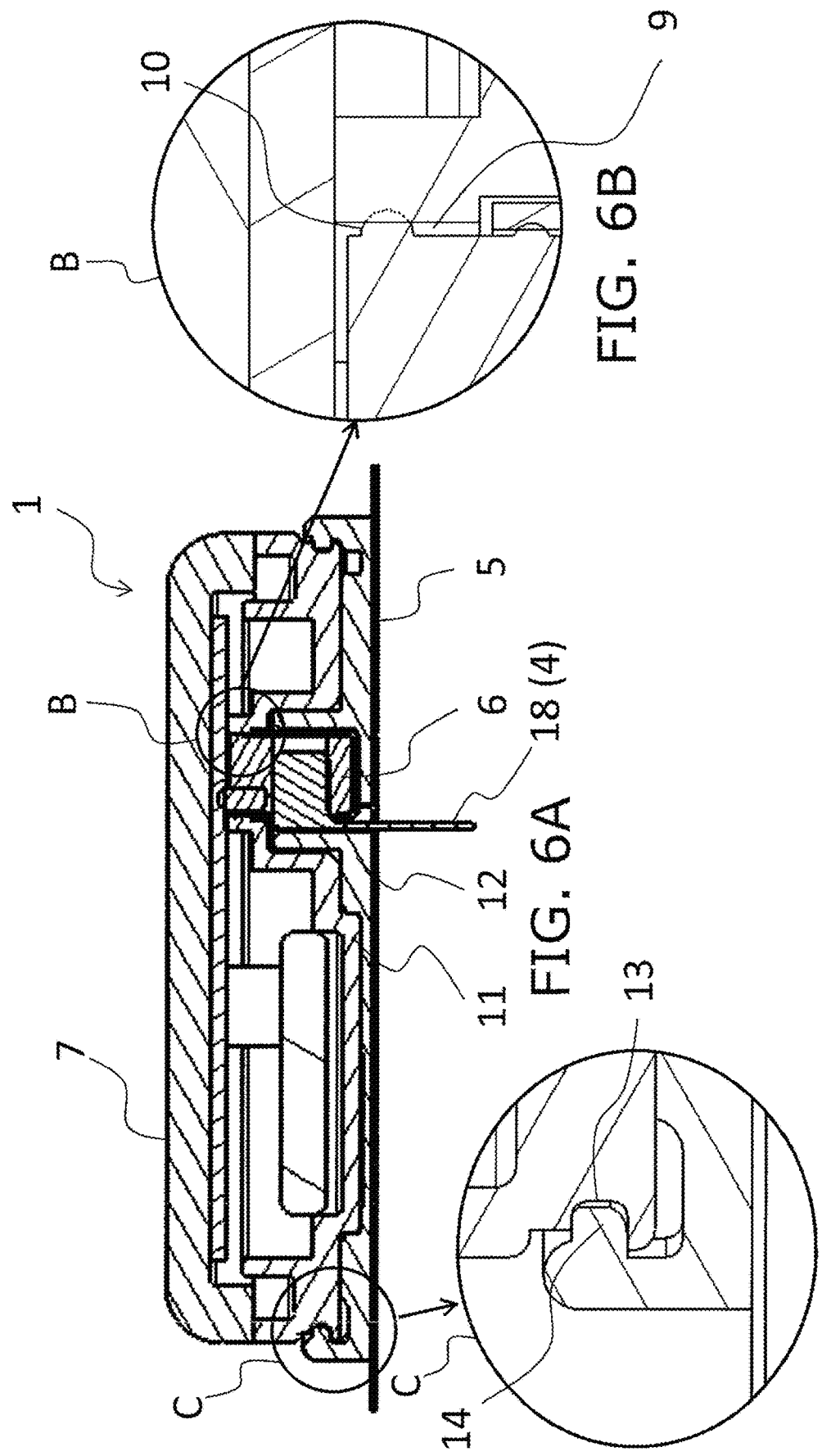

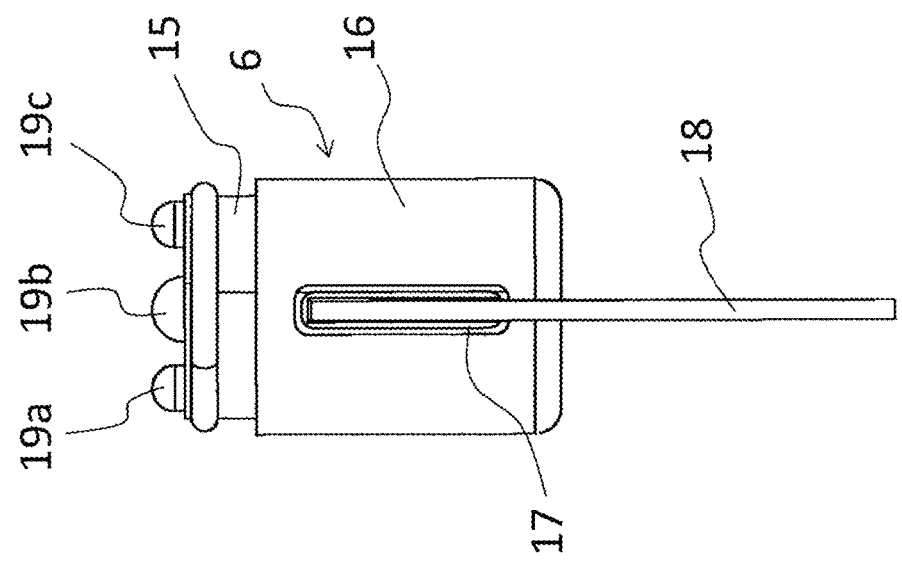
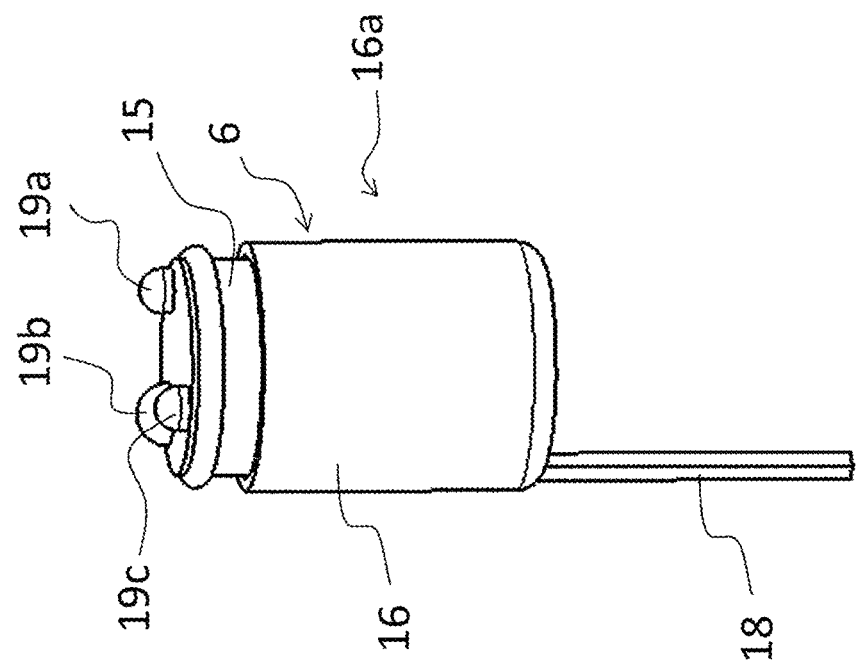
FIG. 7A
FIG. 7B

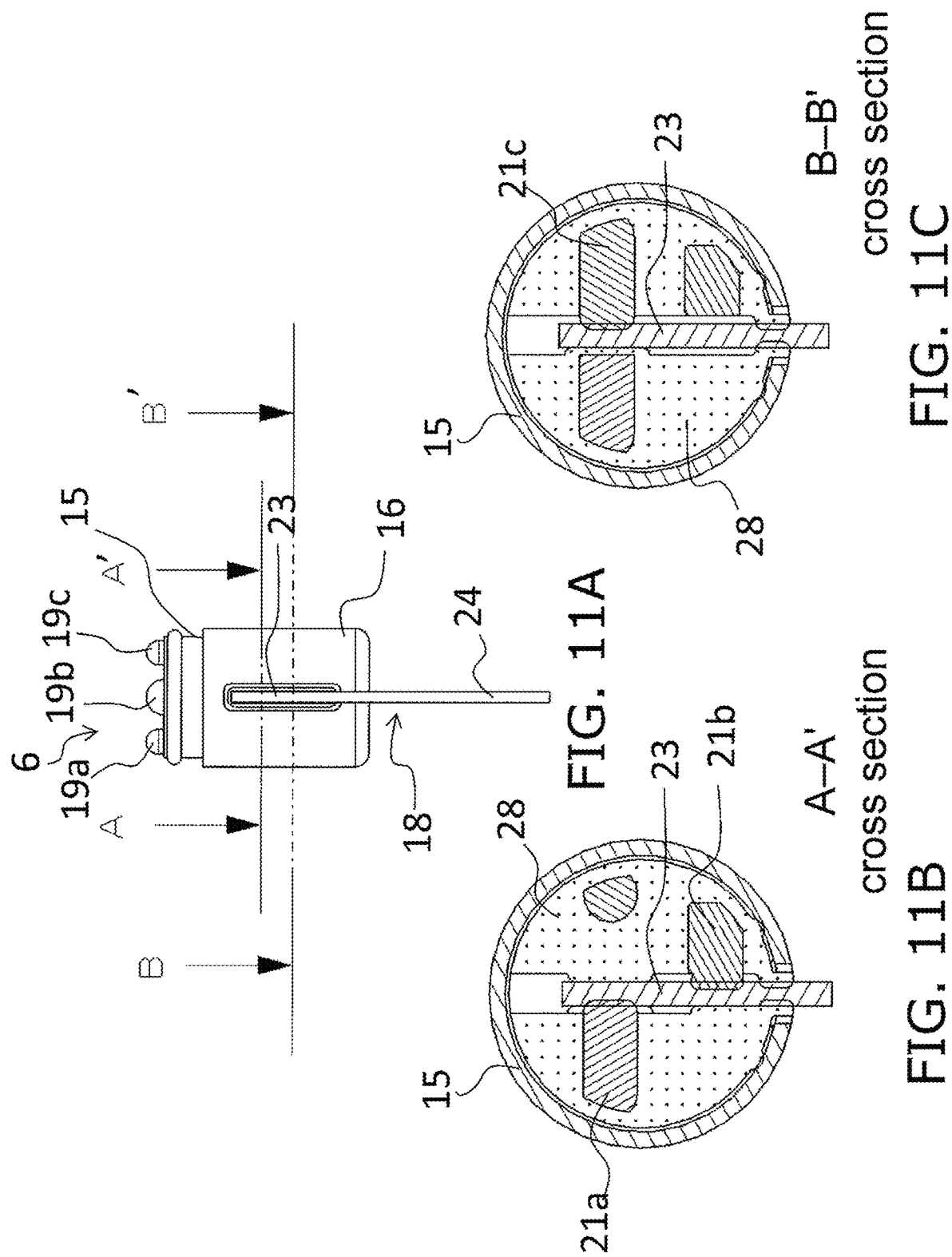

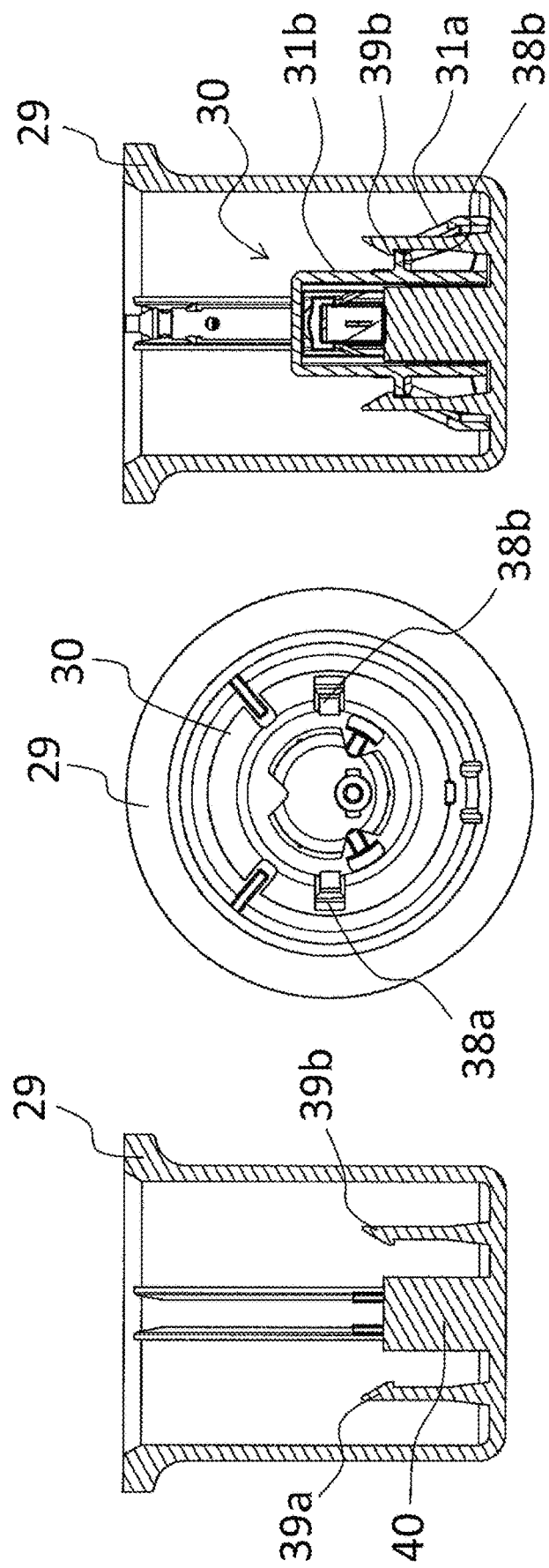

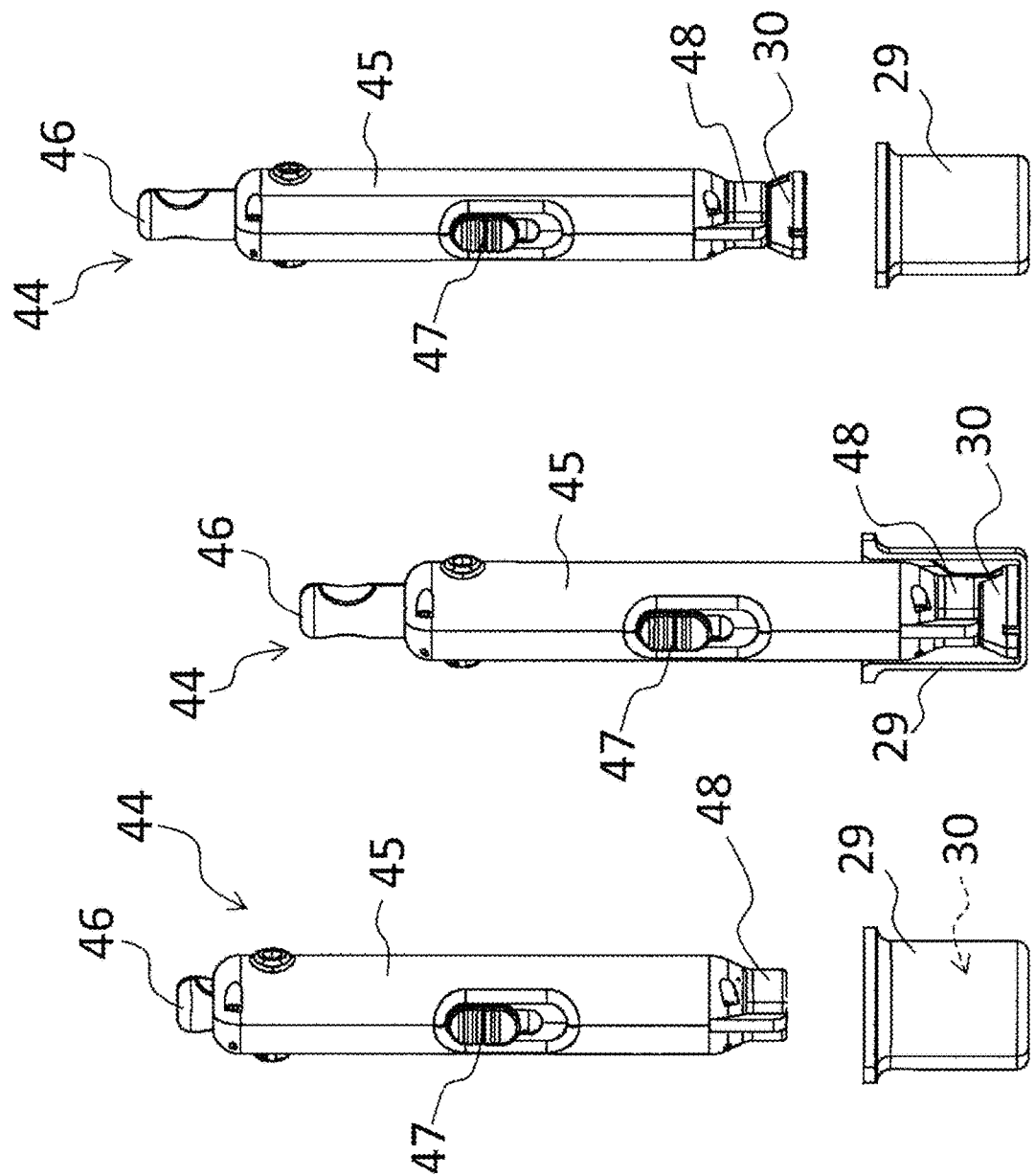

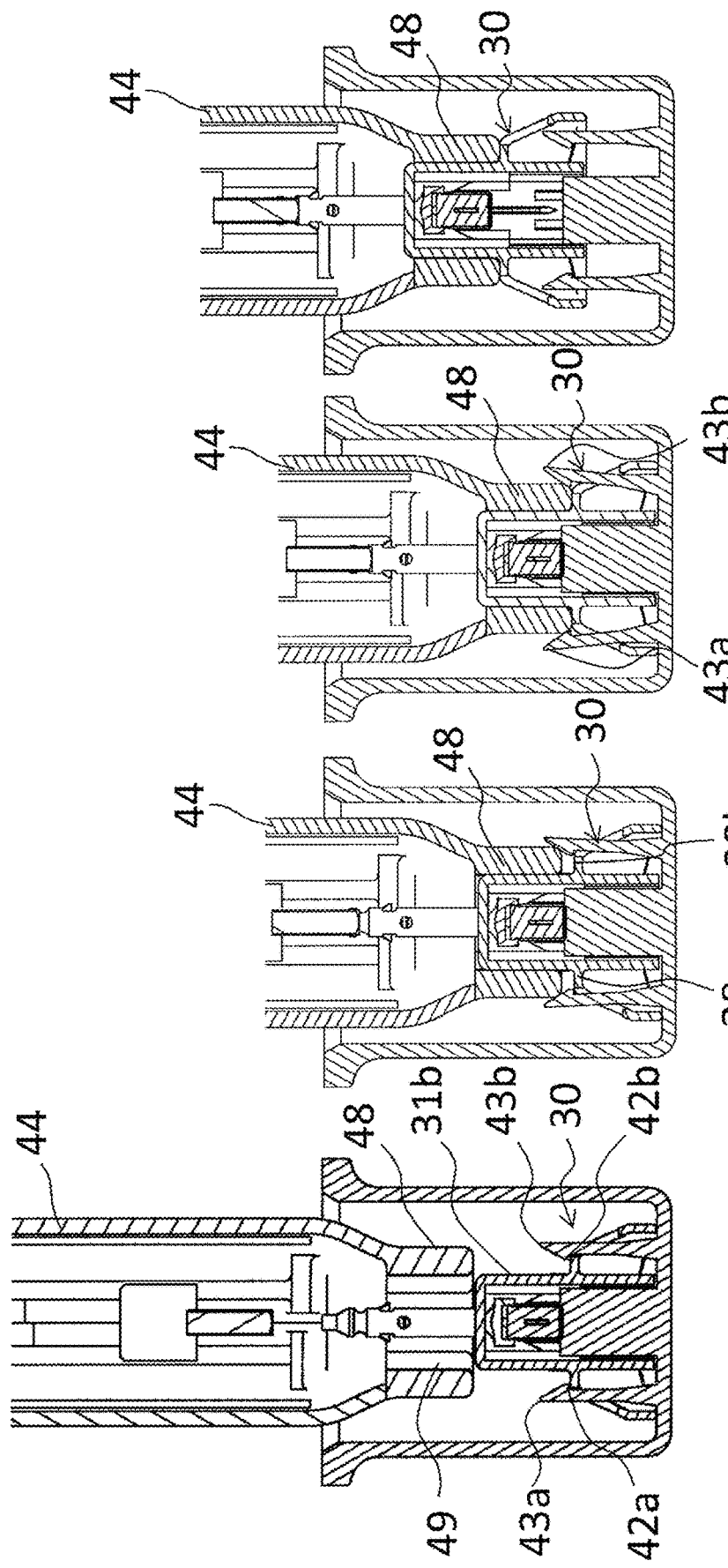

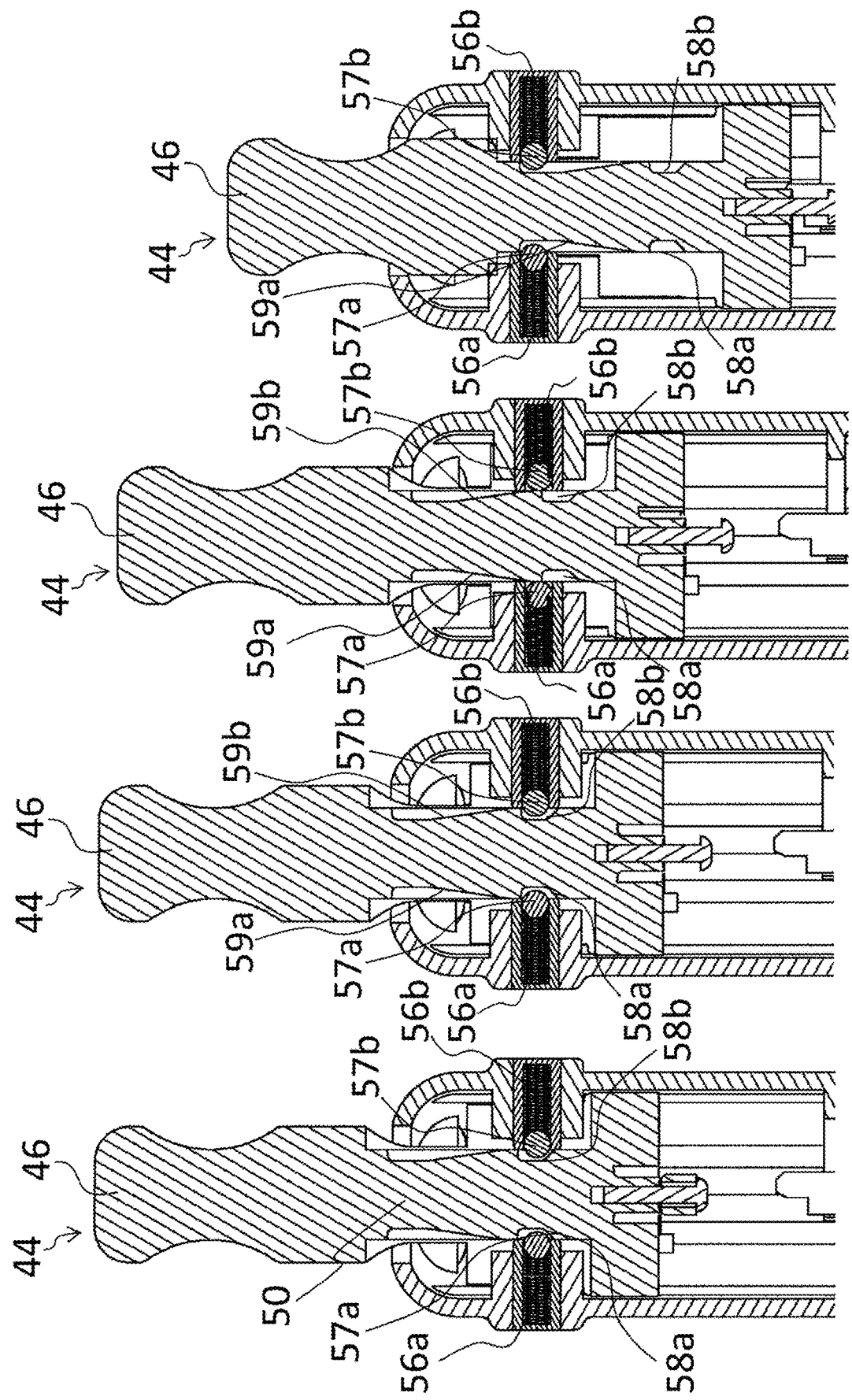

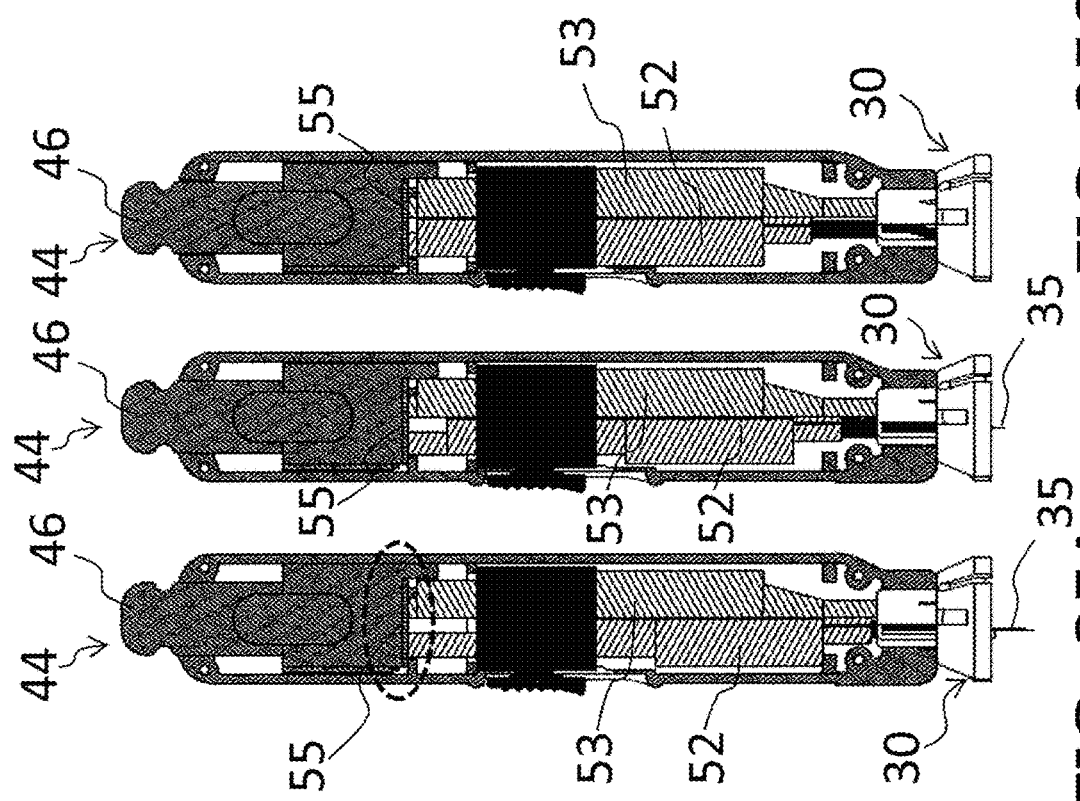

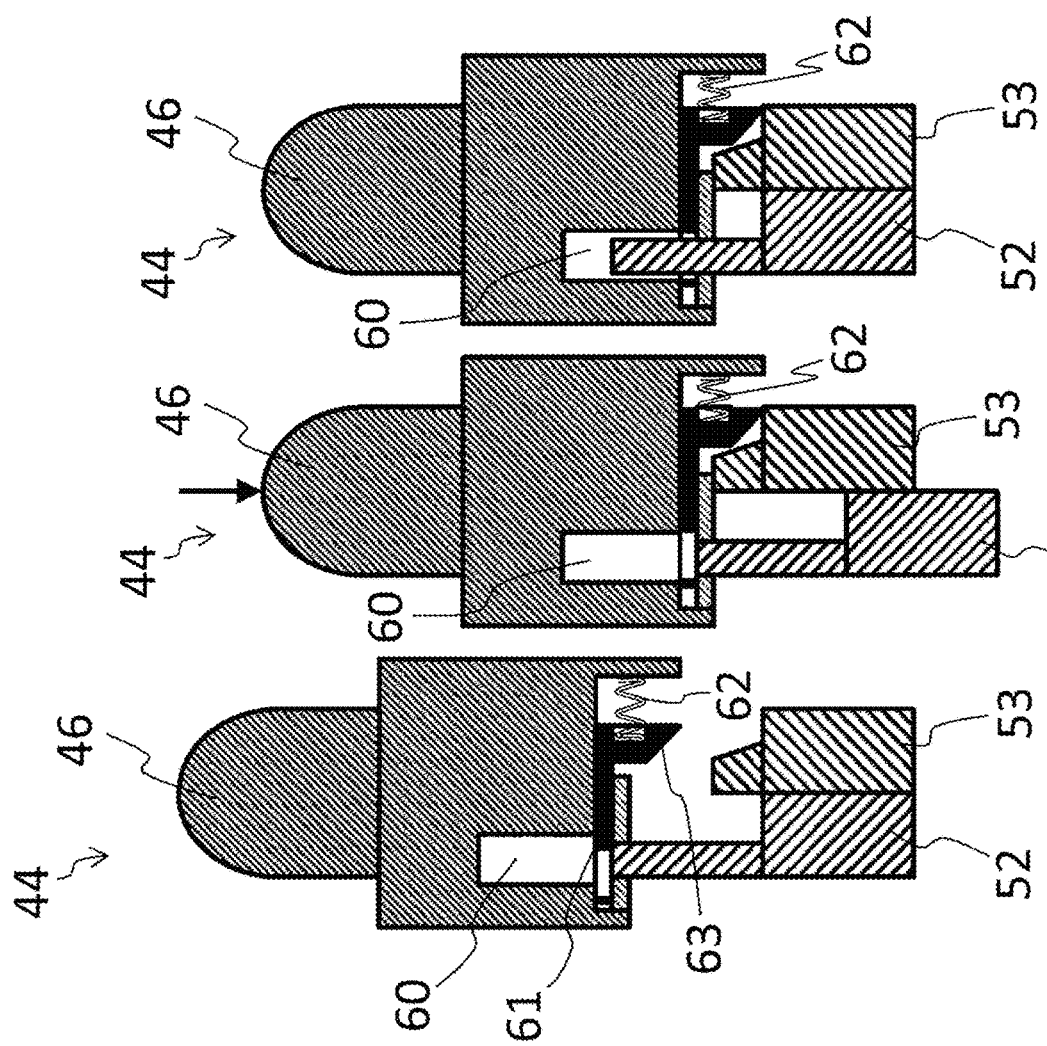

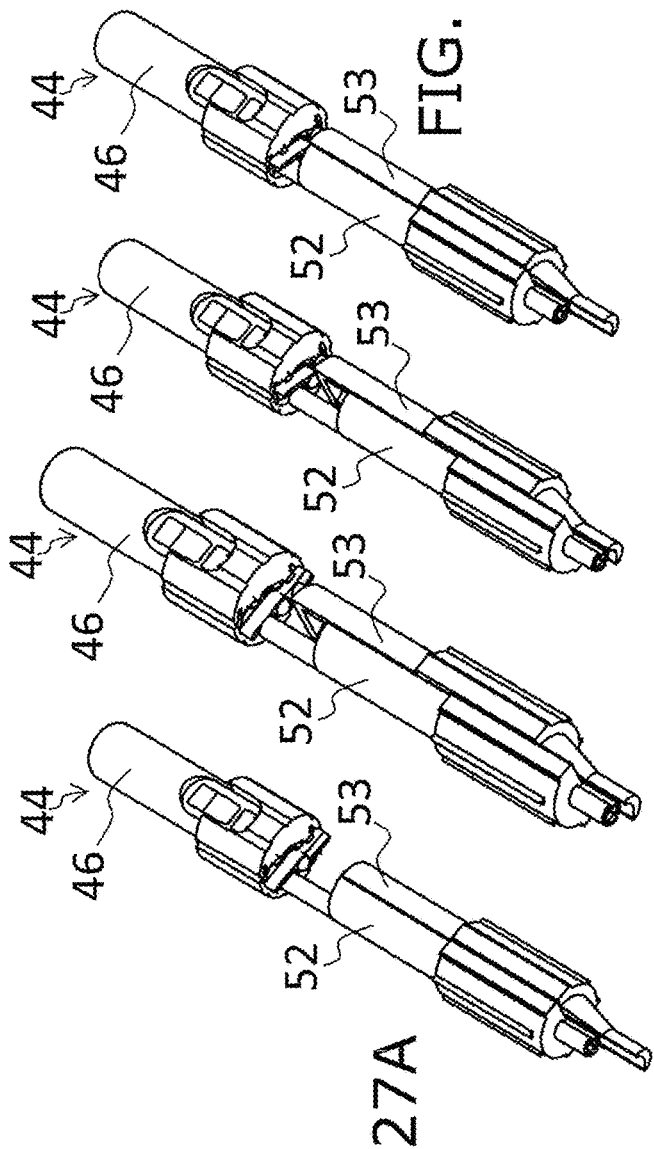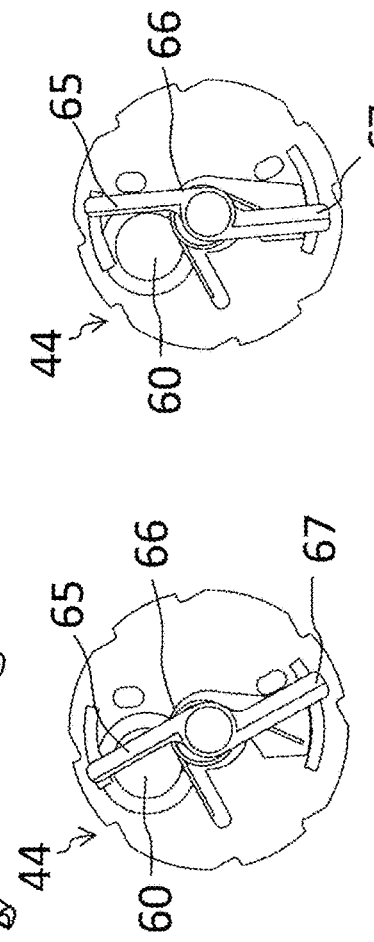

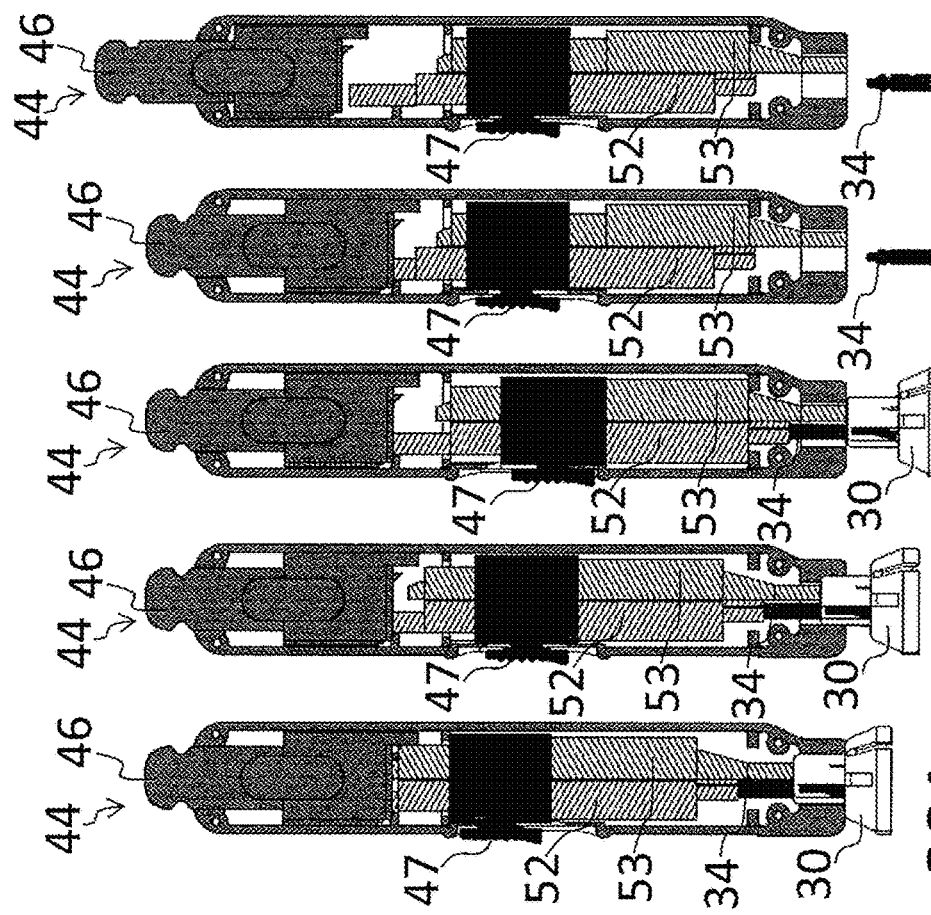

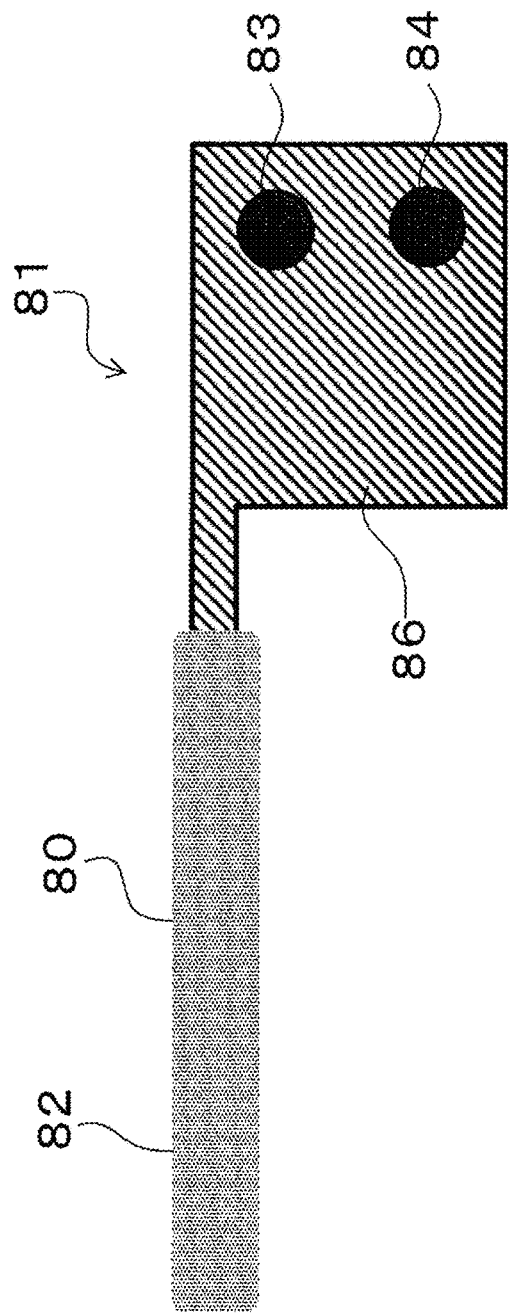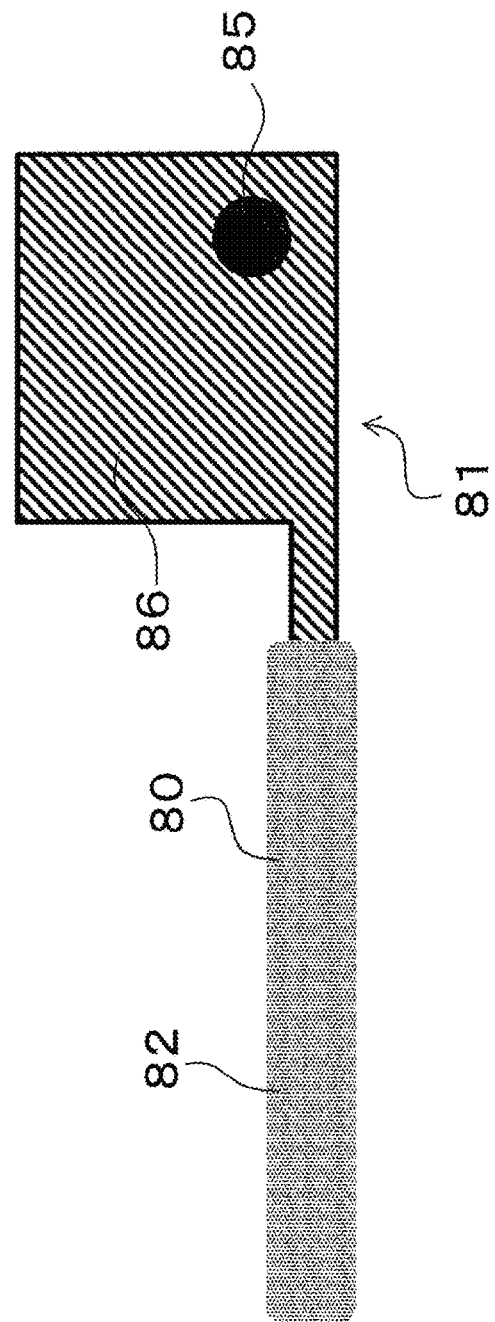
FIG. 36A
FIG. 36B

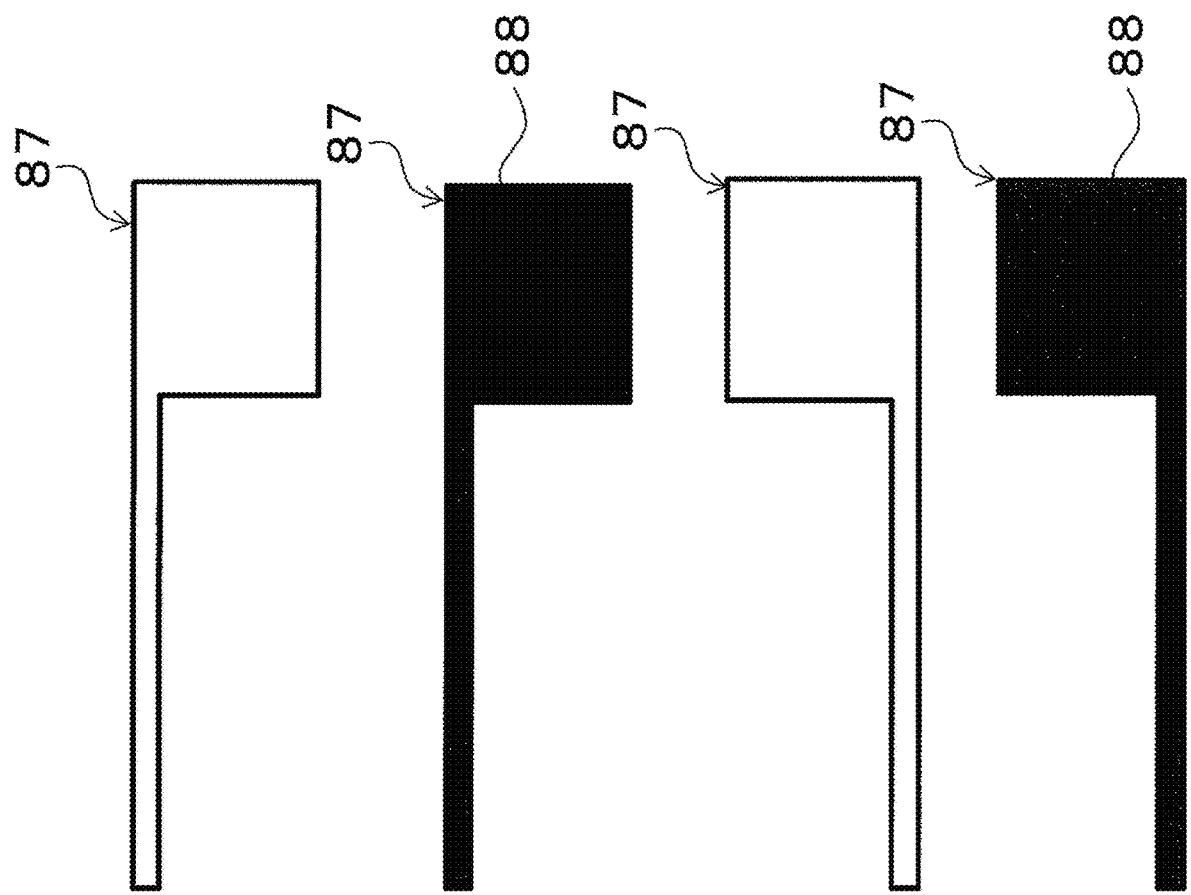

SENSOR INSERTION DEVICE AND BIOSENSOR

TECHNICAL FIELD

The present invention relates to a device that inserts a biosensor for measuring the concentration of sugars, amino acids, or the like in a living body under the skin of a patient, and to a biosensor that measures the concentration of sugars, amino acids, or the like contained in a bodily fluid in a living body.

BACKGROUND

The sensor insertion device of a conventional biosensor is configured to hold a packaged sensor supply unit including a sensor unit (a sensor main body and its support components), a needle unit (a needle and its support components), and a transmitter, wherein a sensor is inserted together with a needle into a patient's body, and just the needle is withdrawn, leaving the sensor inside (see, for example, Patent Literature 1 and 2).

Also, a conventional biosensor is configured to comprise a substrate, an electrode layer formed on the substrate, a mediator layer formed on the electrode layer, an enzyme layer formed on the mediator layer, an enzyme layer formed on the mediator layer, and a protective film formed on the enzyme layer (see, for example, Patent Literature 3).

CITATION LIST

Patent Literature

Patent Literature 1: Published Japanese Translation of PCT International Application No. 2015-509011
Patent Literature 2: Japanese Patent No. 5306521
Patent Literature 3: Japanese Laid-Open Patent Application No. 2015-186625

SUMMARY

Technical Problem

The problem with the sensor insertion device of the above-mentioned conventional biosensor is that after the sensor is inserted, the sensor insertion device is not reused, and is discarded instead. When a sensor insertion device is reused, even when the sensor insertion device is made to perform a sensor insertion operation again in a state in which only the needle has been pulled out, there is a need for safety measures so that a puncture operation with the needle will not be performed in a state in which there is no sensor.

It is therefore an object of the present invention to improve convenience by prohibiting an operation in which a sensor supply unit that has been used is accidentally reused in the course of reusing a sensor insertion device.

Solution to Problem

To achieve this object, the sensor insertion device of the present invention in one that inserts a sensor into a patient's body by using a needle that punctures the skin on a first end side, the sensor insertion device comprising a main body case, a needle slider, a disposal slider, a biasing member, a puncture knob, and an opening mechanism. The needle slider is provided inside the main body case in a state of being able to slide in the insertion direction of the sensor while gripping the needle and the sensor on the first end side. The disposal slider is provided inside the main body case in a state of being able to slide in parallel with the needle slider. The biasing member is provided between the needle slider and the disposal slider and biases the needle slider, which has moved in the sensor insertion direction, in the opposite direction from the sensor insertion direction. The puncture knob pushes in the needle slider to a specific puncture position by sliding it in the sensor insertion direction in a state of being in contact with a second end side of the needle slider that is on the opposite side from the first end, and has an insertion hole into which the rear end portion of the needle slider can be inserted. The opening mechanism puts the insertion hole in a closed state when the needle slider is slid a specific length in the sensor insertion direction, and puts the insertion hole in an open state in which the second end side of the needle slider has been inserted into the insertion hole by opening up the contact portion between the puncture knob and the second end side of the needle slider when the puncture operation is complete.

Another problem with the above-mentioned conventional biosensor is that measurement sensitivity is low.

For example, there is a type of blood glucose level sensor (such as CGM: continuous glucose monitoring type) that monitors glucose in the interstitial fluid, but since the glucose concentration in the interstitial fluid is lower than the concentration in the blood, measurement sensitivity needs to be improved.

In the course of diligent investigation into the cause of this low measurement sensitivity, the inventors of the present invention discovered that there is an important factor in the enzyme layer.

The biosensor of the present invention is intended to increase measurement sensitivity.

To achieve this object, the biosensor of the present invention comprises a substrate, an electrode layer that is formed on the substrate, a mediator layer that is formed on the electrode layer, an enzyme layer that is formed on the mediator layer, and a protective film that is formed on the enzyme layer, wherein the enzyme layer is configured to contain sodium polyacrylate, thereby achieving the stated object.

Advantageous Effects

With the sensor insertion device of the present invention, when a sensor insertion device is reused, an operation in which the a sensor supply unit that has already been used is accidentally reused is prohibited, and this makes the device more convenient to use.

Also, with the biosensor of the present invention, measurement sensitivity can be increased.

BRIEF DESCRIPTION OF DRAWINGS

FIG. 4 is an exploded oblique view of the main part of the continuous glucose monitoring (CGM) device in FIG. 1;

FIG. 5A is a bottom view of the main part of the continuous glucose monitoring (CGM) device in FIG. 1, FIG. 5B is a detail view thereof, and FIG. 5C is an oblique view of the main part;

FIG. 6A is a cross section of the main part of the continuous glucose monitoring (CGM) device in FIG. 1, FIG. 6B is a detail view thereof, and FIG. 6C is a detail view thereof;

FIG. 7A is an oblique view of the main part of the continuous glucose monitoring (CGM) device in FIG. 1, and FIG. 7B is a side view thereof;

FIG. 11A is a side view of the main part of the continuous glucose monitoring (CGM) device in FIG. 1, FIG. 11B is a cross section thereof, and FIG. 11C is a cross section thereof;

FIG. 16A is a cross section of the main part of the continuous glucose monitoring (CGM) device in FIG. 1, FIG. 16B is a top view thereof, and FIG. 16C is a cross section thereof;

FIG. 18A is an oblique view of the main part of the continuous glucose monitoring (CGM) device in FIG. 1, FIG. 18B is an oblique view thereof, and FIG. 18C is an oblique view thereof:

FIG. 19A is a cross section of the main part of the continuous glucose monitoring (CGM) device in FIG. 1. FIG. 19B is a cross section thereof, FIG. 19C is a cross section thereof, and FIG. 19D is a cross section thereof;

FIG. 24A is a cross section of the main part of the continuous glucose monitoring (CGM) device in FIG. 1: FIG. 24B is a cross section thereof. FIG. 24C is a cross section thereof, and FIG. 24D is a cross section thereof:

FIG. 25A is a cross section of the main part of the continuous glucose monitoring (CGM) device in FIG. 1, FIG. 25B is a cross section thereof, and FIG. 25C is a cross section thereof;

FIG. 26A is a cross section of the main part of the continuous glucose monitoring (CGM) device in FIG. 1, FIG. 26B is a cross section thereof, and FIG. 26C is a cross section thereof;

FIG. 27A is an exploded oblique view of the main part of the continuous glucose monitoring (CGM) device in FIG. 1, FIG. 27B is an exploded oblique view thereof, FIG. 27C is an exploded oblique view thereof, FIG. 27D is an exploded oblique view thereof, FIG. 27E is a top view showing a state in which the insertion hole has been closed by the opening mechanism, and FIG. 27F is a top view showing a state in which the insertion hole has been opened by the opening mechanism;

FIG. 28A is a cross section of the main part of the continuous glucose monitoring (CGM) device in FIG. 1, FIG. 28B is a cross section thereof, FIG. 28C is a cross section thereof, FIG. 28D is a cross section thereof, and FIG. 28E is a cross section thereof;

FIG. 36A is a top view of a sensor main body pertaining to another embodiment of the present invention, and FIG. 36B is a bottom view thereof:

FIG. 37 is a diagram of the steps for manufacturing the sensor main body in FIG. 36A;

DESCRIPTION OF EMBODIMENTS

Embodiment 1

Configuration of Continuous Glucose Monitoring (CGM) Device

An embodiment of the present invention applied to a glucose sensor for monitoring glucose will now be given as an example of this continuous glucose monitoring (CGM) system, with reference to the attached drawings.

A continuous glucose monitoring (CGM) system continuously monitors the blood glucose level in diabetic patients.

In the following description. "front" means the puncture side in the puncture direction in which the patient's skin is punctured (the side on which the needle 35 protrudes), and "rear" means the opposite side from the puncture side (the puncture knob 46 side). These directions "front" and "rear" respectively correspond to "front" and "rear" in the insertion direction of the sensor 4, which will be described below. The "first end side" (discussed below) refers to the front side in the above-mentioned puncture direction, and the "second end side" refers to the rear side in the puncture direction. The "sensor insertion direction" (discussed below) coincides with the "puncture direction."

Overview of Sensor Attachment Device

Figure 1:
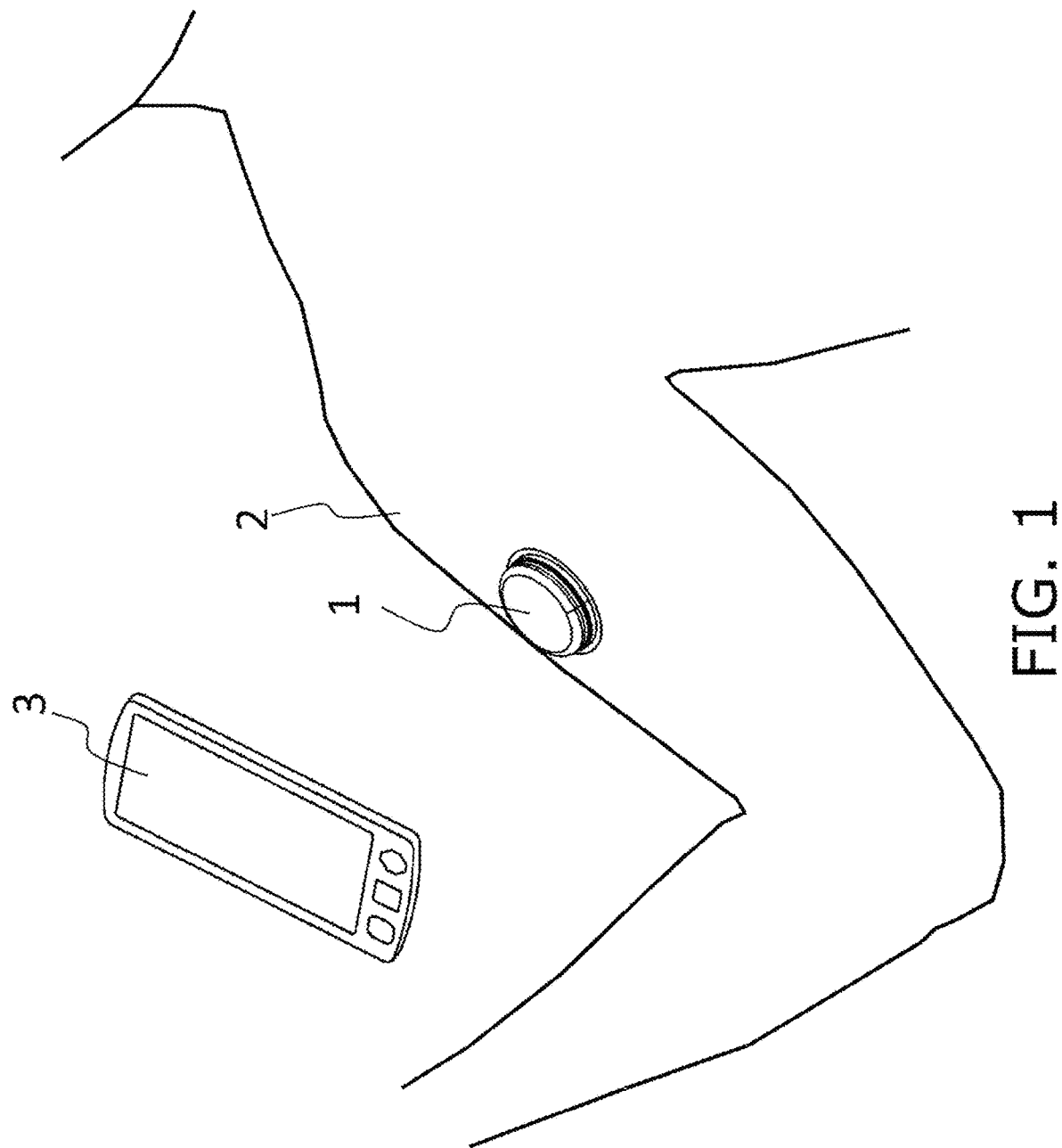
FIG. 1 illustrates the use of a continuous glucose monitoring (CGM) device in an embodiment of the present invention.

FIG. 1 shows a sensor attachment device 1 of the continuous glucose monitoring (CGM) system in this embodiment.

In the sensor attachment device 1 of the continuous glucose monitoring (CGM) system, a sensor 4 (see FIG. 3) is left under the skin of an upper arm 2 of a diabetic patient, and the glucose concentration in the subcutaneous tissue interstitial fluid is continuously measured. The sensor attachment device 1 in this embodiment is configured to convert the glucose concentration into an electrical current value, and transmit the calculated value. With the sensor attachment device 1, the current value is measured once every minute, for example, the arithmetic mean for a specific number of times is calculated, and that value is recorded in a memory. Then, the value obtained by calculating the arithmetic mean of the values for five samples acquired once every minute, for example, is stored in the memory to record the value of the glucose concentration at five-minute intervals.

Figure 2:
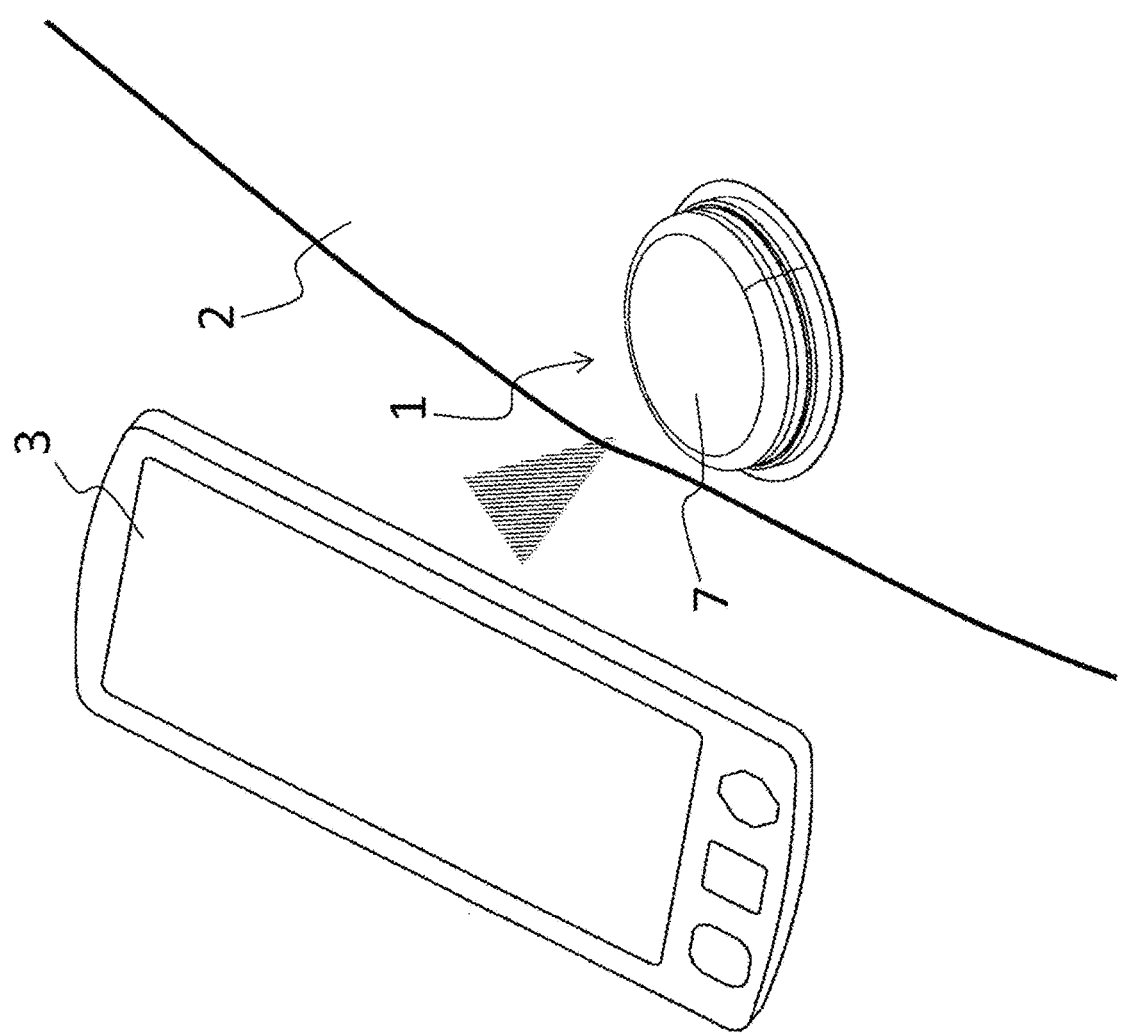
FIG. 2 illustrates the use of the continuous glucose monitoring (CGM) device in FIG. 1.

FIGS. 1 and 2 show the sensor attachment device 1 and a measurement device 3.

As shown in FIG. 2, the sensor attachment device 1 is configured to be capable of sending and receiving signals wirelessly to and from the measurement device 3 by means of a substantially circular transmitter 7.

With the sensor attachment device 1, the transmitter 7 stores the current value from the sensor in the memory, and wirelessly transmits the value stored in the memory to the measurement device 3. The value to be transmitted may be the current value, or may be a value after conversion into glucose concentration. The measurement device 3 calculates the glucose concentration from the value that is read, displays the result along with time information, and stores the time information and the glucose concentration in the memory inside the measurement device 3.

Fluctuations in the blood glucose level of a diabetic patient over the course of 24 hours can be ascertained by continuing this measurement of the blood glucose level for anywhere from 3 to 14 days. This makes possible more appropriate treatment that is suited to the symptoms of each diabetic patient.

Furthermore, this information about fluctuation of the blood glucose level can be used to calculate the amount of insulin to be administered to the patient and the timing thereof. In a state of being wirelessly connected to the sensor attachment device 1 (and/or the measurement device 3), an insulin pump administers the proper amount of insulin while monitoring the patient's glucose level in real time. The result is that this functions as an artificial pancreas, which makes it possible to maintain blood glucose at the ideal level.

Figure 3:
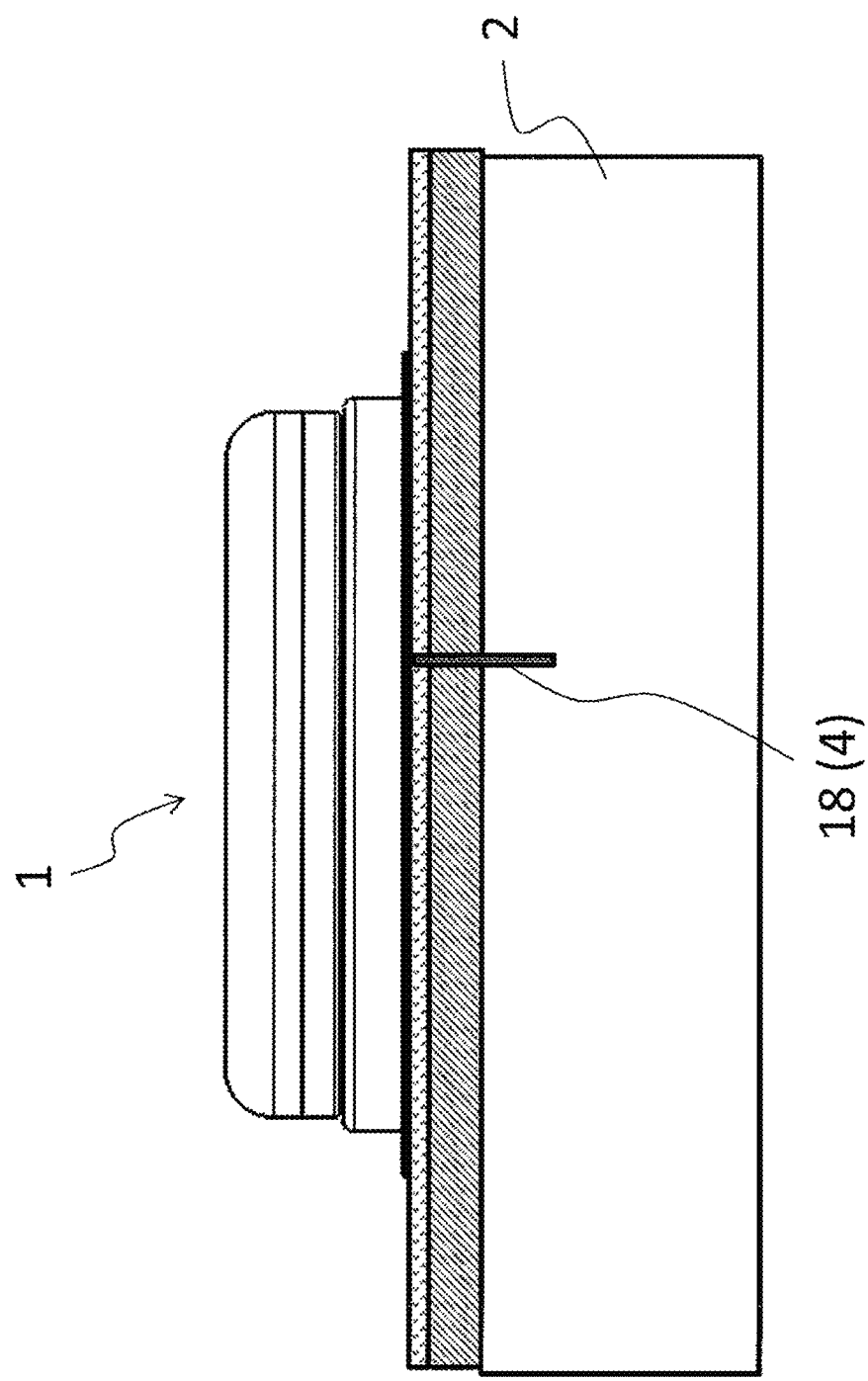
FIG. 3 illustrates the use of the continuous glucose monitoring (CGM) device in FIG. 1.

FIG. 3 is a cross section of a portion of the upper arm 2 of a diabetic patient who is wearing the sensor attachment device 1. The sensor 4 protrudes below the sensor attachment device 1. In a state in which the sensor 4 is being worn, the sensor 4 is left under the skin.

A sensor main body 18 of the sensor 4 is about 1 cm in length and has a needle- or rod-shaped distal end in order to facilitate insertion under the skin of a diabetic patient. The distal end portion of the sensor 4 is covered with a reaction layer, which is made up of a protective film that transmits and absorbs glucose (test substance) and reacts this glucose with an enzyme to produce a measurement substance, as well as with an enzyme layer, a mediator layer, etc. An electrode for electrochemically measuring glucose is provided below the reaction layer. This distal end portion is stuck under the skin and left in the interstitial fluid, which allows the concentration of glucose in the interstitial fluid of the subcutaneous tissue to be observed (and/or measured/detected).

With this subcutaneous indwelling glucose sensor that measures glucose in subcutaneous tissue, there may be a time lag between the blood glucose level and the measurement result. It may therefore be necessary to perform correction using measured values from an SMBG (self-monitoring of blood glucose) type of glucose sensor.

Configuration of Sensor Attachment Device

FIG. 4 is an exploded oblique view of the sensor attachment device 1.

The sensor attachment device 1 comprises a base unit 5, a sensor unit 6, and a transmitter 7.

Configuration of Base Unit

The base unit 5 is a wearable unit that is worn on the patient's body. The sensor unit 6 includes a sensor main body that is left in the patient's body. The transmitter 7 has a function of calculating biological information from a signal inputted from the sensor unit 6, storing this information, and transmitting it to the measurement device 3. The sensor attachment device 1 is configured so that the base unit 5, the sensor unit 6, and the transmitter 7 can be detached, and is a device for that allows the sensor 4 to be worn on the patient's body.

In the base unit 5, the main body has a substantially circular shape. An adhesive (or a pressure-sensitive adhesive tape) that can be attached to the patient's body is applied to the outer bottom surface of the base unit 5, which is the surface that is attached to the patient, in order to be affixed at the attachment site of the patient's body. The base unit 5 is provided with a through-hole 8 in which the sensor unit 6 is inserted. The sensor unit 6 is then inserted into the through-hole 8. The through-hole 8 is provided at a position away from the center of the circle of the substantially circular transmitter 7.

A convex part 14 serving as a mating portion for gripping the transmitter 7 is provided to the peripheral edge of the main body of the base unit 5 in order to fix the substantially circular transmitter 7.

The base unit 5 is made of a flexible material such as elastomer resin, for example. This makes it easier to attach base unit 5 to the patient's body and allows the sensor unit 6 and the transmitter 7 to be easily gripped.

Connection Configuration of Transmitter and Sensor Unit

FIGS. 5A to 5C show the connection mechanism for the transmitter 7 and the sensor unit 6.

FIG. 5A is a bottom view of the transmitter 7. The part labeled A is the lower face portion of a mounting hole 9, and FIG. 5B is a detail view thereof. FIG. 5C is an oblique view of the sensor unit 6.

The mounting hole 9 is provided at a position away from the center of the circle of the substantially circular transmitter 7. A convex part 10 provided around the circumferential edge of the head of the sensor unit 6 so as to mate with the mounting hole 9. Since the convex part 10 of the sensor unit 6 is made of a flexible material such as elastomer resin or silicone rubber, it has high stretchability. Therefore, in a state in which the convex part 10 of the sensor unit 6 is mated with the mounting hole 9, the inner wall of the mounting hole 9 and the convex part 10 of the sensor unit 6 are snugly mated. As a result, moisture such as perspiration from the patient can be prevented from entering the inside of the transmitter 7 from the bottom face of the base unit 5.

The mounting hole 9 is provided at a position away from the center of the lower face of the substantially circular transmitter 7. A mating component 11 of the convex base unit 5 is provided at a position away from the center of the lower face of the substantially circular transmitter 7.

Let us return to FIG. 4. As shown in FIG. 4, the base unit 5 is provided with a concave mating component 12 into which the mating component 11 of the base unit 5 (see FIG. 5A) is fitted. This makes positioning easier when the transmitter 7 is attached to the base unit 5.

Connection Configuration of Base Unit, Sensor Unit, and Transmitter

As shown in FIG. 4, an arrow 13a indicating the attachment position of the sensor unit 6 is provided to the mating component 12 provided on the upper face of the base unit 5.

The arrow 13a indicates the installation position of a sensor unit insertion device 44 (called an applicator) when the sensor 4 is inserted into the patient's body in a state in which the sensor unit insertion device 44 is pressed against the base unit 5, as will be described below.

Similarly, an arrow 14a is provided to the upper face of the transmitter 7 so as to indicate the position of the sensor unit 6. Consequently, by aligning the orientation of the arrow 14a of the transmitter 7 so as to match the orientation of the arrow 13a of the base unit 5, the transmitter 7 can be easily positioned and attached to the base unit 5.

FIG. 6A is a lateral cross section of the sensor attachment device 1.

The part labeled B in FIG. 6A is the portion where the convex part 10 of the sensor unit 6 is mated with the mounting hole 9 of the transmitter 7, and FIG. 6B is a detail view of this part B.

The part labeled C in FIG. 6A is the portion where the peripheral edge of the lower side face of the transmitter 7 is mated with the base unit 5, and FIG. 6C is a detail view of this C part.

A concave groove 13 is provided to the peripheral edge of the lower side face of the transmitter 7. The inner peripheral face of the disk-shaped base unit 5 is provided with the convex part 14 that projects radially inward and mates with the concave groove 13. The base unit 5 is formed from a flexible material such as an elastomer resin. When the transmitter 7 is mounted, a portion of the convex part 14 of the disk-shaped base unit 5 is pushed and spread radially outward. From this state, the convex part 14 fits into the concave groove 13 with elastic force.

Here, the concave groove 13 of the transmitter 7 is made of a resin or the like, and is formed from a material that is harder than the material of the base unit 5. Therefore, when the convex part 14 is fitted into the concave groove 13, since the convex part 14 is fitted so as to snap into the concave groove 13 with elastic force, it emits a click. This sound confirms that the transmitter 7 has been securely mounted to the base unit 5. This fitting structure makes it possible to prevent the entry of liquid from the outside.

Consequently, the transmitter 7, the base unit 5, and the sensor unit 6 are combined to each in a detachable state, and the interior of the transmitter 7 (which has an electrically conductive portion) and the electrically conductive portion of the sensor unit 6 (discussed below) are given a waterproof function.

Next, the configuration of the sensor unit 6 will be described.

Structure of Sensor Unit

Figure 8:
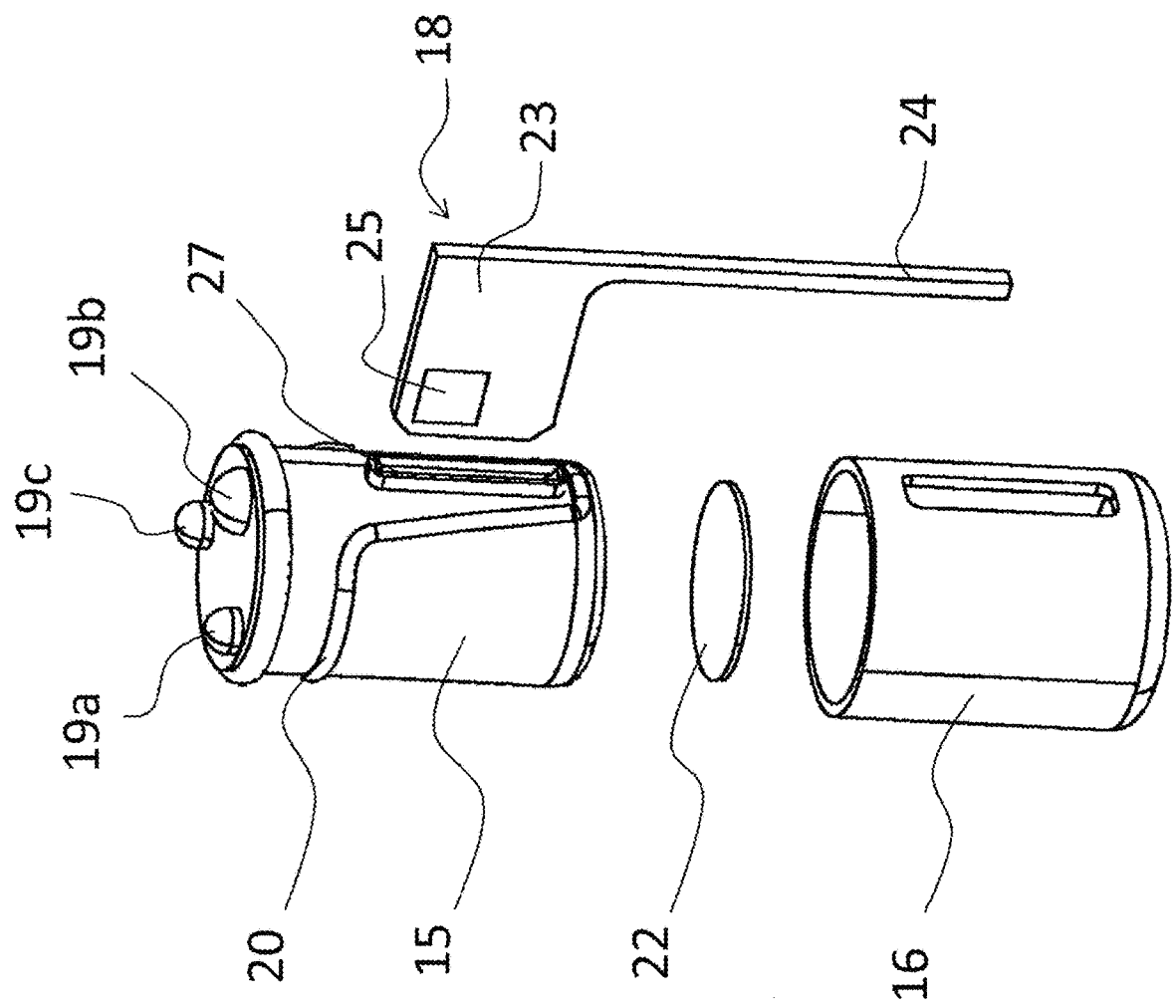
FIG. 8 is an exploded oblique view of the main part of the continuous blood glucose monitoring (CGM) device in FIG. 1.
Figure 9:
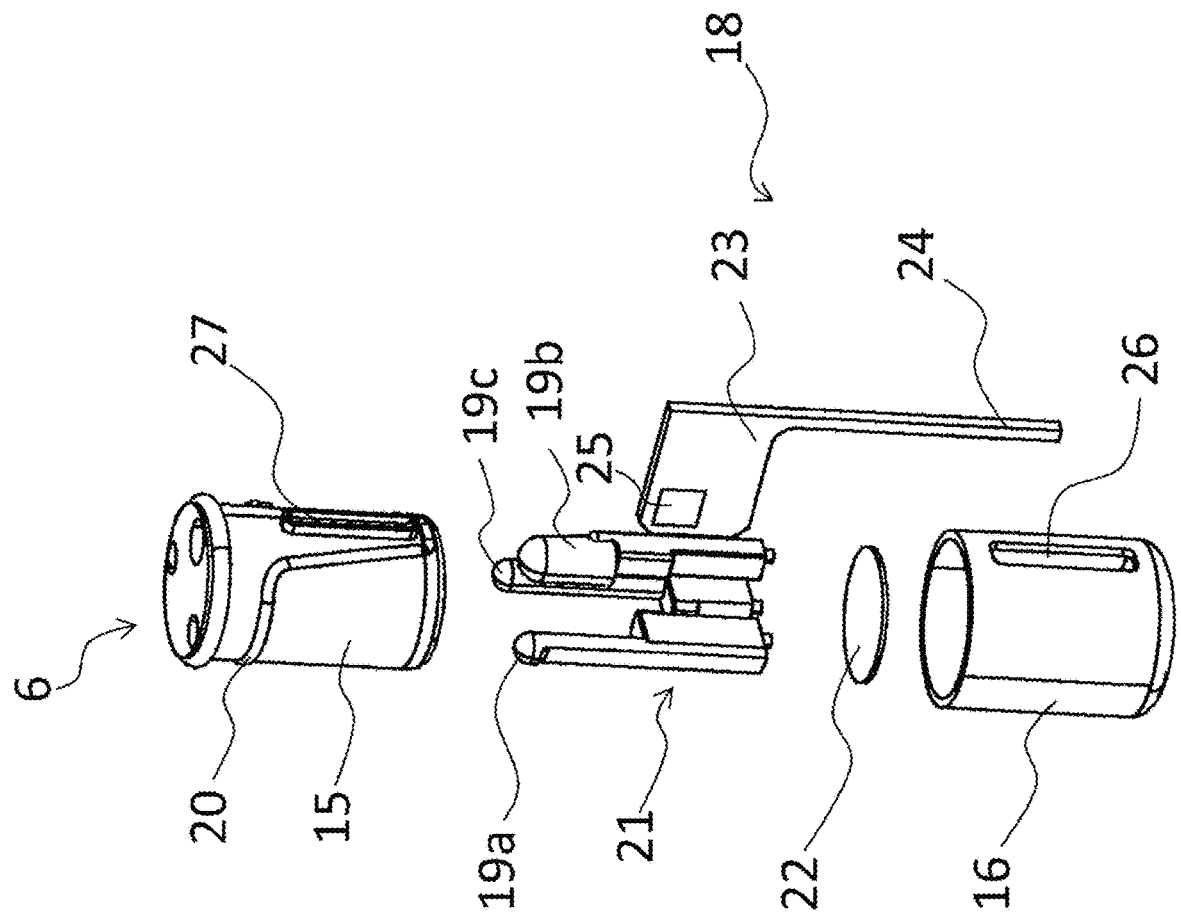
FIG. 9 is an exploded oblique view of the main part of the continuous glucose monitoring (CGM) device in FIG. 1.

FIG. 7A is a oblique view of the sensor unit 6, and FIG. 7B is a side view of the sensor unit 6. FIG. 8 is an exploded oblique view of the sensor unit 6, and FIG. 9 is an exploded oblique view in which the sensor unit 6 has been further exploded.

As shown in FIGS. 7A and 7B, the sensor unit 6 comprises the sensor main body 18 and a sensor support body 16a that supports the sensor main body 18.

The sensor support body 16a has a cylindrical first container 15 and a cylindrical second container 16 that covers the outer peripheral face of the first container 15.

One end of the sensor main body 18 is inserted into the openings in the side faces of the second container 16 and the first container 15, and the other rod-shaped end extends downward in FIGS. 7A and 7B.

Three conductive terminals 19a. 19b, and 19c are provided on the upper face of the first container 15.

FIG. 8 is an exploded oblique view of the sensor unit 6.

The first container 15 is made of a flexible, elastic material such as silicone rubber, for example. A rib 20 is formed on the side face of the first container 15.

The rib 20 is formed integrally with the first container 15. The rib 20 is also formed from a flexible, elastic material such as silicone rubber, for example, and is formed integrally with the first container 15.

As shown in FIG. 9, a connector 21 is contained in the first container 15. The lower face of the first container 15 is open, and the connector 21 is inserted through the lower face opening. To electrically insulate the connector 21 from the second container 16, an insulating lid 22 is positioned between the connector 21 and the second container 16.

The second container 16 is made of a metallic material such as stainless steel, aluminum, or brass, and is made of a material that is harder than the material of the first container 15.

When the first container 15 is inserted through the upper opening of the second container 16, the convex portion of the rib 20 provided on the side face of the first container 15 fits snugly up against the inner face of the second container 16. Furthermore, as described above, the first container 15 and the rib 20 are formed from a flexible, elastic material such as silicone rubber, and a force is exerted to expand the second container 16 from the inside. This affords a snugger fit between the first container 15 and the second container 16.

As a result, the holding force of the first container 15 on the inner peripheral face side of the second container 16 increases, and any moisture permeating between the first container 15 and the second container 16 can be prevented from infiltrating the interior of the first container 15 from the lower portion of the second container 16. That is, it is possible to improve waterproofness from the lower portion of the second container 16 to the inside of the first container 15.

In this way, in a state in which the first container 15, into the interior of which the electrical connector 21 has been inserted, is inserted from the upper part of the second container 16, the sensor main body 18 is inserted from the side so as to be connected to the connector inside the first container 15.

The sensor main body 18 has a substrate-shaped first end 23 provided above (on the rear side in the puncture direction) and a rod-shaped second end 24 below (on the front side in the puncture direction). A conductive contact 25 is provided to the substrate-shaped first end 23.

After the first end 23 of the sensor main body 18 has been inserted through an opening 26 on the side face of the second container 16, the sensor main body 18 is inserted into the interior of the first container 15 from an opening 27 on the side face of the first container 15.

Here, the opening 27 of the first container 15 is formed of a flexible, elastic material such as silicone rubber. Therefore, the opening 27 fits snugly against the substrate-shaped first end 23 of the sensor main body 18. As a result, moisture can be prevented from coming in through the opening 27 in the first container 15.

Figure 10:
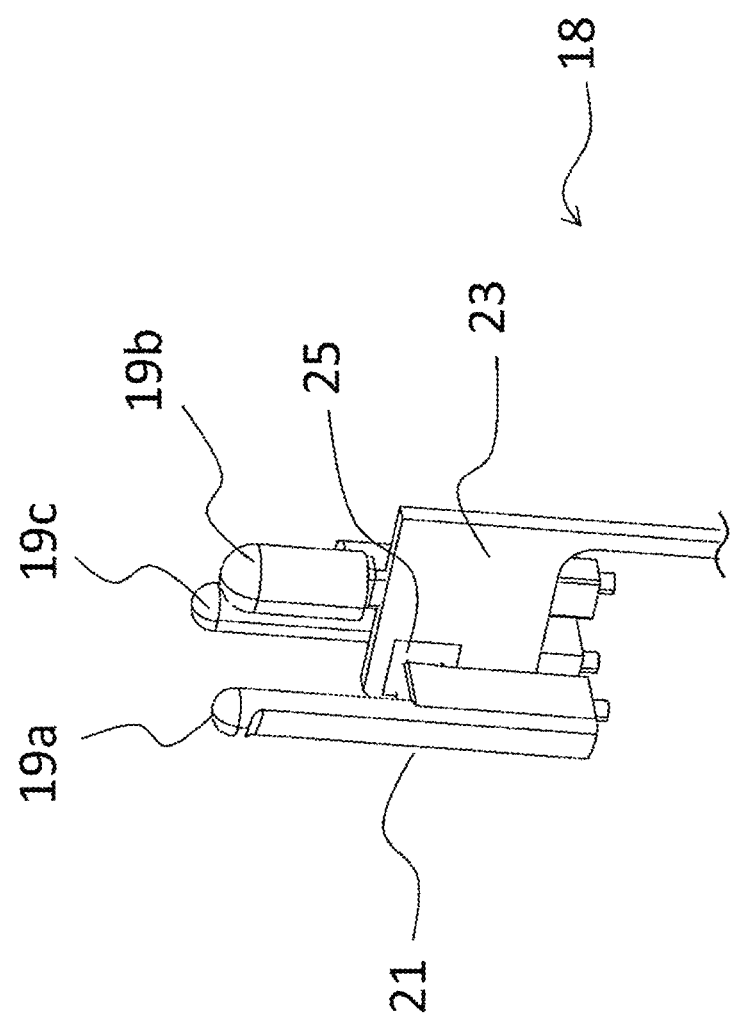
FIG. 10 is an oblique view of the main part of the continuous glucose monitoring (CGM) device in FIG. 1.

FIG. 10 shows a state in which the sensor main body 18 has been inserted into the connector 21.

As shown in FIG. 10, the connector 21 is connected to the sensor main body 18 so as to flank the contact 25 of the substrate-shaped first end 23 of the sensor main body 18. A total of three contacts 25 are provided to the substrate-shaped first end 23 of the sensor main body 18. In FIG. 10, one contact 25 is provided on the front side and two contacts 25 are provided on the back side. On the connector 21 side, one connection terminal is provided on the front side and two connection terminals are provided on the other side. The connector 21 and the sensor main body 18 are electrically connected by supporting the first end 23 of the sensor main body 18 such it is flanked by the three connection terminals.

As shown in FIG. 8, terminals electrically connected at three points are connected to the three conductive terminals 19a, 19b, and 19c. These terminals 19a, 19b, and 19c are attached so as to protrude from the upper face of the first container 15.

FIG. 11A to 11C show the connection state in the interior of the first container 15.

FIG. 11A shows a side view of the first container 15. FIG. 11B is a cross section along the A-A' line in FIG. 11A, and FIG. 11C is a cross section along the B-B' line in FIG. 11A.

The interior of the first container 15 leaves a space into which the substrate-shaped first end 23 of the sensor main body 18 is inserted, and the connection portion of three terminals 21a, 21b, and 21c of the connector 21, and is filled with a flexible, elastic nonconductive material 28 so as to surround the connector 21 with respect to the space in the rest of the interior. The base material of the first end 23 of the sensor main body 18 is PET (resin) or the like. As a result, the substrate-shaped first end 23 of the sensor main body 18 is fixed and supported at the point when it is inserted into the first container 15. In this state, the electrical contacts of the connector 21 are connected to the contacts 25 of the first end 23 so as to support at three points as mentioned above, so the connection is mechanically and electrically stable.

As shown in FIG. 11B, at the A-A' portion of the sensor unit 6 in FIG. 11A, the electrical connection is at the two points of the left and right terminals 21a and 21b. As shown in FIG. 11C, at the B-B' portion of the sensor unit 6, the electrical connection is at the one point of the right terminal 21c in FIGS. 11A to 11C. Thus making a three-point connection at positions that are in left and right asymmetry makes it possible to support a stable connection state.

With an electrical connection such as this, the connection is sometimes made with a substrate that is generally flexible. A biosensor used for CGM or the like is left under the skin of a patient's body. Accordingly, in a typical configuration, the bending portion of the flexible substrate or the like may deteriorate, which can lead to problems such as disconnection.

In the connection mode of this embodiment, there is no need to bend the sensor main body 18 itself or its connecting portion, so a mechanically and electrically stable connection mode can be realized.

In this embodiment, the contact portion of the sensor main body 18 is in the form of a substrate, but the contact portion is not limited to this shape. For instance, the configuration may be such that an electrical connector is provided to a board-shaped substrate portion, and this substrate portion is sandwiched from the front and back so as to be electrically connected. Consequently, there is no need to bend the sensor main body 18 itself or its connecting portion, so a mechanically and electrically stable connection state can be realized.

Description of Sensor Supply Unit

Figure 12B:
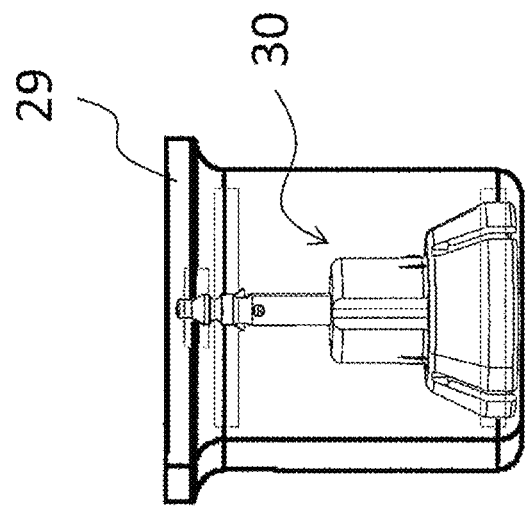
FIG. 12B is a see-through side view thereof.
Figure 12A:
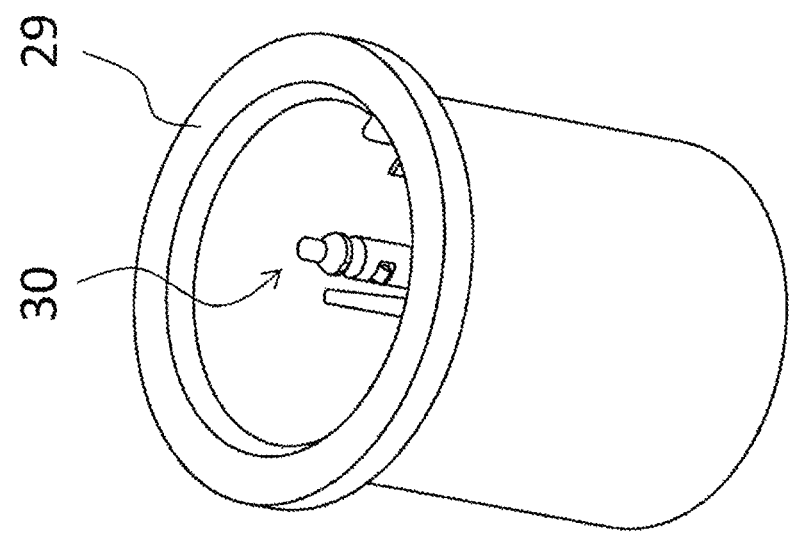
FIG. 12A is an oblique view of the main part of the continuous glucose monitoring (CGM) device in FIG. 1.

As shown in FIGS. 12A and 12B, the sensor unit 6 is supplied to the user in a state of being housed in a container 29. Inside the container 29, a sensor supply unit 30 including the sensor unit 6 is housed. The sensor supply unit 30 is housed in a sterilized state. The upper opening of the container 29 is blocked off with a seal (not shown).

Figure 13:
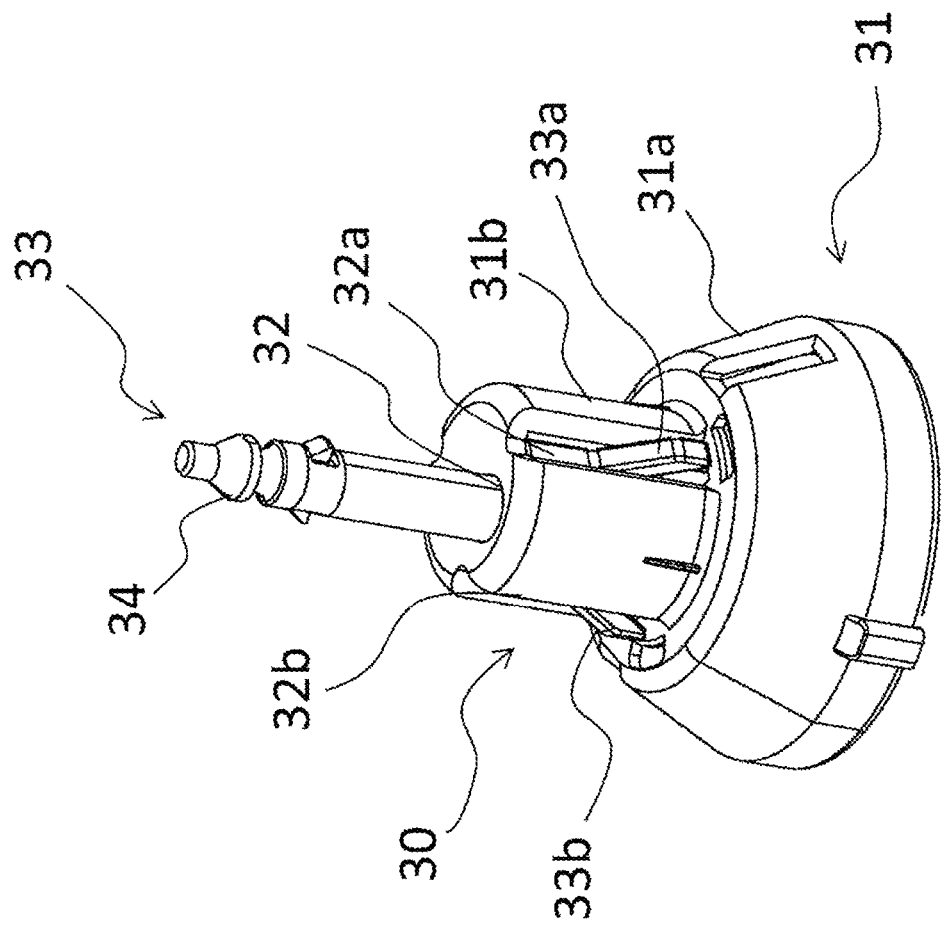
FIG. 13 is an oblique view of the main part of the continuous glucose monitoring (CGM) device in FIG. 1.

FIG. 13 is an oblique view of the sensor supply unit 30. The sensor supply unit 30 comprises a support body 31 having a truncated cone-shaped base 31a and a cylindrical head 31b, and a needle unit 33 that is supported in a slidable state in an opening 32 in the upper part of the cylindrical head 31b of the support body 31.

Figure 14:
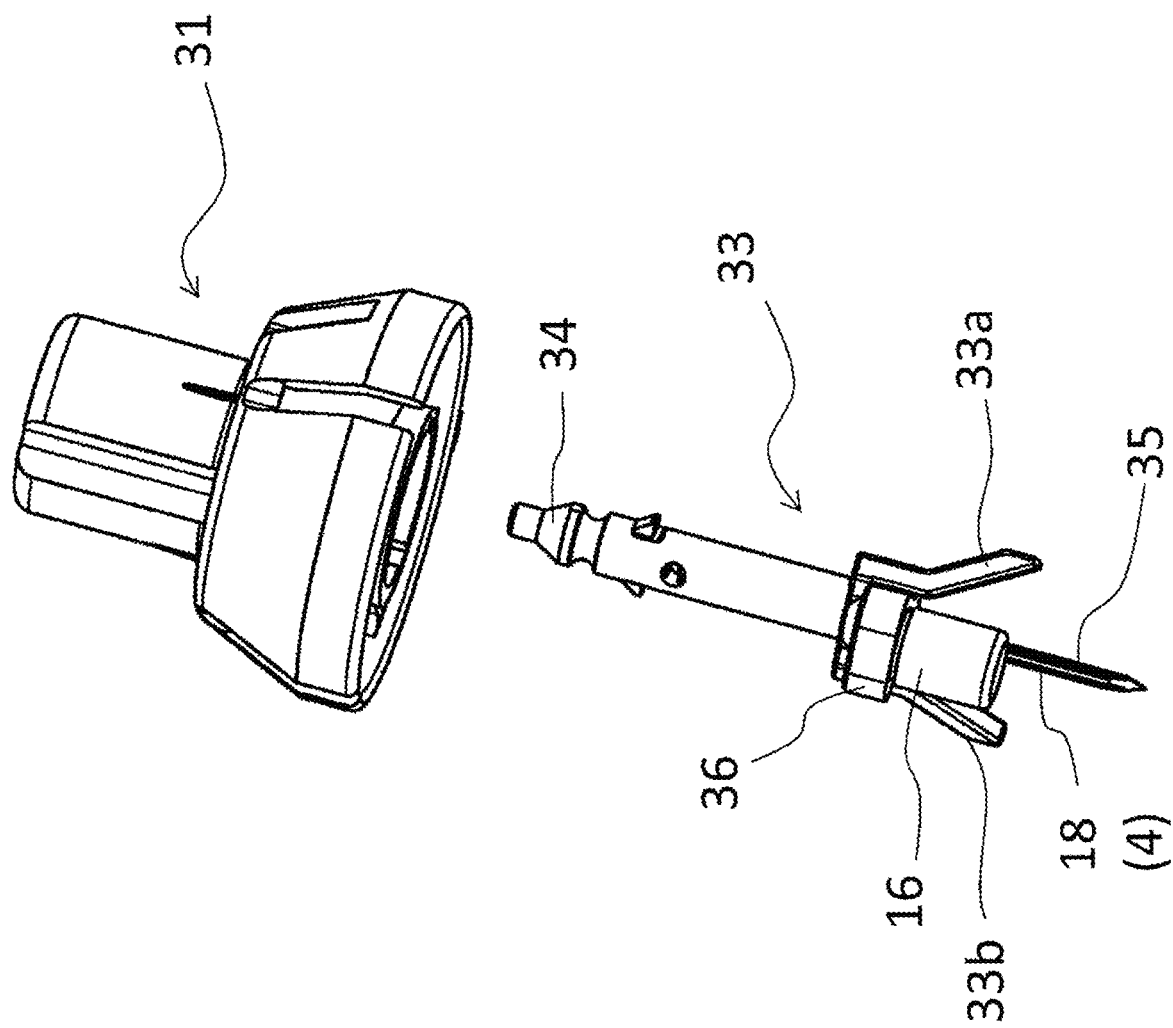
FIG. 14 is an exploded oblique view of the main part of the continuous blood glucose monitoring (CGM) device in FIG. 1.
Figure 15:
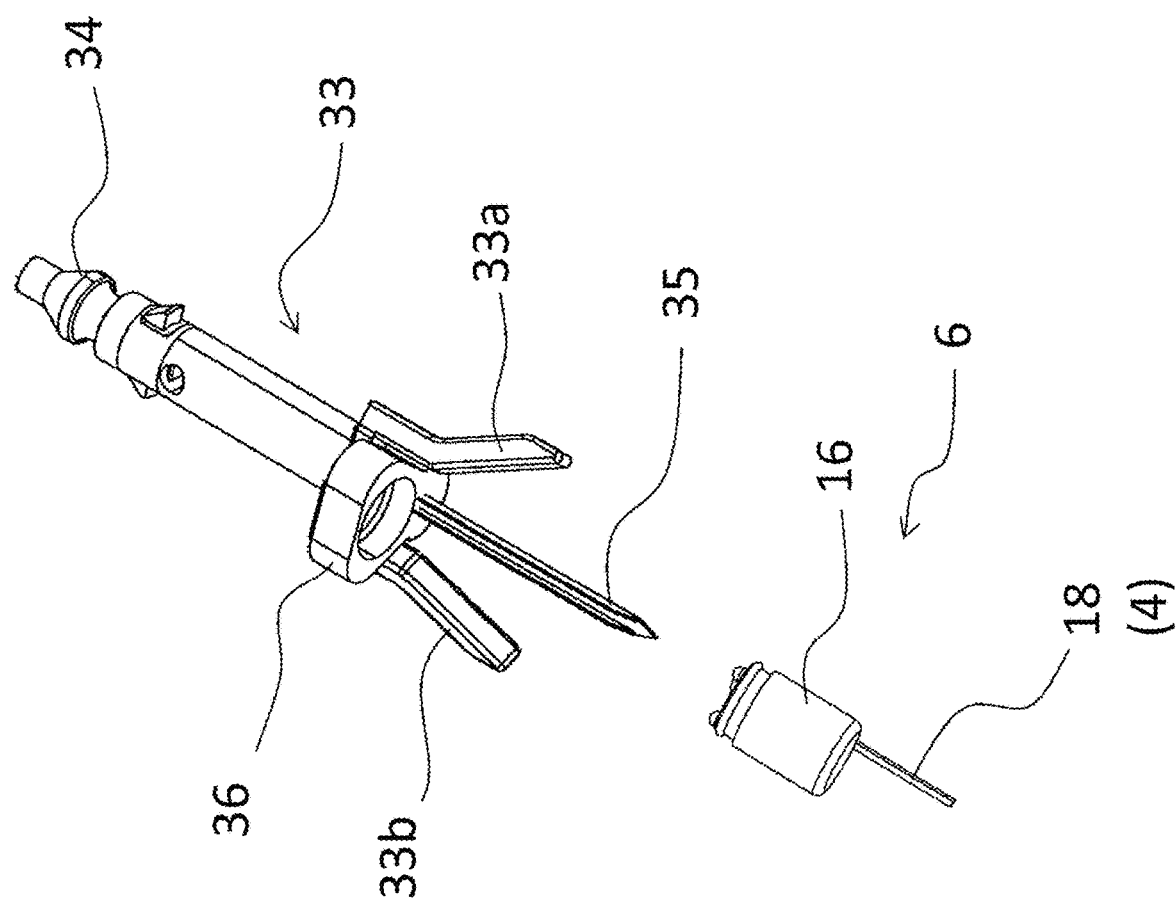
FIG. 15 is an exploded oblique view of the main part of the continuous glucose monitoring (CGM) device in FIG. 1.

FIG. 14 is an exploded oblique view of the sensor supply unit 30, and FIG. 15 is an exploded oblique view of the needle unit 33.

As shown in FIGS. 14 and 15, the needle unit 33 has at its upper part a bar-shaped grip portion 34 serving as a needle support, and a needle 35 provided to the lower end of the grip portion 34. A sensor unit support 36 having a substantially circular opening protruding in a direction substantially perpendicular to the direction of puncture by the needle 35 is provided at the connection point between the grip portion 34 and the needle 35. The cylindrical second container 16 of the sensor unit 6 is supported by this substantially circular opening portion.

The needle 35 has a pointed tip, and has an opening that communicates from the tip to the other end along the longitudinal direction. The rod-shaped sensor main body 18 of the sensor unit 6 is inserted into this opening. The sensor unit 6 is supported by the sensor unit support 36.

As shown in FIG. 13, the support body 31 is provided with the grip portion 34 for gripping the support body 31 on the upper side and an opening for sticking out the needle 35 on the lower side. Here, the configuration supported by the support body 31 itself includes only the needle 35 and the sensor 4 set in the opening of the needle 35, and the transmitter 7 is not included. Therefore, the opening of the support body 31 can be made smaller. Consequently, the needle 35 is less visible, which reduces the feeling of fear of being stuck by the needle 35, and safety can also be enhanced.

The inside diameter of this opening is less than the length of the needle 35.

As shown in FIG. 14, a pair of engagement blades 33a and 33b extending in a direction intersecting the puncture direction is provided on the outer peripheral face of the needle unit 33. As shown in FIG. 13, when the needle unit 33 is incorporated into the support body 31 from below, the engagement blades 33a and 33b engage with engagement grooves 32a and 32b in the support body 31. Consequently, the needle unit 33 does not move to the front side in the puncture direction (the lower side in the drawing). Here, when the blade portions of the engagement blades 33a and 33b shown in FIG. 13 are pressed from the radial outer side, this engaged state is released and the needle unit 33 becomes able to slide toward the front side (the lower side in the drawing).

That is, in the state of the sensor supply unit 30, the needle 35 does not slide forward and the needle 35 does not protrude, so safety can be ensured. As will be discussed below, when a puncture operation with the needle 35 is performed, the head 31b of the support body 31 is gripped and the blade portions of the engagement blades 33a and 33b are pressed from the outside, so the needle 35 is able to slide toward the front side in the puncture direction, and the puncture operation can be performed.

FIG. 16A is a cross section of the container 29 in which the sensor supply unit 30 has been set, FIG. 16B is a top view of the state when the sensor supply unit 30 has been inserted into the container 29, and FIG. 16C is a lateral cross section of FIG. 16B.

As shown in FIG. 16A, the container 29 comprises engagement components 39a and 39b that are provided to the upper face of the truncated cone-shaped base 31a of the support body 31 of the sensor supply unit 30. A support 40 that supports and houses the downward protruding needle 35 is provided in the interior of the sensor supply unit 30 in the center of the bottom face of the container 29.

Figure 17B:
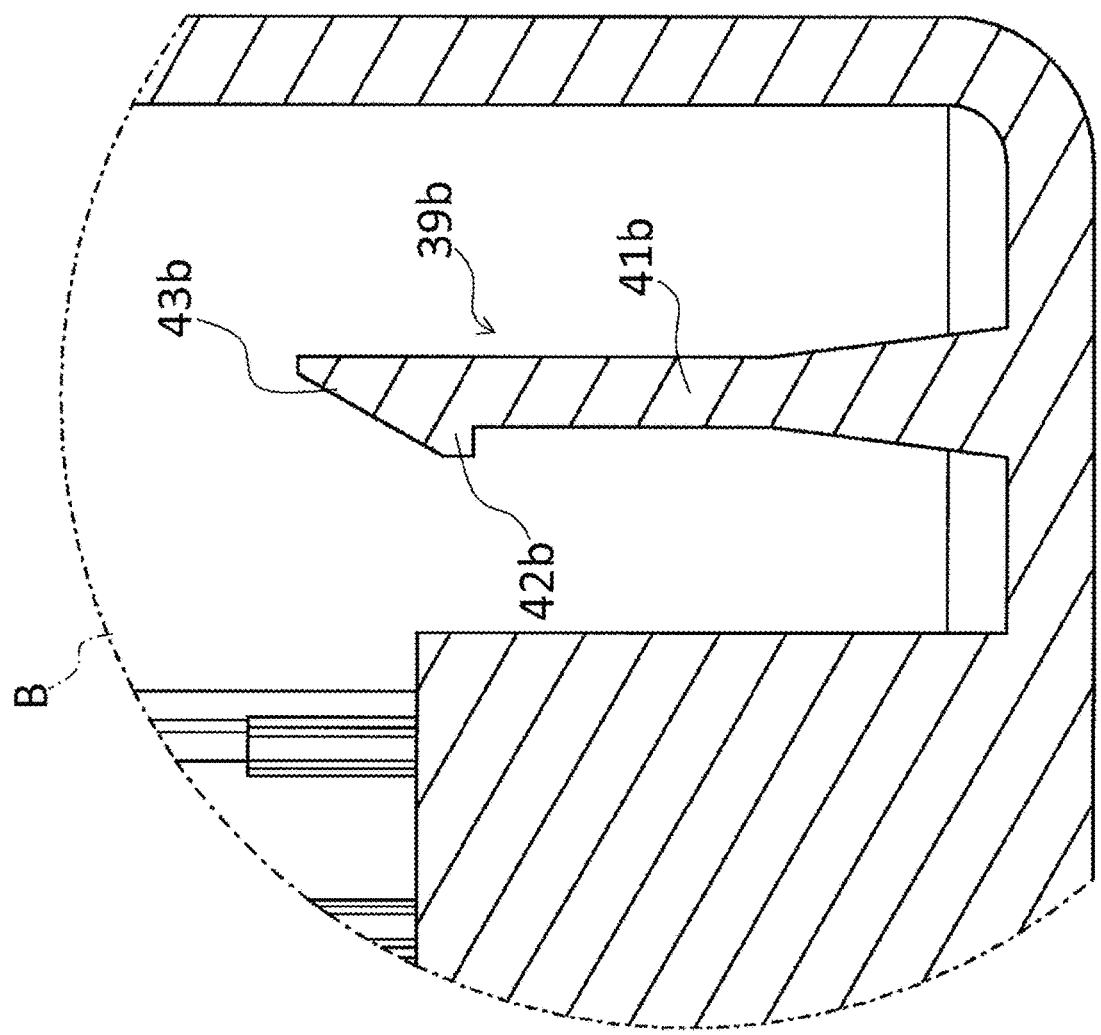
FIG. 17B is a detail view thereof.
Figure 17A:
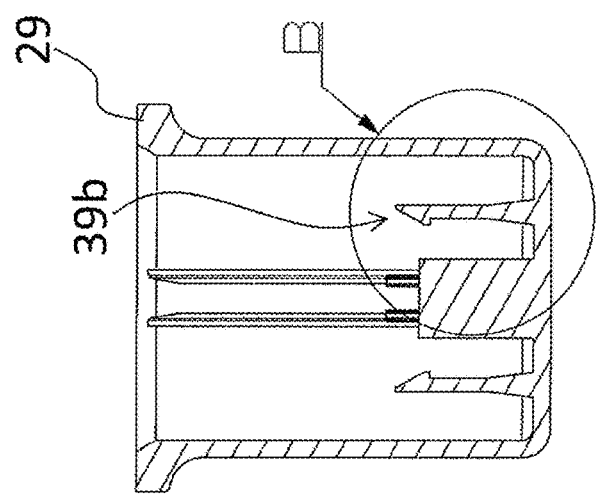
FIG. 17A is a cross section of the main part of the continuous glucose monitoring (CGM) device in FIG. 1.

FIG. 17A and FIG. 17B are detail views of the upper distal end of the engagement component 39b.

The engagement component 39b has legs 41b in the form of two supporting rods extending upward from the bottom face of the container 29. The upper ends of the engagement component 39b are each provided with an engagement prong 42b and an opening prong 43b provided at the upper part of the engagement prong 42b.

The engagement prong 42b engages with an engagement component 38b provided on the upper face of the truncated cone-shaped base 31a of the support body 31. The opening prong 43b is provided to the upper part of the engagement prong 42b at a position inclined in the direction of opening radially outward in an upward direction in order to disengage the components.

That is, the support body 31 has the engagement components 38a and 38b that engage with the engagement components 39a and 39b of the container 29 in a state of being housed in the container 29. The container 29 has an installation surface for detachably supporting the sensor supply unit 30, the engagement prongs 42a and 42b that detachably engage the sensor supply unit 30, the opening prongs 43a and 43b that are provided above the engagement prongs 42a and 42b and release the engagement by the engagement prongs 42a and 42b, and the legs 41a and 41b serving as supporting rods that support the opening prongs 43a and 43b and the engagement prongs 42a and 42b against the inner bottom face.

Therefore, it is possible to securely fix the sensor supply unit 30 to the container 29 and reliably take out the sensor supply unit 30.

The sensor supply unit 30 that supplies the sensor 4 comprises the sensor main body 18, the sensor support body 16a for supporting the sensor main body 18, the needle 35 for detachably inserting the sensor main body 18, the grip portion 34 serving as a needle support for detachably supporting the support body 16a, and the support body 31 for supporting the grip portion 34 in a slidable state.

Consequently, the sensor 4 can be supplied to the user with few components as the sensor supply unit 30. For example, the sensor supply unit 30 does not include the transmitter 7. Configuring the transmitter 7 to be detachable from the sensor unit 6 allows the transmitter 7 to be reused, and this reduces the usage cost.

Also, the support body 31 is provided with the grip portion 34 of the needle unit 33 or the head 31b as a grip portion that is gripped when the support body 31 is taken out of the container 29.

This allows the user to use the sensor 4 by gripping the grip portion 34 of the support body 31, etc., without directly touching the needle 35 or the sensor 4, which are components that come into direct contact with the user's blood or interstitial fluid. Thus, there is no need to dispose of the device for taking out the support body 31 from the container 29. In other words, since it is possible to reuse the device for taking out the support body 31 from the container 29 (the sensor unit insertion device 44 (discussed below)), the user can be provided with a sensor supply item at a lower cost. For instance, the sensor unit insertion device 44 (discussed below) inserts the sensor unit 6 into the patient's body in a state in which only the support body 31 is gripped. Therefore, the user does not touch the needle 35 or the sensor itself, so the sensor unit insertion device 44 can itself be reused.

External Appearance of Sensor Unit Insertion Device

FIG. 18A is an oblique view of the sensor unit insertion device 44.

The sensor unit insertion device 44 comprises a substantially cylindrical main body case 45, a puncture knob 46 provided at the rear end in the puncture direction of the main body case 45 (above in the drawing), a disposal knob 47 provided in the center in the longitudinal direction of the main body case 45, and a sensor supply unit grip portion 48 provided at the front end in the puncture direction of the main body case 45.

Holding Operation of Sensor Unit Insertion Device

As shown in FIG. 18B, the sensor unit insertion device 44 is inserted from the above (the open end side of the container 29) into the container 29 housing the sensor supply unit 30. Then, the sensor supply unit 30 is gripped at the distal end portion of the sensor unit insertion device 44, after which it is lifted upward as shown in FIG. 18C.

As a result, the sensor unit insertion device 44 can grip the sensor supply unit 30 at the sensor supply unit grip portion 48.

FIGS. 19A to 19D show the steps when the sensor unit insertion device 44 grips the sensor supply unit 30 at its distal end portion.

FIG. 19A shows a state in which the sensor supply unit grip portion 48 provided at the puncture direction front end of the sensor unit insertion device 44 is moving downward in the drawing toward the sensor supply unit 30 inside the container 29. The sensor supply unit grip portion 48 has an insertion component 49 formed as a substantially cylindrical opening at the front end in the puncture direction. The inside diameter of the opening portion of the insertion component 49 is set to be large enough that the cylindrical head 31b can just be inserted, matching the outside diameter of the substantially cylindrical head 31b of the support body 31 of the sensor supply unit 30.

The outside diameter of the insertion component 49 of the sensor unit insertion device 44 is less than the length between the opening prongs 43a and 43b provided at the upper ends of the two pairs of engagement components 39 provided to the container 29, and is greater than the length between the engagement prongs 42a and 42b.

FIG. 19B shows a state in which the sensor supply unit grip portion 48 is being pushed downward and the cylindrical head 31b of the support body 31 is being inserted into the opening portion of the cylindrical insertion component 49.

In the course of this insertion, the outer peripheral portion of the insertion component 49 of the sensor unit insertion device 44 is being pushed downward while sliding against the opening prongs 43a and 43b on the container 29 side.

In the state shown in FIG. 19B, the end face of the insertion component 49 of the sensor unit insertion device 44 has not yet reached the upper face of the truncated cone-shaped base 31a of the support body 31. Therefore, the opening prongs 43a and 43b are not in a sufficiently opened state.

In such a state, the engagement prongs 42a and 42b of the container 29 are still engaged with the engagement components 38a and 38b provided to the upper face of the truncated cone-shaped base 31a of the sensor supply unit 30. Consequently, in this state, the sensor supply unit 30 is held in the container 29, and the sensor supply unit 30 cannot be lifted from the container 29.

FIG. 19C shows the state when the sensor supply unit grip portion 48 is pushed down further, so that the end face of the insertion component 49 of the sensor unit insertion device 44 reaches the upper face of the truncated cone-shaped base 31a of the sensor supply unit 30.

In this state, the opening prongs 43a and 43b are sufficiently opened, and the engagement prongs 42a and 42b of the container 29 are in a state in which they have been disengaged from the engagement components 38 provided to the upper face of the truncated cone-shaped base 31a of the sensor supply unit 30. Consequently, as show in FIG. 19D, the sensor supply unit 30 can be reliably lifted from the bottom surface of the container 29.

As described above, the sensor unit insertion device 44 can take the sensor supply unit 30 out of the container 29 in a state in which the sensor supply unit 30 is being held. After this, a step is performed in which the sensor unit insertion device 44 is used to insert the sensor 4 held in the sensor supply unit 30 into the patient's body.

Figure 20:
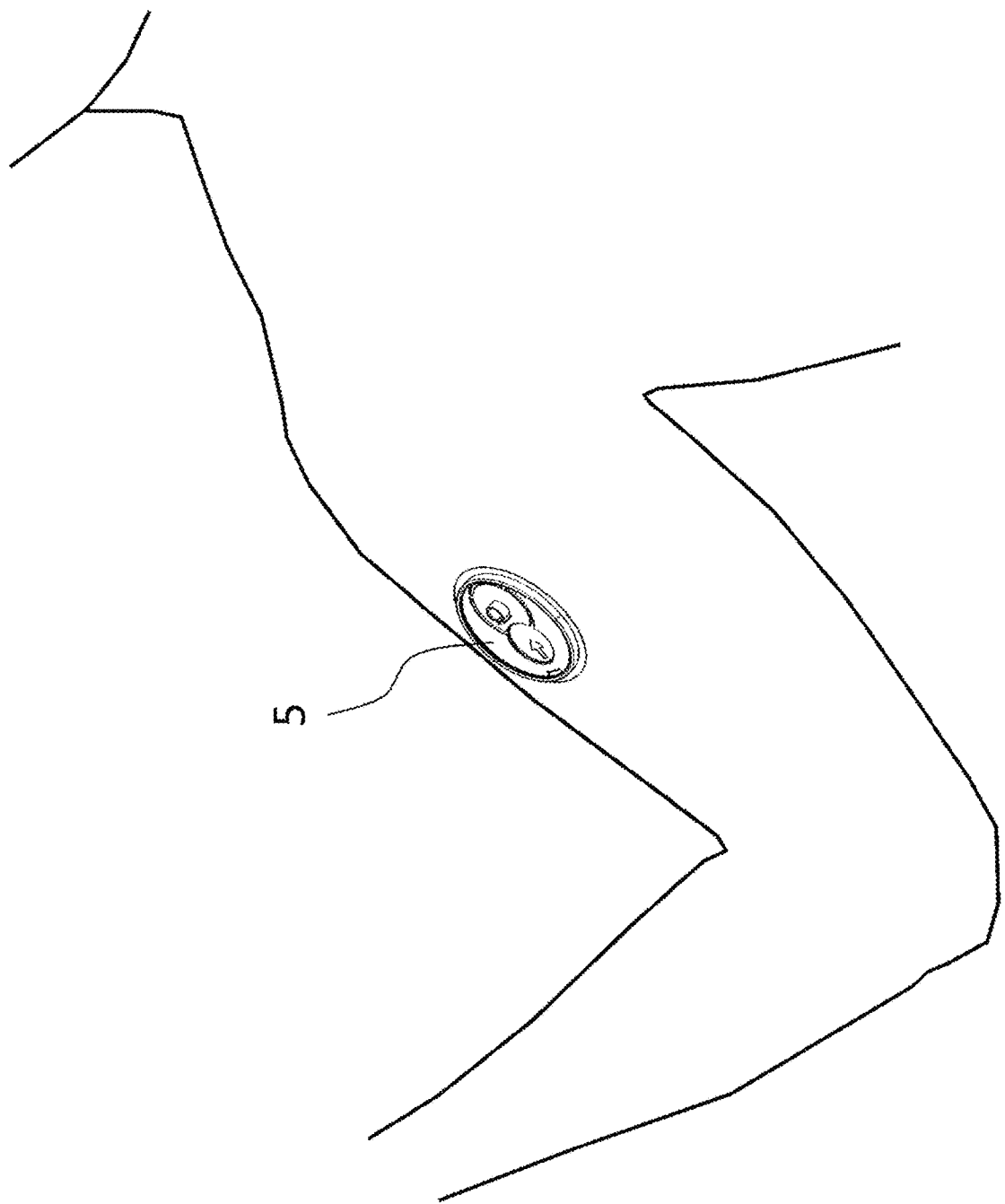
FIG. 20 illustrates the use of the continuous glucose monitoring (CGM) device in FIG. 1.

More specifically, as shown in FIG. 20, first the base unit 5, which is the part worn on the body, is affixed to the sensor insertion site on the patient's body.

Figure 21:
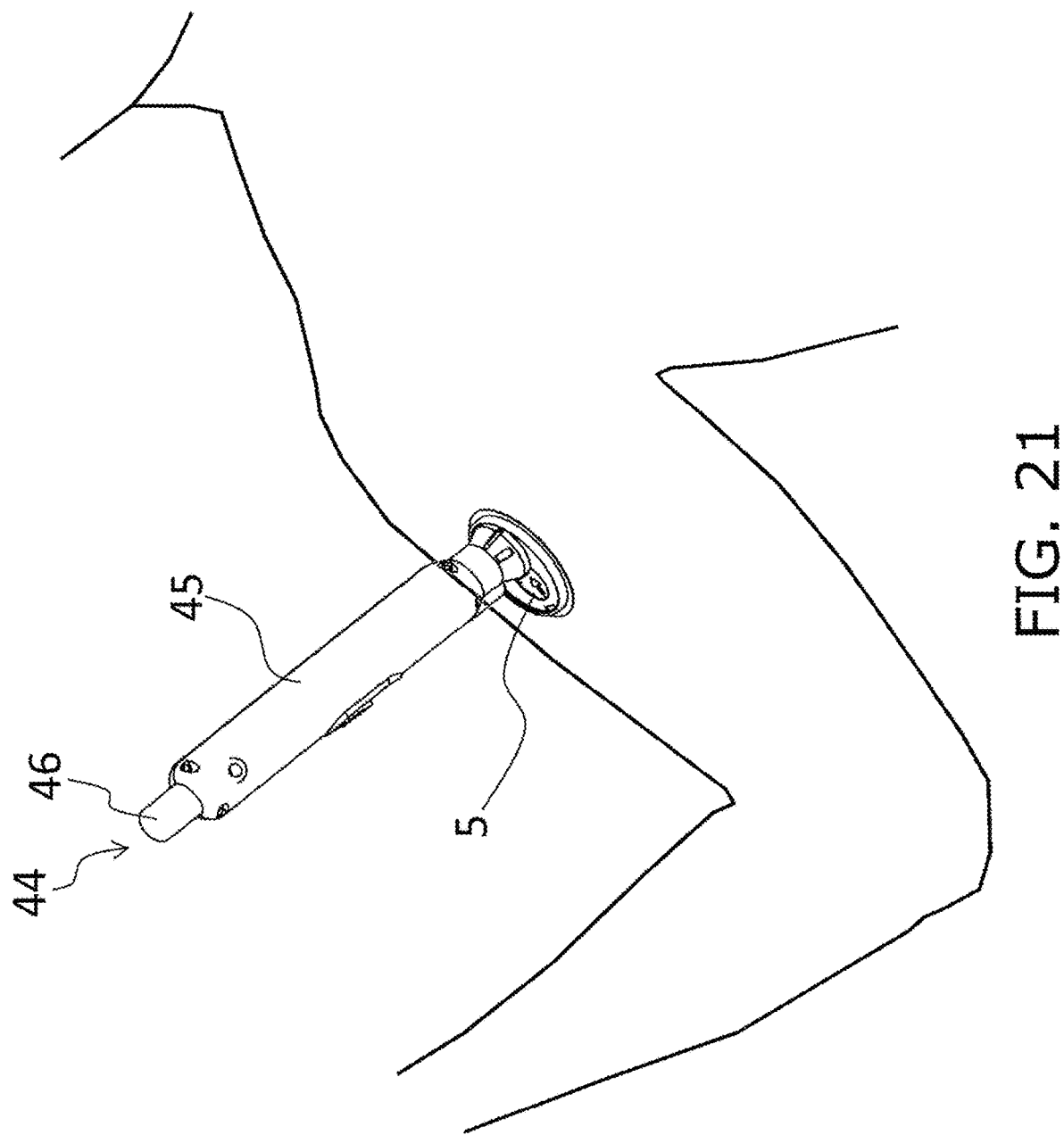
FIG. 21 illustrates the use of the continuous glucose monitoring (CGM) device in FIG. 1.

Next, as shown in FIG. 21, the sensor unit insertion device 44 gripping the sensor supply unit 30 at the front end in the puncture direction is pressed against the base unit 5 in a positioned state, and the puncture knob 46 is pushed down with a finger so that the sensor 4 is left in the patient's body.

After the sensor 4 has been inserted into the patient's body by the sensor unit insertion device 44, the sensor unit insertion device 44 is detached from the base unit 5. After this, the transmitter 7 is attached to the base unit 5 and the sensor unit 6 so that the sensor attachment device 1 can be attached to the patient's body.

Description of Sensor Unit Insertion Device Holding Operation

Next, the operation of the sensor unit insertion device 44 will be described.

FIGS. 22A to 22D show the operation when the sensor supply unit 30 is attached to the sensor unit insertion device 44.

Figures 22A, 22B, 22C, 22D:
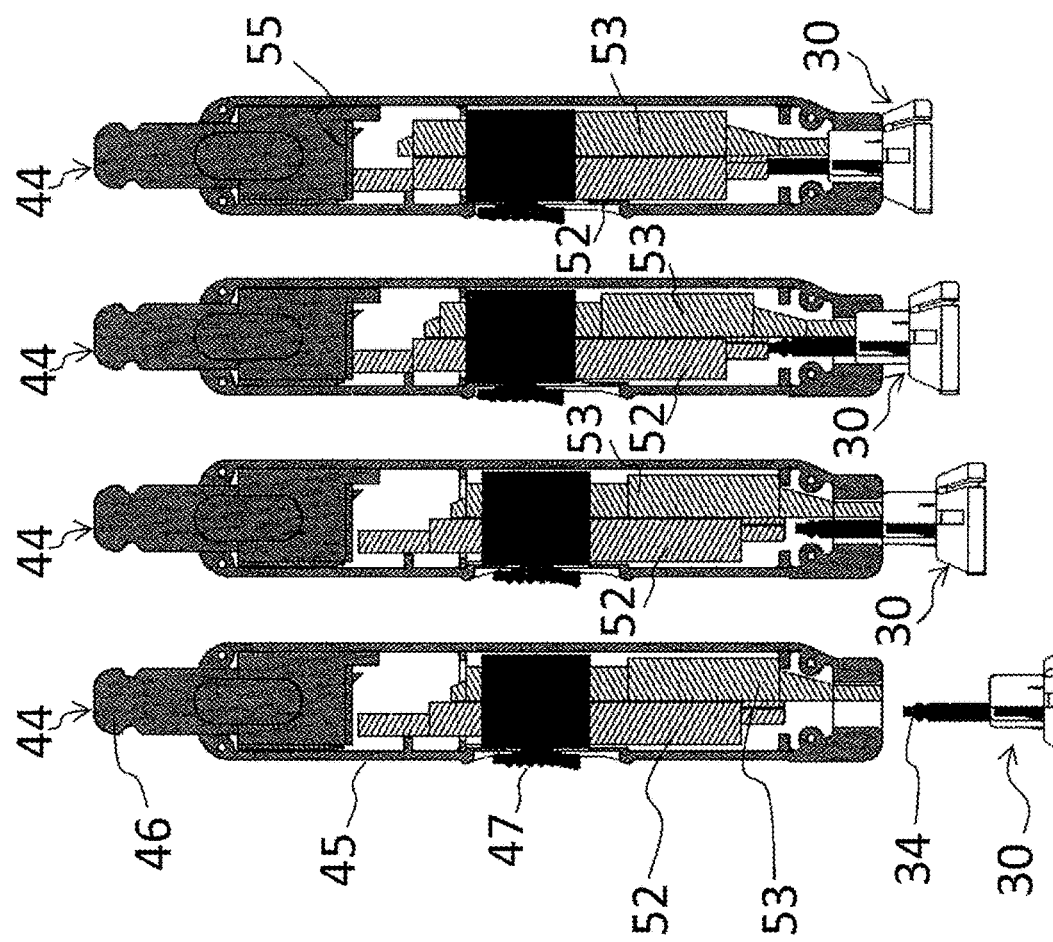
FIG. 22A is a cross section of the main part of the continuous glucose monitoring (CGM) device in FIG. 1.
FIG. 22B is a cross section thereof.
FIG. 22C is a cross section thereof.
FIG. 22D is a cross section thereof.

FIG. 22A shows the state before the sensor supply unit 30 is attached to the distal end of the sensor unit insertion device 44.

In the description of the drawings, the insertion side (the lower side in the figure) in the sensor insertion direction (puncture direction) is the front, and the opposite direction (the upper side in the figure) is the rear.

The sensor unit insertion device 44 has the main body case 45 and the sensor supply unit grip portion 48 provided in front of the main body case 45.

The sensor unit insertion device 44 has a needle slider 52 that is provided inside the main body case 45, grips the sensor supply unit 30 inserted at the front end, and slides the sensor 4 in the sensor supply unit 30 in the direction of inserting the sensor 4 into the patient's body, and a disposal slider 53 that receives a biasing force produced by a spring (biasing member) 68 (see FIG. 29, etc.) in the opposite direction from the sensor insertion direction with respect to the needle slider 52, and hits the sensor supply unit 30 inserted at the front end.

The needle slider 52 and the disposal slider 53 are configured as a first member and a second member in which a substantially cylindrical member is divided in two by a plane parallel to the puncture direction. When the needle slider 52 and the disposal slider 53 are combined, the mutually opposing faces (a first opposing face 52b and a second opposing face 53b) come into contact with each other, and in this state they slide in the puncture direction on the inner peripheral face side of the main body case 45.

Next, the sensor unit insertion device 44 is provided with the puncture knob 46, which hits the rear end (second end) of the needle slider 52 and pushes the needle slider 52 in the sensor insertion direction. The disposal knob 47, which ejects (disposes of) the sensor supply unit 30 including the needle 35 after the sensor 4 has been inserted, is provided near the center of the main body case 45.

In FIG. 22A, the sensor unit insertion device 44 is plugged into the sensor supply unit 30.

In FIG. 22B, attachment of the sensor supply unit 30 is started.

First, the sensor supply unit 30 comes into contact with the front end of the disposal slider 53 and starts to push up the disposal slider 53. Here, a spring 68 is provided in the substantially cylindrical space formed inside by putting together the needle slider 52 and the disposal slider 53. The needle slider 52 and the disposal slider 53 are linked by the spring 68. Consequently, when the sensor supply unit 30 is inserted into the sensor unit insertion device 44, the relative positions of the needle slider 52 and the disposal slider 53 change, so that the spring 68 stretches and is charged with a biasing force. Therefore, the spring 68 imparts the disposal slider 53 with a biasing force in the direction of coming into contact with the sensor supply unit 30.

In FIG. 22B, the disposal slider 53 is subjected to a forward force (a biasing force) in the puncture direction, and the user pushes this in so that the sensor unit insertion device 44 itself is pushed in toward the front in the puncture direction (downward in FIGS. 22A to 22D).

Next, in FIG. 22C, the grip portion 34 of the needle unit 33 of the sensor supply unit 30 hits the front end of the needle slider 52 and starts pushing up on the needle slider 52.

In FIG. 22D, in a state in which the rear end of the needle slider 52 has hit the front end 55 of the puncture knob 46 and cannot slide rearward in the puncture direction, the grip portion 34 of the needle unit 33 is inserted into the front end of the needle slider 52 and mated therewith. This completes the attachment of the sensor supply unit 30 to the sensor unit insertion device 44.

In this state, the sensor supply unit grip portion 48 of the sensor unit insertion device 44 grips the head 31b of the support body 31 and holds down the blade portions of the engagement blades 33a and 33b of the needle unit 33 from outside in the radial direction. Consequently, as described above, the engagement blades 33a and 33b are disengaged from the engagement grooves 32a and 32b of the support body 31, and the needle 35 is able to slide forward.

The grip portion 34 of the needle unit 33 of the sensor supply unit 30 is inserted into and mated with the opening at the front end of the needle slider 52. Consequently, the needle slider 52 does not move rearward in the puncture direction by this inserted length.

Meanwhile, the disposal slider 53 merely hits the upper face of the head 31b of the sensor supply unit 30. Therefore, the rear end of the disposal slider 53 does not hit the front end 55 of the puncture knob 46. Consequently, the disposal slider 53 slides rearward in the puncture direction by the amount that the sensor supply unit 30 was pushed into the sensor unit insertion device 44.

That is, the distance that the disposal slider 53 slides rearward in the puncture direction is longer than the distance that the needle slider 52 slides rearward in the puncture direction.

As a result, when the sensor supply unit 30 is attached to the sensor unit insertion device 44, the spring 68 imparts a biasing force that causes the needle slider 52 to slide rearward in the puncture direction by the length that the disposal slider 53 has slid in the puncture direction. This allows the biasing force required for the removal of the needle 35 after the puncture operation (discussed below) to be stored up in advance.

In other words, this biasing force is assisting energy for the next puncture operation. Therefore, at the time of the puncture operation, the pushing force or distance needed for puncture can be reduced with respect to the puncture knob 46, which further simplifies the puncture operation.

The operation of the sensor unit insertion device 44 in the puncture operation will be described through reference to FIGS. 23A to 23C.

Figures 23A, 23B, 23C:
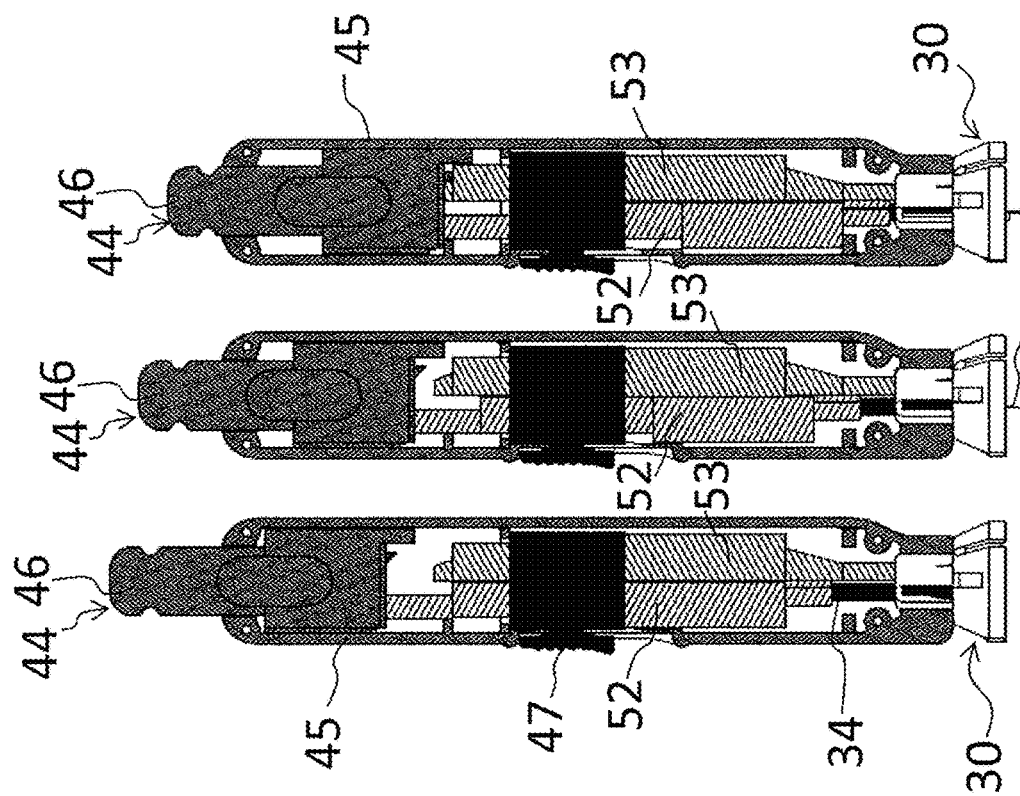
FIG. 23A is a cross section of the main part of the continuous glucose monitoring (CGM) device in FIG. 1.
FIG. 23B is a cross section thereof.
FIG. 23C is a cross section thereof.

In FIGS. 23A and 23B, when the puncture knob 46 is pushed forward, the needle slider 52 slides forward, and as a result the needle unit 33 of the sensor supply unit 30 slides forward through the open end of the support body 31.

That is, the needle unit 33 is slidably supported by the support body 31. Consequently, in a state in which the support body 31 is gripped by the sensor unit insertion device 44, the support body 31 is fixed to the sensor supply unit grip portion 48 of the sensor unit insertion device 44, in which state only the needle unit 33 can slide forward and rearward in the puncture direction.

As a result, the needle 35 of the needle unit 33 protrudes forward from the front opening of the support body 31.

FIG. 23C shows a state in which the puncture is complete, and in this state the needle 35 is as far forward as it will go.

The operation of the puncture knob 46 during this puncture operation will now be described in further detail.

FIG. 24A to FIG. 24D are operation diagrams of the puncture knob 46 during a puncture operation.

FIG. 24A shows the state at the start of the puncture operation.

The puncture knob 46 has a substantially cylindrical slider 50 that slides within the substantially cylindrical main body case 45, and plungers 56a and 56b flanking the side faces of the slider 50 from both sides. Recesses 58a and 58b that come into contact with movable distal ends 57a and 57b of the plungers 56a and 56b are provided to the side faces of the slider 50, which is the sensor insertion start position of the puncture knob 46.

As shown in FIG. 24B, in order to push the puncture knob 46 forward in the puncture direction, it is necessary to exert a force on the slider 50 so that the movable distal ends 57a and 57b of the plungers 56a and 56b will come out of the recesses 58a and 58b at the sensor insertion start position. Therefore, a pressing force is required at the initial stage of the puncture operation.

As shown in FIG. 24C, after a certain amount of force is applied and the movable distal ends 57a and 57b have come out of the recesses 58a and 58b, the puncture knob 46 is firmly pushed into the puncture completion position as shown in FIG. 24D. Therefore, at the time of a puncture operation, the user pushes the puncture knob 46 all the way in, after which the puncture operation can be completed at once. Therefore, the user can complete the puncture operation quickly, before he even has time to be afraid of the puncture.

Further, inclined faces 59a and 59b inclined downward toward the rear in the puncture direction are provided on the side faces of the slider 50 behind the recesses 58a and 58b in the puncture direction. Therefore, after the movable distal ends 57a and 57b ride up over the recesses 58a and 58b, they slide further down the slope, which reduces the force exerted on the plungers 56a and 56b as the puncture knob 46 is pushed in. Consequently, the puncture knob 46 is pushed in all at once to the puncture completion position.

Therefore, the user can push in the puncture knob 46 faster in the puncture operation. This allows the user to complete the puncture operation more easily, and to complete the puncture operation before he even has time to be afraid of the puncture.

Thus, the sensor unit insertion device 44 comprises the main body case 45, the needle slider 52 that is provided inside the main body case 45 and is provided in a state in which the sensor 4 gripped at the front end can slide in the direction of being inserted into the patient's body, and the puncture knob 46 that hits the rear end of the needle slider 52 and pushes in the needle slider 52 in the sensor insertion direction. The sensor unit insertion device 44 is provided with a load mechanism (the plungers 56a and 56b) that applies a load (resistance force) from the sensor insertion start position of the puncture knob 46 until the start of forward movement in the puncture direction.

Consequently, the user can perform the operation of pushing in the puncture knob 46 faster in the puncture operation. As a result, the user can complete the puncture more easily and reliably, and can complete the puncture operation before he even has time to be afraid of the puncture.

FIGS. 25A to 25C show the operation of removing the needle 35, which is performed immediately after the puncture operation.

A puncture operation was described above, but after the puncture operation, it is preferable to quickly remove just the needle 35 in a state in which the sensor 4 is left under the skin.

FIG. 25A shows a state in which the front end 55 of the puncture knob 46 hits the rear end of the needle slider 52, and the needle slider 52 is pushed in in the sensor insertion direction and is in contact with the rear end of the disposal slider 53.

FIGS. 25B and 25C show a state in which the needle 35 is pulled out by sliding the needle slider 52 all at once to the rear in the puncture direction by means of an opening mechanism that opens up the portion where the rear end of the disposal slider 53 has hit on the front end 55 side of the puncture knob 46.

This opening mechanism comprises a window body 61 serving as the lid of an insertion hole 60 into which the rear end (second end) of the needle slider 52 is inserted, and a handle 63 that switches the window body 61 to an open state upon hitting the rear end of the disposal slider 53.

In this embodiment, two modes are employed for this opening mechanism and a return mechanism (discussed below).

FIGS. 26A to 26C show an example of the opening mechanism.

The opening mechanism of the puncture knob 46 shown in FIGS. 26A to 26C has a window body (opening mechanism) 61 that slides to open and close the opening of the insertion hole 60 into which the rear end of the needle slider 52 is inserted, an elastic body (return mechanism) 62 that biases the window body 61 in the direction of closing the opening of the insertion hole 60, and a handle (opening mechanism) 63 that slides in contact with the rear end in the puncture direction of the disposal slider 53 to slide the window body 61 in the direction of opening.

With this opening mechanism, as shown in FIGS. 26B and 26C, the rear end of the disposal slider 53 in the puncture direction comes into contact with the handle 63, and the window 61 slides to the right in the drawings. When the opening end of the insertion hole 60 is opened by the movement of the window 61, the window body 61 that is in contact with the rear end of the needle slider 52 is retracted and the opening end of the insertion hole 60 is exposed, so the needle slider 52 goes into a state of being able to move backward in the puncture direction. At this point, the rear end of the needle slider 52 is inserted into the insertion hole 60 by the biasing force toward the rear in the puncture direction produced by the spring 68.

Consequently, after a manual puncture operation by the user, the needle 35 can be pulled out by sliding the needle slider 52 rearward in the puncture direction all at once by means of the above-mentioned opening mechanism and the biasing force of the spring 68.

The opening mechanism and the return mechanism included in the sensor unit insertion device 44 in this embodiment are not limited to the configuration shown in FIGS. 26A to 26C.

FIGS. 27A to 27F show another example of the opening mechanism and the return mechanism.

The opening mechanism of the puncture knob 46 shown in FIGS. 27A to 27F has a window body (opening mechanism) 65 that rotates to open or close the opening of the insertion hole 60 into which the rear end (second end) of the needle slider 52 is inserted, an elastic body (return mechanism) 66 that biases the window body 65 in the direction of blocking off (closing) the opening side of the insertion hole 60, and a handle 67 that slides in contact with the end of the disposal slider 53 and rotates in the direction of opening the window body (opening mechanism) 65.

FIGS. 27A, 27B, and 27C show a puncture operation in which the puncture knob 46 is pushed in forward.

In FIG. 27C, in a state in which the puncture knob 46 has been pushed in forward and the needle slider 52 has slid forward in the puncture direction, the handle 67 of the opening mechanism at the front end of the puncture knob 46 is touching the rear end of the disposal slider 53.

Consequently, as shown in FIGS. 27C to 27F, the rear end of the disposal slider 53 hits the handle 67 and the window 65 rotates. When the rotation of the window body 65 changes the opening end side of the insertion hole 60 from a closed state to an open state, the rear end portion of the needle slider 52 is inserted due to the rearward biasing force in the puncture direction by the spring 68. As a result, the needle 35 can be pulled out by sliding the needle slider 52 rearward in the puncture direction all at once under the biasing force of the spring 68.

Thus, the sensor unit insertion device 44 is provided with the main body case 45, the needle slider 52 that is provided inside the main body case 45 and is provided in a state of being able to slide in the direction of inserting the sensor main body 18 gripped at the front end by the main body case 45 into the patient's body, the disposal slider 53 that is biased in the opposite direction from the sensor insertion direction with respect to the needle slider 52 by the spring 68, and the puncture knob 46 that hits the rear end of the needle slider 52 to push in the needle slider 52 in the sensor insertion direction. The sensor unit insertion device 44 is provided with an opening mechanism that opens the contact portion at the rear end of the needle slider 52 when the needle slider 52 slides forward a specific distance in the puncture direction in the insertion of the sensor 4 into the patient's body.

This allows the needle 35 to be inserted and pulled out quickly, which makes it possible to reduce the time that the needle 35 is left under the skin during puncture, and this alleviates the pain felt by the patient.

FIGS. 28A to 28E show the operations for disposing of and initializing the sensor unit insertion device 44.

FIG. 28A shows the state when the needle 35 has been removed.

In FIG. 28B, when the disposal knob 47 is pushed forward in the puncture direction, both the needle slider 52 and the disposal slider 53 are pushed down at the same time, and the ejection of the sensor supply unit 30 begins.

In FIG. 28C, the disposal knob 47 has been pushed out all the way in the puncture direction, but the grip portion 34 of the needle unit 33 of the sensor supply unit 30 is in a state of being mated to the front end of the needle slider 52, so that the sensor supply unit 30 will not fall out.

In FIG. 28D, the sensor supply unit 30 is grasped and pulled out by the hand of the user, and the sensor supply unit 30 is removed from the distal end of the sensor unit insertion device 44 and discarded.

In FIG. 28E, the puncture knob 46 returns to the rear side in the puncture direction and returns to its initial state. At this point the opening mechanism is also reset.

Figure 29:
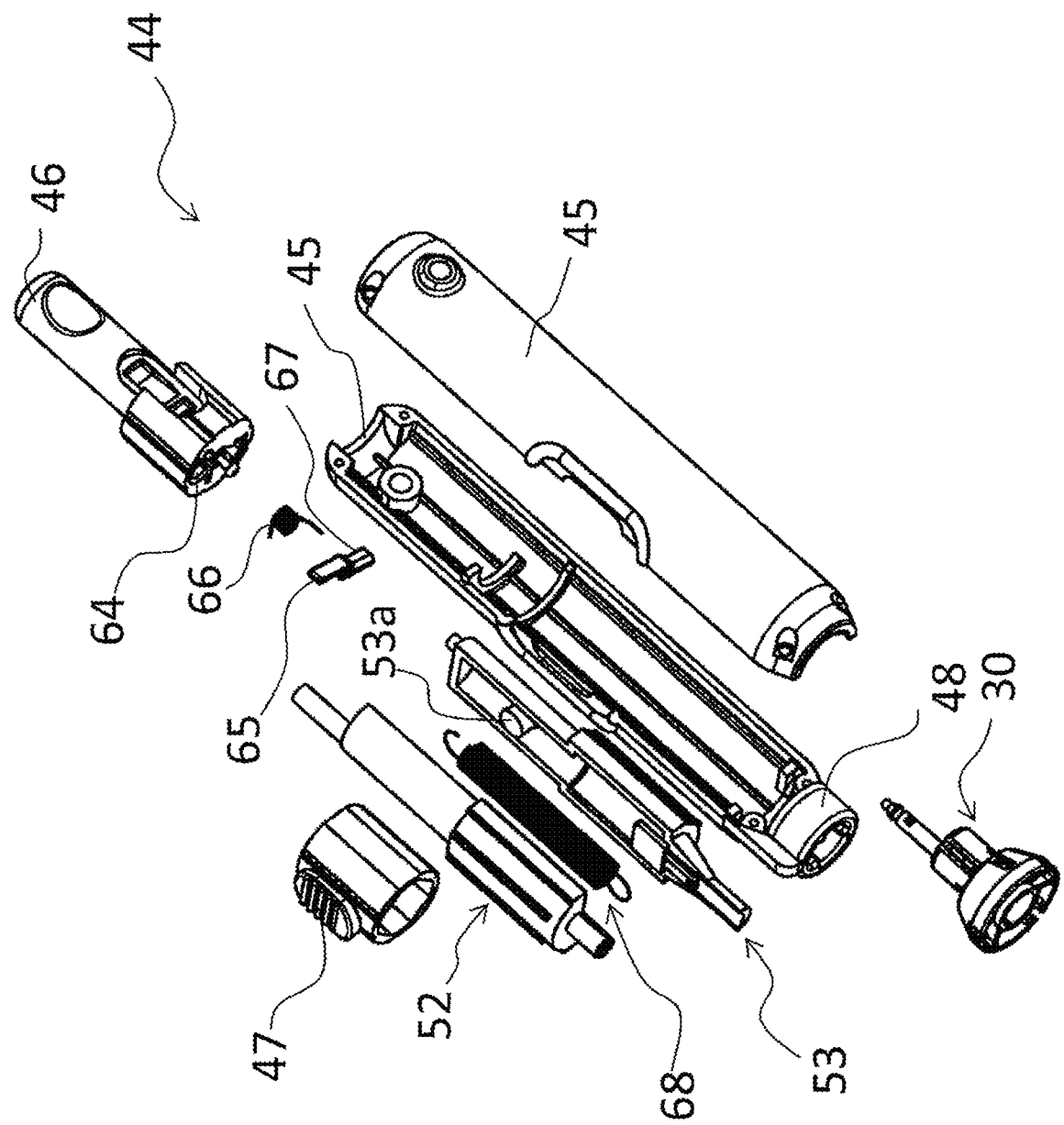
FIG. 29 is an exploded oblique view of the configuration of the sensor unit insertion device included in the continuous glucose monitoring (CGM) device in FIG. 1.

FIG. 29 is an exploded oblique view of the sensor unit insertion device 44.

The sensor unit insertion device 44 has the main body case 45 and the sensor supply unit grip portion 48 that is provided in front of the main body case 45 in the puncture direction.

The sensor unit insertion device 44 is provided with the needle slider 52 that is provided in the main body case 45, grips the sensor supply unit 30 inserted at the front end, and slides the sensor 4 inside the sensor supply unit 30 in the direction of being inserted into the patient's body, and the disposal slider 53 that is biased by the spring 68 in the opposite direction from the sensor insertion direction with respect to the needle slider 52 and hits the sensor supply unit 30 inserted at the front end.

Figure 34:
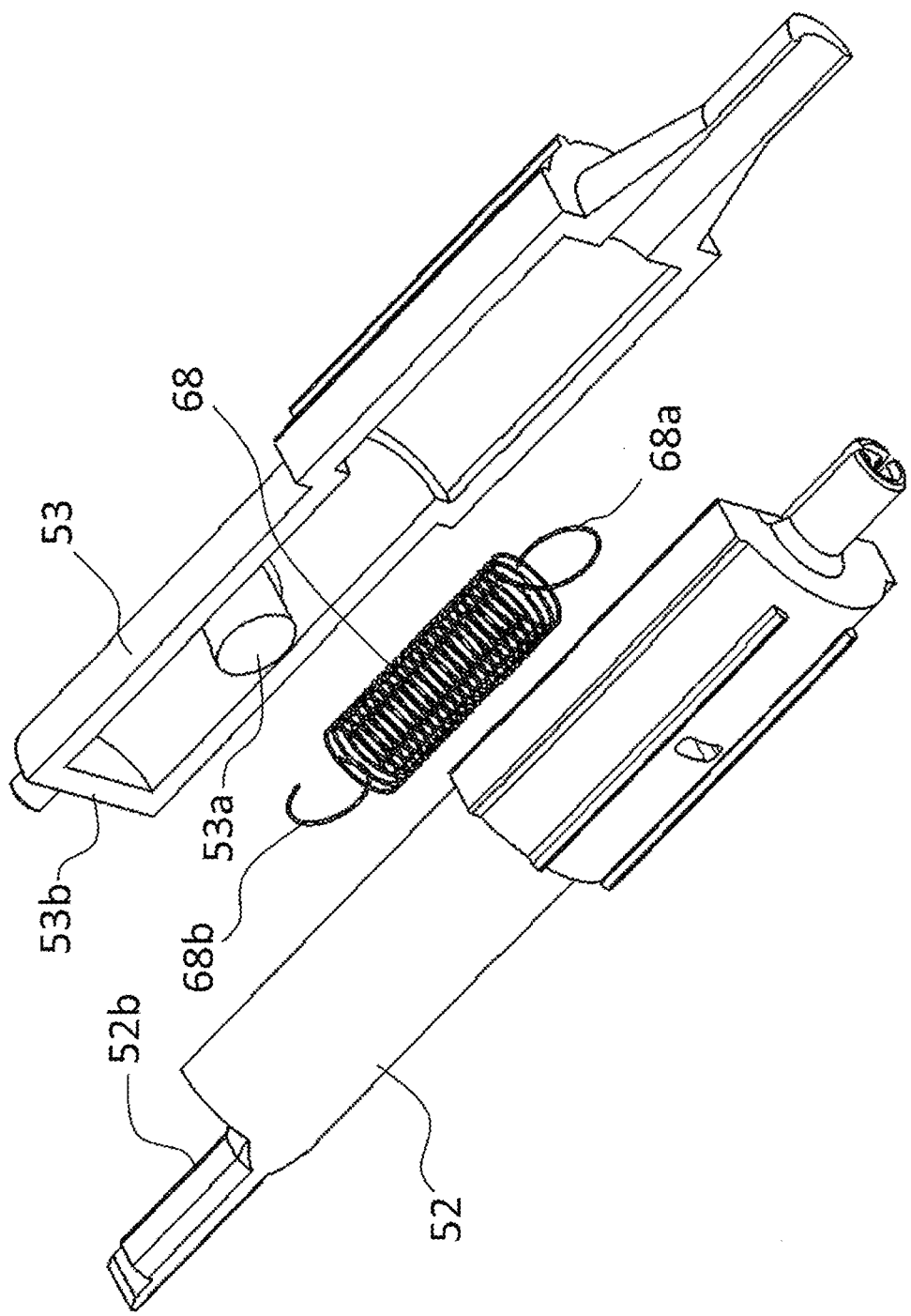
FIG. 34 is an exploded oblique view of the configuration of the main part of the continuous blood glucose monitoring (CGM) device in FIG. 1.
Figure 35:
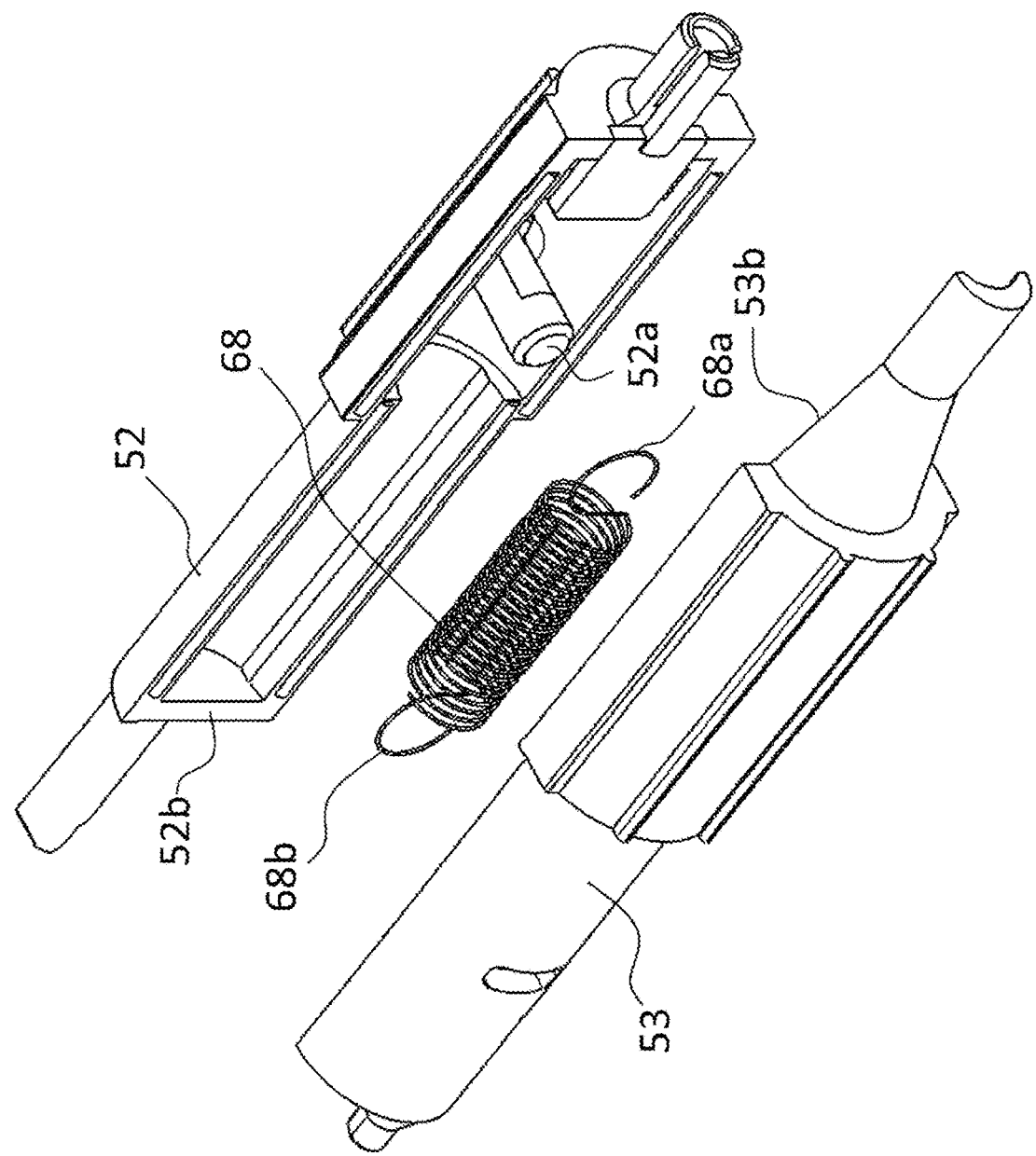
FIG. 35 is an exploded oblique view of the configuration of the main part of the continuous blood glucose monitoring (CGM) device in FIG. 1.

The spring 68 is connected at its ends to a latching portion 53a (see FIG. 34) provided to the rear of the disposal slider 53 in the puncture direction, and a latching portion 52a (see FIG. 35) provided in front of the needle slider 52. More specifically, a first end 68a on the puncture side of the spring 68 (see FIG. 35) is latched to the latching portion 52a provided on the inner peripheral face of the needle slider 52. Meanwhile, a second end 68b on the opposite side of the spring 68 from the puncture side (see FIG. 34) is latched to the latching portion 53a provided on the inner peripheral face of the disposal slider 53.

Here, as shown in FIG. 22A, in the initial state in which the disposal slider 53 has slid to the front side with respect to the needle slider 52, the spring 68 is not biasing. As shown in FIGS. 22B to 22D, as the relative positions of the needle slider 52 and the disposal slider 53 shift, the spring 68 linking the needle slider 52 and the disposal slider 53 stretches, and a biasing force is generated in the direction of returning to the state shown in FIG. 22A.

The sensor unit insertion device 44 is provided with the puncture knob 46 that hits the rear end of the needle slider 52 to push in the needle slider 52 forward in the sensor insertion direction.

That is, when the puncture knob 46 is pushed in forward and the needle slider 52 slides forward in the puncture direction in a state in which the disposal slider 53 is fixed, there is a change in the relative positions in the puncture direction of the needle slider 52 and the disposal slider 53. At this point, the spring 68 linked to the needle slider 52 and the disposal slider 53 stretches and its biasing force is stored.

As a result, the needle slider 52 is biased rearward in the puncture direction by the biasing force of the spring 68.

With the sensor unit insertion device 44 in this embodiment, after the puncture operation in which the needle 35 and the sensor 4 are inserted under the skin of the patient by manual user operation, just the needle 35 is removed, leaving the sensor 4 under the skin, by means of the biasing force of the spring 68, which is directed rearward in the puncture direction.

As described above, the opening mechanism of the puncture knob 46 has the window body 61 (or the window body 65) that rotates to open and close the opening side of the insertion hole 60 into which the rear end of the needle slider 52 is inserted, and the handle 63 (or the handle 67) that slides in contact with the rear part of the disposal slider 53 and slides the window body in the direction of opening the window body.

After the sensor 4 is inserted under the skin, the disposal knob 47 for ejecting (discarding) the sensor supply unit 30 from the tip of the sensor unit insertion device 44 is provided near the center of the main body case 45.

The sensor supply unit 30 in this embodiment has the sensor main body 18, the sensor support body 16a that supports the sensor main body 18, the needle 35 that detachably inserts the sensor main body 18, the grip portion 34 that fixes and supports the needle 35 and serves as a needle support for detachably supporting the sensor support body 16a, and the support body 31 that supports the grip portion 34 serving as a needle support in a slidable state. The support body 31 has an installation face installed in the container 29 that houses the support body 31, and engagement components 38a and 38b that engage with engagement components 39a and 39b provided on the container 29 side.

With this configuration, the sensor supply unit 30 can be packaged in a state of being fixed inside the container 29.

The container 29 in this embodiment has an opening at the top, and is a container for housing the sensor supply unit 30, and comprises the engagement prongs 42a and 42b serving as engagement components that detachably engage the sensor supply unit 30 provided on the inner bottom face of the container 29, the opening prongs 43a and 43b that are provided above the engagement prongs 42a and 42b and serve as opening components that open up the engagement prongs 42a and 42b, and the legs 41a and 41b that support the opening prongs 43a and 43b and the engagement prongs 42a and 42b with respect to the inner bottom face.

With this configuration, the sensor supply unit 30 can be packaged in a state of being fixed inside the container 29.

The sensor supply unit 30 in this embodiment includes the sensor main body 18, the sensor support body 16a that supports the sensor main body 18, the needle 35 for detachably inserting the sensor main body 18, the grip portion 34 serving as a needle support that fixes and supports the needle 35 and detachably supports the support body 16a, and the support body 31 that supports the grip portion 34 serving as a needle support in a slidable state. The support body 31 is provided with a head 31b serving as a grip portion that is gripped when the support body 31 is taken out.

Consequently, more reusable parts, such as the applicator (the sensor unit insertion device 44) and the transmitter 7, are used than in prior art, so the use cost to the user can be reduced.

The biosensor in this embodiment comprises the sensor main body 18 that senses biological information and converts it into an electric signal, and the sensor support body 16a that supports the sensor main body 18 and inputs an electric signal from the sensor main body 18. The sensor main body 18 has the second end 24 as a measurement component that is inserted into the patient's body, and the substrate-like contacts 25 that are fixed and connected to the measurement component. The sensor support body 16a has the first container 15 into which the contacts 25 of the sensor main body 18 are inserted. The connector 21 that sandwiches the contacts 25 of the sensor main body 18 is provided in the first container 15.

This configuration stabilizes the electrical connection portion of the biosensor.

The biosensor in this embodiment comprises the sensor main body 18 that senses biological information and converts it into an electric signal, and the sensor support body 16a that supports the sensor main body 18 and inputs electric signals from the sensor main body 18. The sensor main body 18 has the second end 24 as a measurement component that is inserted into the patient's body, and the substrate-like contacts 25 that are connected to the measurement component. The sensor support body 16a has the cylindrical first container 15 into which the contacts 25 of the sensor main body 18 are inserted, the connector 21 that sandwiches the contacts 25 of the sensor main body 18 provided in the first container 15, and the second container 16 that has a cylindrical shape covering the first container 15.

This configuration improves the waterproofness of the biosensor.

The sensor mounting body in this embodiment is configured such that the base unit 5 worn on the patient's body, the sensor unit 6 including the sensor main body 18 that is left in the body, and the transmitter 7 that calculates and stores biological information from the signals inputted from the sensor unit 6 are combined in a detachable state.

This configuration allows the transmitter 7 to be reused and reduces the usage cost to the user.

The sensor unit insertion device 44 in this embodiment takes the sensor supply unit 30 out of the container 29 in a state of supporting the sensor 4, and inserts the sensor 4 supported by the sensor supply unit 30 into the patient's body. The sensor unit insertion device 44 comprises the main body case 45 and the sensor supply unit grip portion 48 provided below the main body case 45. The sensor supply unit grip portion 48 is provided with the insertion component 49 of the sensor supply unit having an opening underneath.

This configuration allows the sensor unit insertion device 44 to take out the sensor supply unit 30 supporting the sensor 4 from the inside of the container 29 and securely grip it.

The sensor unit insertion device 44 in this embodiment includes the main body case 45, the needle slider 52 that is provided inside the main body case 45 and is provided in a state of being capable of sliding in the direction of inserting the sensor 4 gripped at the front end into the patient's body, the disposal slider 53 that uses the spring 68 to bias the needle slider 52 in the opposite direction from the sensor insertion direction, and the puncture knob 46 that hits the rear end of the needle slider 52 to push in the needle slider 52 in the sensor insertion direction. The sensor unit insertion device 44 is provided with an opening mechanism that opens up the contact portion of the rear end of the needle slider 52 when the needle slider 52 slides forward in the puncture direction by a specific distance in the insertion of sensor 4 into the patient's body.

This configuration allows for faster switching between the puncture operation and the extraction operation of the needle 35, which makes the sensor unit insertion device 44 more convenient to use for the user.

The sensor unit insertion device 44 in this embodiment comprises the main body case 45, the sensor supply unit grip portion 48 that is provided in front of the main body case 45, the needle slider 52 that is provided in the main body case 45, grips the sensor supply unit 30 inserted at the front end, and slides in the direction of inserting the sensor 4 in the sensor supply unit 30 into the patient's body, the disposal slider 53 that uses the spring 68 to bias the needle slider 52 in the opposite direction from the sensor insertion direction, and the puncture knob 46 that hits rear end of the needle slider 52 to push in the needle slider 52 in the sensor insertion direction. In a state in which the sensor supply unit 30 has been inserted into the sensor supply unit grip portion 48, the disposal slider 53 slides rearward in the puncture direction.

As a result, the spring 68 linking the needle slider 52 and the disposal slider 53 stores a biasing force corresponding to how far the disposal slider 53 has slid rearward from the initial position in the puncture direction before a puncture operation is performed with the needle 35. Thus, during a puncture operation with the needle 35, the distance which the puncture knob 46 pushes in the needle slider 52 is shorter. This makes the sensor unit insertion device 44 more convenient for the user to use.

The sensor unit insertion device 44 in this embodiment comprises the main body case 45, the needle slider 52 that is provided in the main body case 45 and is provided in a state in which it is able to slide in the direction in which the sensor 4 gripped at the front end is inserted under the skin, and the puncture knob 46 that hits the rear end of the needle slider 52 to push in the needle slider 52 in the sensor insertion direction. The sensor unit insertion device 44 is provided with a load mechanism (the plungers 56a and 56b) that apply a load from the pushing start position of the puncture knob 46 until it starts to move forward.

With this configuration, during a puncture operation with the needle 35, the puncture knob 46 will not move forward in the puncture direction unless it is pushed in with at least a specific amount of force, and once this specific amount of force is exerted, the puncture knob 46 is pushed in all at once. This makes it easy to adjust the force, so the sensor unit insertion device 44 is more convenient for the user to use.

The sensor supply unit 30 in this embodiment comprises the sensor main body 18, the sensor support body 16a that supports the sensor main body 18, the needle 35 for detachably inserting the sensor main body 18, the grip portion 34 serving as a needle support that fixes and supports the needle 35 and detachably supports the sensor support body 16a, and the support body 31 that supports the grip portion 34 serving as a needle support in a slidable state. The support body 31 is provided above with a head 31b serving as a grip portion for gripping the support body 31, and is provided below with an opening that allows the needle 35 to stick out.

With this configuration, the sensor supply unit 30 does not include the transmitter 7, and the opening that allows the needle 35 to stick out can be made smaller, so the needle 35 is easier for the user to see. This improves the convenience for a patient or other such user.

The sensor supply unit 30 in this embodiment comprises the sensor main body 18, the support body 16a that supports the sensor main body 18, the needle 35 for detachably inserting the sensor main body 18, the grip portion 34 serving as a needle support that fixes and supports the needle 35 and detachably supports the support body 16a, and the support body 31 that supports the grip portion 34 serving as a needle support in a slidable state.

With this configuration, since the constituent elements can be simplified, the sensor supply unit 30 can be used more conveniently by the user.

Preventing Reuse of Sensor Supply Unit

A configuration for preventing reuse of the sensor supply unit 30 will now be described as a way to make the sensor unit insertion device 44 more convenient to use, through reference to FIGS. 30A to 30E.

In order to make the explanation easier to understand, the explanation will be given using a conceptual diagram in which constituent elements such as the main body case 45 are omitted.

Figure 30:
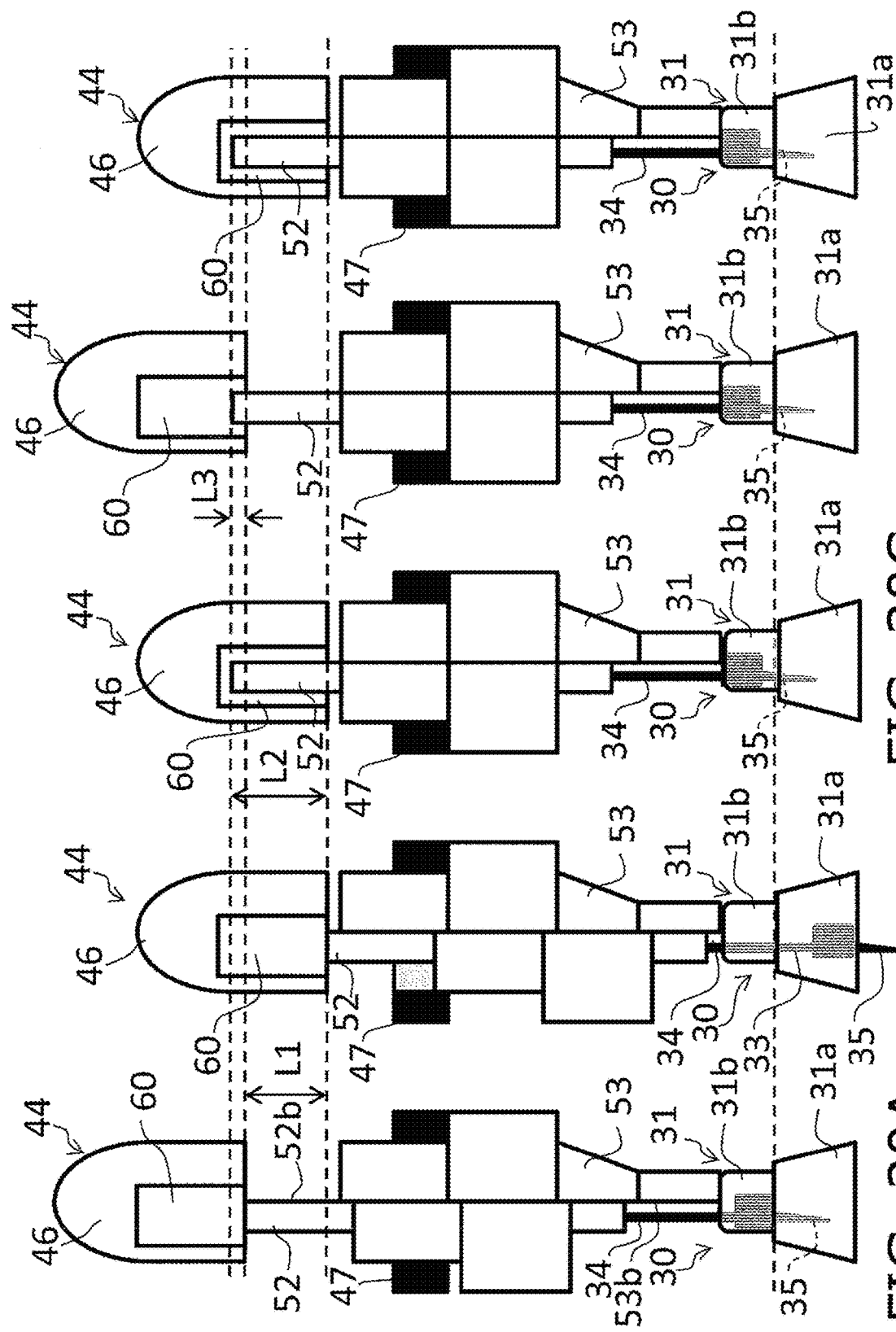
FIG. 30A is a cross section of the main part of the continuous glucose monitoring (CGM) device in FIG. 1.
FIG. 30B is a cross section thereof.
FIG. 30C is a cross section thereof.
FIG. 30D is a cross section thereof.
FIG. 30E is a cross section thereof.

FIGS. 30A and 30B show the puncture operation with the sensor unit insertion device 44.

In FIGS. 30A and 30B, the user pushes in the puncture knob 46 forward and slides it forward in the puncture direction, whereby the puncture knob 46 and the needle slider 52 that hits the rear end in the puncture direction (the opposite side from the puncture side) slide forward (forward in the puncture direction). As a result, as shown in FIG. 30B, the needle unit 33 of the sensor supply unit 30 slides forward while sliding over the open end of the support body 31.

That is, the needle unit 33 is held in a slidable state by the support body 31. Therefore, in a state in which the support body 31 is gripped at the front end portion of the sensor unit insertion device 44, the support body 31 is fixed to the sensor supply unit grip portion 48 of the sensor unit insertion device 44 (see FIG. 18A, etc.), and in this state, just the needle unit 33 is able to slide forward and backward in the puncture direction.

As a result, as shown in FIG. 30B, the needle 35 of the needle unit 33 protrudes forward in the puncture direction from the front opening of the support body 31.

FIG. 30B shows a state in which puncture with the needle 35 is complete. In this state, the needle 35 protrudes forward as far as it will go in the puncture direction.

FIG. 30C shows the removal of the needle 35.

The puncture operation was described above, but after the puncture operation, it is preferable to remove just the needle 35 quickly, leaving the sensor 4 under the skin of the upper arm 2.

FIGS. 30A and 30B show the state when the front end 55 of the puncture knob 46 is in contact with the rear end (second end) of the needle slider 52, and the needle slider 52 is pushed in the sensor insertion direction.

In FIG. 30B, the front end 55 of the puncture knob 46 (see FIG. 25A) is in contact with the rear end of the disposal slider 53. This contact state indicates that the needle slider 52 has slid a specific length in the insertion direction of the sensor 4.

In this case, if we let L1 be the length that the puncture knob 46 slides in the insertion direction of the sensor 4, and let L2 be the length that the needle slider 52 is inserted into the insertion hole 60 of the puncture knob 46, in this embodiment the length L1 is shorter than the length L2.

Consequently, as shown in FIG. 30D, even if the puncture knob 46 is pulled up to its upper limit position (above in the drawing), the rear end of the needle slider 52 is still held in the insertion hole 60 of the puncture knob 46. Consequently, in this state, as shown in FIG. 30E, the puncture knob 46 cannot hit the rear end of the needle slider 52 to push in the needle slider 52 in the puncture direction.

This is because the length L that the puncture knob 46 slides in the insertion direction of the sensor 4 is shorter than the length L2 that the needle slider 52 is inserted into the insertion hole 60 of the puncture knob 46. That is, in this state, even if the puncture knob 46 is pulled up, the rear end of the needle slider 52 remains inserted into the insertion hole 60 by a length L3, which is the difference between the length L1 and the length L2.

Specifically, the rear end (the second end) of the needle slider 52 is held in the insertion hole 60 of the puncture knob 46 until completion of the return operation of the insertion hole 60 from its open state to its closed state by the return mechanism from the completion of the puncture operation.

The opening mechanism comprises the window body 61 serving as a lid of the insertion hole 60 into which the rear end of the needle slider 52 is inserted, and the handle 63 for moving the lid to the open state upon hitting the rear end of the disposal slider 53. When the rear end portion of the needle slider 52 has been pulled out of the insertion hole 60, the window body 61 serving as a lid of the insertion hole 60 is biased in the direction of closing the insertion hole 60. On the other hand, when the rear end portion of the needle slider 52 is inserted in the insertion hole 60, the window body 61 serving as the lid comes into contact with the outer peripheral face of the needle slider 52 and cannot be closed, so it remains open. Therefore, the puncture knob 46 hits the rear end of the needle slider 52 and cannot slide and push in the needle slider 52 forward.

That is, in a state in which the sensor supply unit 30 has been used but is still mounted, the sensor supply unit 30 cannot be reused. As a result, safety during use is enhanced, so the sensor unit insertion device 44 is more convenient to use.

Next, a configuration for making the length L1 that the puncture knob 46 slides in the sensor insertion direction shorter than the length L2 that the needle slider 52 is inserted into the insertion hole 60 of the puncture knob 46 will be described.

Figure 31:
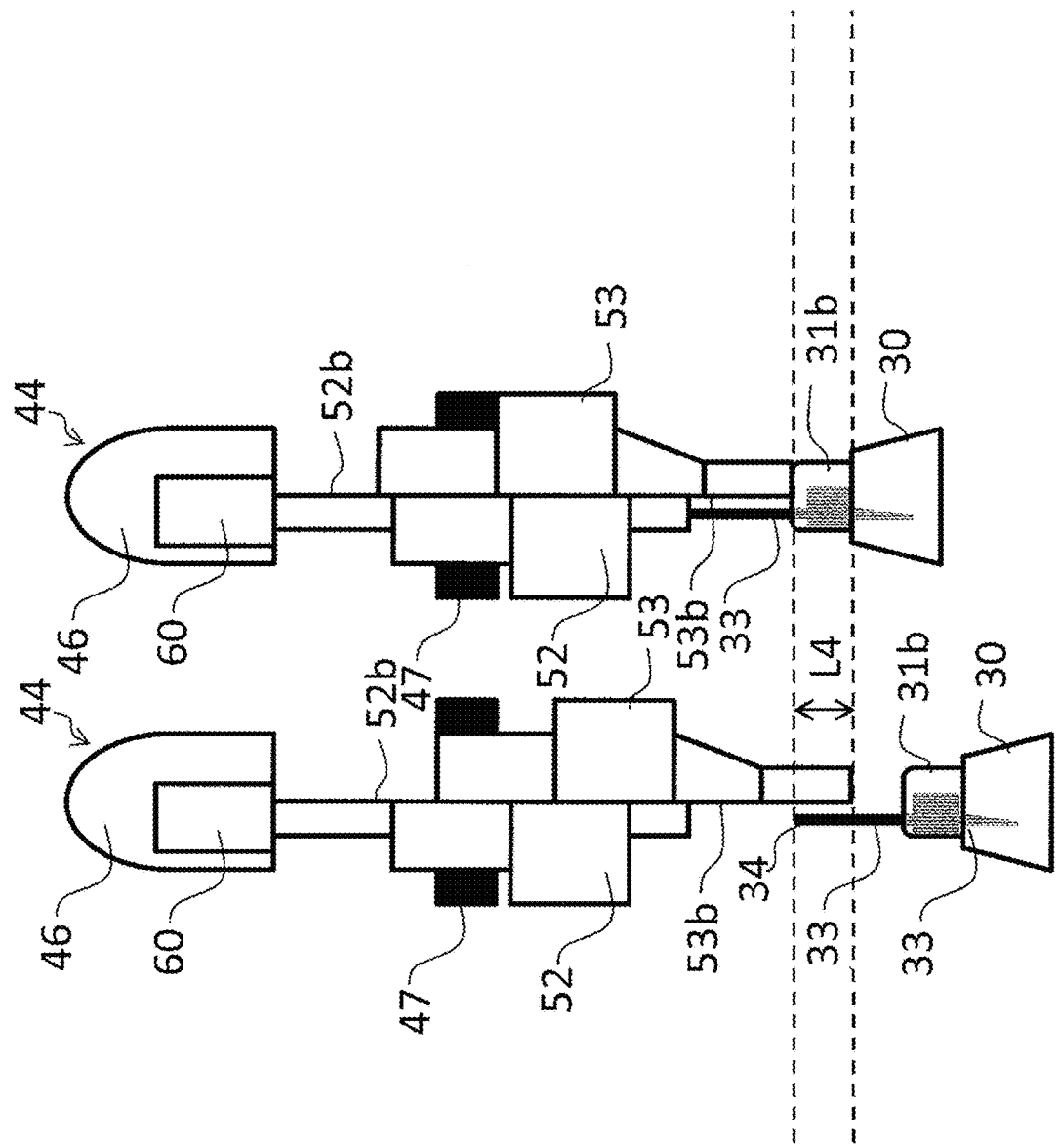
FIG. 31A is a cross section of the main part of the continuous glucose monitoring (CGM) device in FIG. 1.
FIG. 31B is a cross section thereof.

FIGS. 31A and 31B show the step of mounting the sensor supply unit 30 to the sensor unit insertion device 44.

FIG. 31A shows the state immediately before the front end portion of the sensor unit insertion device 44 is inserted into the sensor supply unit 30.

FIG. 31B shows the state when the sensor supply unit 30 has been mounted to the front end portion of the sensor unit insertion device 44.

In the step of mounting the sensor supply unit 30, first, the sensor supply unit 30 comes into contact with the front end of the disposal slider 53 and starts pushing up the disposal slider 53. Here, the needle slider 52 and the disposal slider 53 are connected by the spring 68 (see FIG. 34, etc.). Therefore, inserting the sensor supply unit 30 into the sensor unit insertion device 44 stretches out the spring 68 and charges it with a biasing force. Therefore, the disposal slider 53 is biased forward in the puncture direction with respect to the sensor supply unit 30.

In FIG. 31B, in a state in which a forward biasing force is applied to the disposal slider 53 in the puncture direction, the user further moves the disposal slider 53 so as to push in the disposal slider 53 with respect to the sensor supply unit 30.

Next, as shown in FIG. 31B, the grip portion 34 of the needle unit 33 of the sensor supply unit 30 hits the front end of the needle slider 52 and starts pushing up the needle slider 52.

Next, the rear end of the needle slider 52 hits the front end 55 of the puncture knob 46 (see FIG. 25A, etc.), resulting in a state in which the needle slider 52 cannot slide backward in the puncture direction. At this point, the grip portion 34 of the needle unit 33 is inserted into and mated with the front end of the needle slider 52. This completes the mounting of the sensor supply unit 30 to the sensor unit insertion device 44.

In this state, the sensor supply unit grip portion 48 of the sensor unit insertion device 44 (see FIG. 29, etc.) grips the head 31b of the support body 31 and holds down the blade portions of the engagement blades 33a and 33b of the needle unit 33 from the outside. Consequently, as described above, the unlatched needle 35 is able to slide forward, that is, can puncture the skin.

The grip portion 34 of the needle unit 33 of the sensor supply unit 30 is inserted into and mated with the opening at the front end of the needle slider 52. Therefore, the needle slider 52 does not move rearward in the puncture direction by this inserted length.

Meanwhile, the disposal slider 53 is in contact with the upper face of the head 31b of the sensor supply unit 30. The rear end of the disposal slider 53 does not hit the front end 55 of the puncture knob 46. Consequently, the disposal slider 53 slides rearward in the puncture direction by the amount that the sensor supply unit 30 was pushed into the sensor unit insertion device 44.

That is, the length L4 that the disposal slider 53 slides rearward in the puncture direction when the sensor supply unit 30 is mounted is longer than the distance that the needle slider 52 slides backward in the puncture direction.

In other words, when the sensor supply unit 30 is mounted, the length that the disposal slider 53 slides toward the rear of the puncture direction is longer than the length that the needle slider 52 slides in the puncture direction.

As a result, when the sensor supply unit 30 is mounted to the front end portion of the sensor unit insertion device 44, the spring 68 charged by the length L4 that the disposal slider 53 slides rearward in the puncture direction imparts to the needle slider 52 a biasing force for backward sliding movement in the puncture direction. This allows the biasing force required for the removal of the needle 35 after a puncture operation to be stored up in advance.

Accordingly, in a state in which the sensor supply unit 30 is mounted to the sensor unit insertion device 44, the rear end of the needle slider 52 is biased rearward in the puncture direction with respect to the front end 55 of the puncture knob 46. Consequently, the needle slider 52 moves further upward after the withdrawal of the needle 35 with respect to the position of the needle slider 52 when the sensor supply unit 30 was mounted.

As a result, the length L2 that the needle slider 52 is inserted into the insertion hole 60 of the puncture knob 46 is longer than the length L1 that the puncture knob 46 slides in the sensor insertion direction.

Consequently, in a state where the sensor supply unit 30 that has been used is mounted, the puncture knob 46 cannot push the needle slider 52 forward in the puncture direction. Therefore, the sensor supply unit 30 cannot be reused. As a result, safety is improved and convenience is also enhanced.

As described above, the sensor unit insertion device 44 in this embodiment comprises the main body case 45, the needle slider 52, the disposal slider 53, the spring 68, the puncture knob 46, and an opening mechanism (the window body 61 and the handle 63). The needle slider 52 grips the needle 35 and the sensor 4 on the first end side and is provided in the main body case 45 in a state of being able to slide in the sensor insertion direction. The disposal slider 53 is provided in the main body case 45 in a state of being able to slide parallel to the needle slider 52. The puncture knob 46 has the insertion hole 60 into which the rear end portion of the needle slider 52 can be inserted. The window body 61 and the handle 63 constituting the opening mechanism close off the insertion hole 60 when the needle slider 52 is slid a specific length in the sensor insertion direction, and when puncture by the needle 35 is complete, the contact portion between the second end of the needle slider 52 and the puncture knob 46 is opened up, and the second end of the needle slider 52 is inserted into the insertion hole 60.

Consequently, when puncture by the needle 35 is complete, the rear end portion of the needle slider 52 has been inserted into the insertion hole 60 by the opening mechanism. Therefore, even if an attempt is made to push the puncture knob 46 forward in the puncture direction again, the needle 35 is prevented from protruding.

Therefore, the user is prevented from reusing the used needle 35 with which a puncture operation has already been performed. As a result, the user safety is enhanced and the device is more versatile.

Also, the puncture knob 46 hits the rear end of the needle slider 52 and slides and pushes in the needle slider 52 in the sensor insertion direction. Furthermore, when the puncture knob 46 slides the needle slider 52 a specific length in the sensor insertion direction, the contact portion of the rear end of the needle slider 52 is opened up by the opening mechanism, and the rear end portion of the needle slider is inserted into the insertion hole 60. The length L1 that the puncture knob 46 slides in the insertion direction of the sensor 4 is shorter than the length L2 that the needle slider is inserted into the insertion hole 60 of the puncture knob 46.

Consequently, even if the puncture knob 46 is slid to its upper limit position as shown in FIG. 30D after the withdrawal of the needle 35 shown in FIG. 30C, the rear end of the needle slider 52 remains inserted in the insertion hole 60 by the length L3 (=L2−L1).

Thus, even if the puncture knob 46 is pulled up to its upper limit position, the rear end of the needle slider 52 does not come out of the insertion hole 60 of the puncture knob 46. Therefore, in this state, as shown in FIG. 30E, the puncture knob 46 hits the rear end of the needle slider 52 and cannot be slid forward and pushed in.

That is, in a state in which the sensor supply unit 30 that has been used is left mounted, the sensor supply unit 30 cannot be reused. This improves safety and also improves convenience.

As shown in FIGS. 31A and 31B, the sensor unit insertion device 44 in this embodiment is such that the length L4 that the disposal slider 53 slides rearward in the puncture direction when the sensor supply unit 30 is mounted is longer than the length that the needle slider 52 slides rearward in the puncture direction when the sensor supply unit 30 is mounted.

Consequently, in the mounting of the sensor supply unit 30, the rear end of the needle slider 52 further biases the front end 55 of the puncture knob 46 rearward in the puncture direction. Therefore, the needle slider 52 moves further upward after the removal of the needle 35, with respect to the position of the needle slider 52 at the time of mounting the sensor supply unit 30.

Therefore, the length L2 of the needle slider 52 inserted into the insertion hole 60 of the puncture knob 46 is longer than the length L1 that the puncture knob 46 slides in the sensor insertion direction.

As a result, in a state in which the sensor supply unit 30 that has been used is left mounted, the sensor supply unit 30 cannot be reused. This prevents a used needle 35 from being used twice, so safety and convenience are better than in the past.

Reuse of Sensor Unit Insertion Device

The sensor unit insertion device 44 in this embodiment uses the return mechanism described below (the elastic body 62 (or the elastic body 66)) to return from a state in which reuse is prevented by the opening mechanism after a puncture operation, to a state in which a new sensor supply unit 30 is installed and reuse (a puncture operation) is once again possible.

After the puncture knob 46 is pushed in to the puncture position and a puncture operation with the needle 35 of the needle slider 52 is complete, the return mechanism (the elastic body 62 (or the elastic body 66)) moves the puncture knob 46 to the opposite side from the sensor insertion direction, whereupon the open state of the insertion hole 60 is changed to a closed state.

FIGS. 32A to 32E show the steps of detaching the sensor supply unit 30 from the sensor unit insertion device 44.

Figure 32:
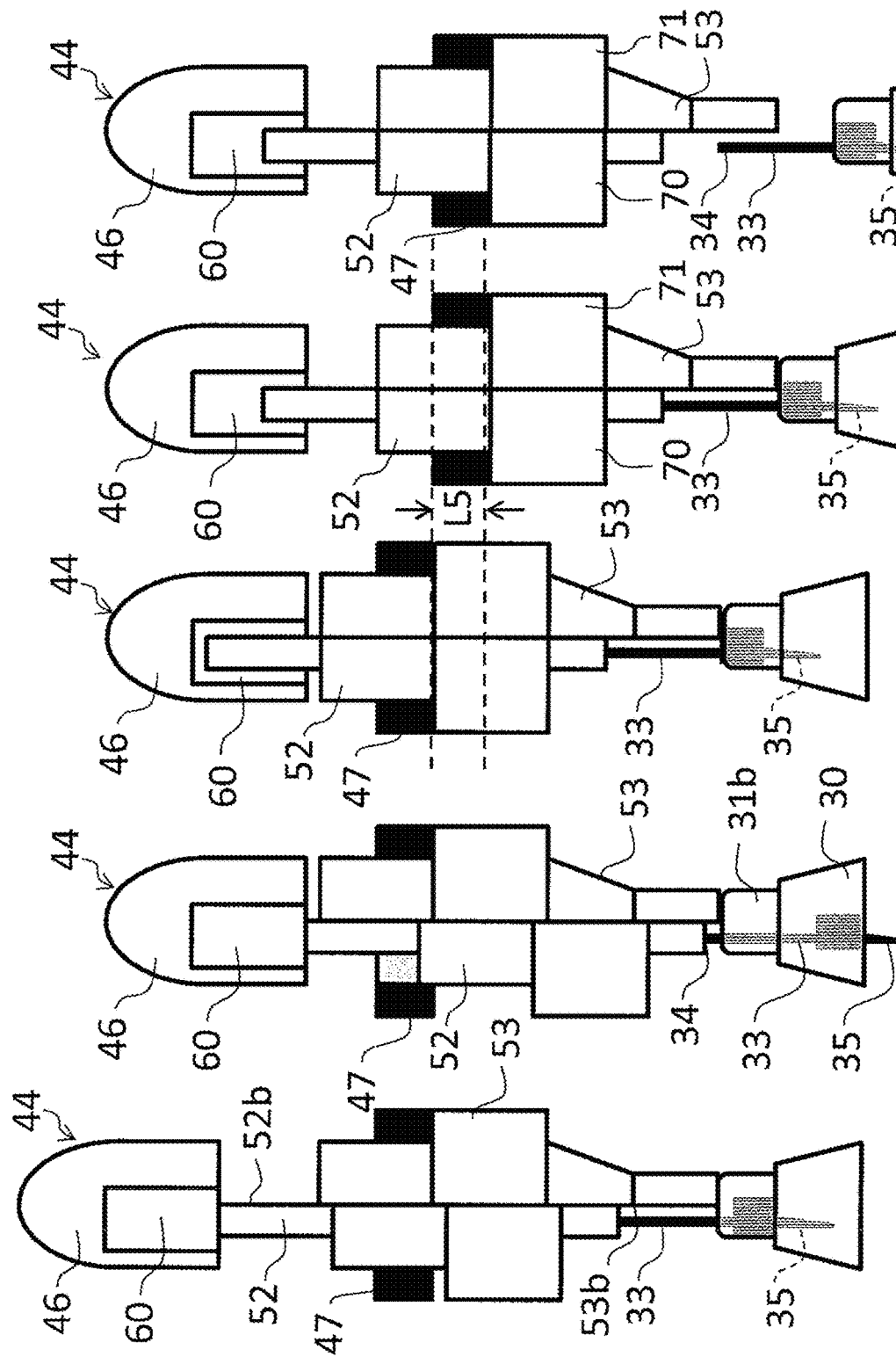
FIG. 32A is a cross section of the main part of the continuous glucose monitoring (CGM) device in FIG. 1.
FIG. 32B is a cross section thereof.
FIG. 32C is a cross section thereof.
FIG. 32D is a cross section thereof.
FIG. 32E is a cross section thereof.

FIGS. 32A and 32B show the puncture operation with the sensor unit insertion device 44 as described above.

FIG. 32C shows the removal of the needle 35 as described above.

FIG. 32D shows a state in which the disposal knob 47 is pushed forward in the puncture direction, so that the disposal knob 47 engages with an engagement component 70 on the outer edge of the needle slider 52 and an engagement component 71 on the outer edge of the disposal slider 53 and simultaneously depresses both so that the sensor supply unit 30 begins to be ejected.

FIG. 32D shows a state in which the disposal knob 47 has been completely pushed out forward in the puncture direction, but in this state the grip portion 34 of the needle unit 33 of the sensor supply unit 30 is mated to the front end of the needle slider 52, so the sensor supply unit 30 does not fly directly out.

FIG. 32E shows a state in which the user has pulled out the sensor supply unit 30 with his hand and detached it, and disposal is complete.

As shown in FIGS. 32C and 32D, we will let L5 be the length that the disposal knob 47 slides the needle slider 52 and the disposal slider 53 in the sensor insertion direction when it engages with the engagement component 70 on the outer edge of the needle slider 52 and the engagement component 71 on the outer edge of the disposal slider 53.

As described above, L3 is the difference between the length L1 that the puncture knob 46 slides in the sensor insertion direction and the length L2 that the needle slider 52 is inserted into the insertion hole 60 of the puncture knob 46.

In this embodiment, the length L5 that the disposal knob 47 slides the needle slider 52 in the sensor insertion direction is longer than the length L3 that is difference between the lengths L1 and L2.

Consequently, after the sensor supply unit 30 has been removed from the sensor unit insertion device 44, the puncture knob 46 is returned rearward in the puncture direction by the length L1, resulting in a state in which the opening/closing part (the window body 61 or the window body 65) of the lid of the insertion hole 60 has closed the lid at the same time the rear end portion of the needle slider 52 comes out of the insertion hole 60.

As a result, the puncture knob 46 hits the rear end of the needle slider 52, which results in a change back to a state in which it can slide forward, and the needle slider 52 can be pushed in.

Figure 33:
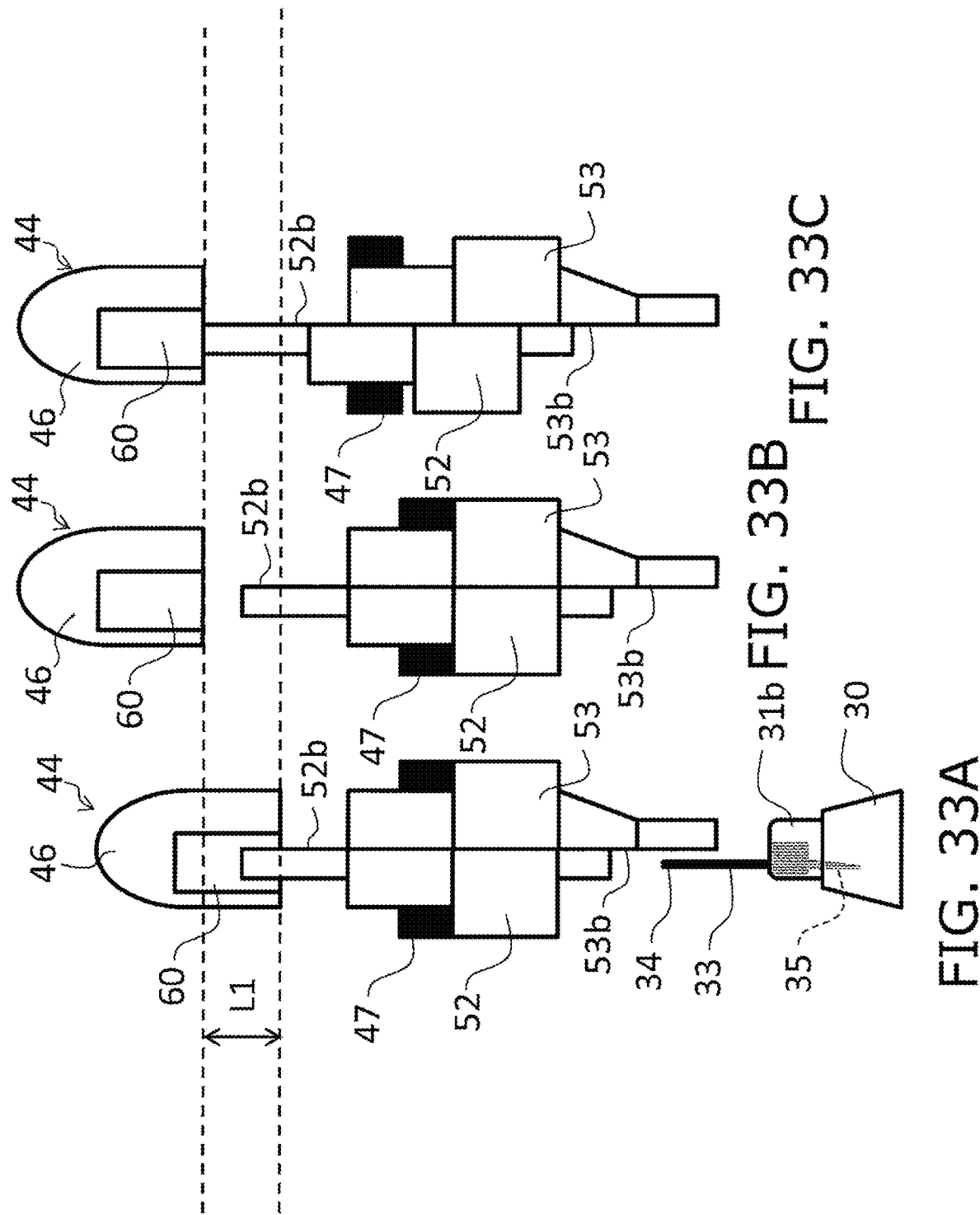
FIG. 33A is a cross section of the main part of the continuous glucose monitoring (CGM) device in FIG. 1.
FIG. 33B is a cross section thereof.
FIG. 33C is a cross section thereof.

FIGS. 33A to 33C show the steps of initializing the sensor unit insertion device 44 when the sensor supply unit 30 is detached from the sensor unit insertion device 44.

FIG. 33A shows the same state as FIG. 32E, and is a state in which the disposal knob 47 has been completely pushed out forward in the puncture direction, and the user has grasped and pulled out the sensor supply unit 30 by hand, which completes the removal of the sensor supply unit 30.

FIG. 33B shows a state in which the puncture knob 46 has been returned to the rear in the puncture direction by the length L1, and has been returned to its position in the initial state. At this point, the rear end portion of the needle slider 52 comes out of the insertion hole 60, so the opening/closing part (the window body 61 or the window body 65) of the lid of the insertion hole 60 is put back into its closed state by the biasing force produced by the elastic body 62 (or the elastic body 66). As a result, the puncture knob 46 is brought into a state in which it can hit the rear end of the needle slider 52, so the puncture knob 46 slides forward and enters a state in which a puncture operation can be performed, in which the needle slider 52 can be pushed in again.

In FIG. 33C, the needle slider 52 and the disposal slider 53 are returned to their initial state in which the sensor supply unit 30 can be attached, by returning the disposal knob 47 to the rear side in the puncture direction.

That is, with this configuration, a new sensor supply unit 30 is mounted to the front end portion of the sensor unit insertion device 44 so that the sensor 4 can be inserted under the skin.

This allows the sensor unit insertion device 44 to be put in a reusable state. Also, after the sensor supply unit 30 has been used, the sensor unit insertion device 44 cannot be used again unless the sensor supply unit 30 is removed. This improves safety and also enhances convenience.

The sensor unit insertion device 44 in this embodiment comprises the main body case 45 and the needle slider 52 that is provided in the main body case 45, grips the sensor 4 at the front end, and is provided in a state of being able to slide in the direction of inserting the sensor 4 into the patient's body. The sensor unit insertion device 44 further comprises the spring 68 that biases the disposal slider 53 in the opposite direction from the insertion direction of the sensor 4 (forward in the puncture direction) with respect to the needle slider 52.

Furthermore, the sensor unit insertion device 44 comprises the puncture knob 46 that hits the rear end of the needle slider 52 and slides in the insertion direction of the sensor 4 to push in the needle slider 52. The sensor unit insertion device 44 comprises an opening mechanism that opens up the contact portion with the rear end of the needle slider 52 and opens up the opening side of the insertion hole 60 into which the rear end portion of the needle slider 52 is inserted, when the needle slider 52 slides a specific length in the insertion direction of the sensor 4.

When the rear end portion of the needle slider 52 inserted into the insertion hole 60 formed on the front side of the puncture knob 46 in the puncture direction is pulled out of the insertion hole 60, the return mechanism puts the opening side of the insertion hole 60 back into a closed state by means of the elastic force of the elastic body 62 (or the elastic body 66).

Consequently, after a puncture operation of inserting the sensor 4 into the patient's body, the needle slider 52 is slid forward in the puncture direction by the disposal knob 47, which moves the puncture knob 46 in the direction in which the rear end (second end) of the needle slider 52 is pulled out of the insertion hole 60 of the puncture knob 46. The puncture knob 46 is then slid rearward in the puncture direction (upward in FIG. 33B), resulting in a state in which the rear end portion of the needle slider 52 has come out of the insertion hole 60.

At this point, the elastic body 62 (or the elastic body 66) constituting the return mechanism is constantly imparting an elastic force in the direction in which the window body 61 (or the window body 65) constituting the opening mechanism puts the insertion hole 60 in its closed state. Consequently, at the same time that the rear end portion of the needle slider 52 comes out of the insertion hole 60, the window body 61 (the window body 65) slides (or rotates) to close the insertion hole 60, which puts the insertion hole 60 in its closed state.

As a result, the insertion hole 60 of the puncture knob 46 is changed to its closed state, and the window body 61 (or the window body 65) and the rear end portion of the needle slider 52 can come into contact with each other. Therefore, the puncture knob 46 can push in the needle slider 52 again to create a state in which puncture is possible, so the sensor unit insertion device 44 can be put in a reusable state.

As shown in FIGS. 30A and 30B, the length L1 that the puncture knob 46 slides in the insertion direction of the sensor is shorter than the length L2 that the needle slider 52 is inserted into the insertion hole 60 of the puncture knob 46. The length L5 that the disposal knob 47 shown in FIG. 32D slides the needle slider 52 in the sensor insertion direction is longer than the length L3 (see FIG. 30D) that is the difference between the length L2 that the needle slider 52 is inserted into the insertion hole 60 and the length L1 that the puncture knob 46 slides in the sensor insertion direction.

Consequently, as shown in FIG. 30D, after the needle 35 shown in FIG. 30C has been pulled out, in a state in which the puncture knob 46 has been slid upward in FIGS. 30A to 30E (rearward in the puncture direction), the rear end of the needle slider 52 is still inserted in the insertion hole 60 by the length L3 (=L2−L1).

With the sensor unit insertion device 44 in this embodiment, if the length L5 that the disposal knob 47 slides the needle slider 52 in the sensor insertion direction is longer than the length L3, the rear end portion of the needle slider 52 will be in a state of having been pulled out of the hole 60.

Therefore, the insertion hole 60 of the puncture knob 46 is put in its closed state by the window body 61 (or the window body 65) that is subjected to the elastic force of the elastic body 62 (or the elastic body 66) provided as the return mechanism, so the rear end of the needle slider 52 is in a state in which it can hit the front end (the window body 61 or the window body 65) of the puncture knob 46 again without being inserted into the insertion hole 60.

As a result, the puncture knob 46 can hit the rear end portion of the needle slider 52 and can return to the initial state in which a puncture operation can be performed again. That is, the return mechanism can restore the initial state in which the puncture knob 46 can be slid forward in the puncture direction to push in the needle slider 52, making puncture possible. Consequently, if a sensor supply unit 30 including an unused needle 35 is installed again, the sensor unit insertion device 44 can be made reusable.

Embodiment 2

The configuration of the biosensor according to another embodiment of the present invention will now be described through reference to FIGS. 36A to 47.

Those components that are share with the above embodiment will be numbered the same and will not be described in detail again.

Configuration of Biosensor

FIG. 36A is a top view of the sensor main body 18, and FIG. 36B is a bottom view.

The sensor main body 18 is constituted by a sensor insertion component 80 that is inserted into the patient's body, and a sensor connector 81 provided with a terminal for connecting electrical signals sent from the sensor insertion component 80.

The sensor insertion component 80 is covered with a protective film 82. The sensor connector 81 is provided with a reference electrode connecting terminal 83 and a working electrode connecting terminal 84 on the upper face, and is provided with a counter electrode connecting terminal 85 on the lower face. Portions other than these terminals are covered with a resist film 86, which is a nonconductive insulating film.

Sensor Manufacturing Steps

FIGS. 37A to 37D, FIGS. 38A to 38D, and FIGS. 39A to 39D show the steps for manufacturing the sensor main body 18.

In the step shown in FIG. 37A, a substrate 87 is formed from PET (polyethylene terephthalate), which is a resin material. Then, a gold film is deposited on the substrate 87 by sputtering in the step shown in FIG. 37B, and a gold electrode 88 is formed.

In the steps shown in FIGS. 37C and 37D, a gold electrode 88 is likewise formed on the lower face of the substrate 87.

Figures 38A, 38B, 38C, 38D:
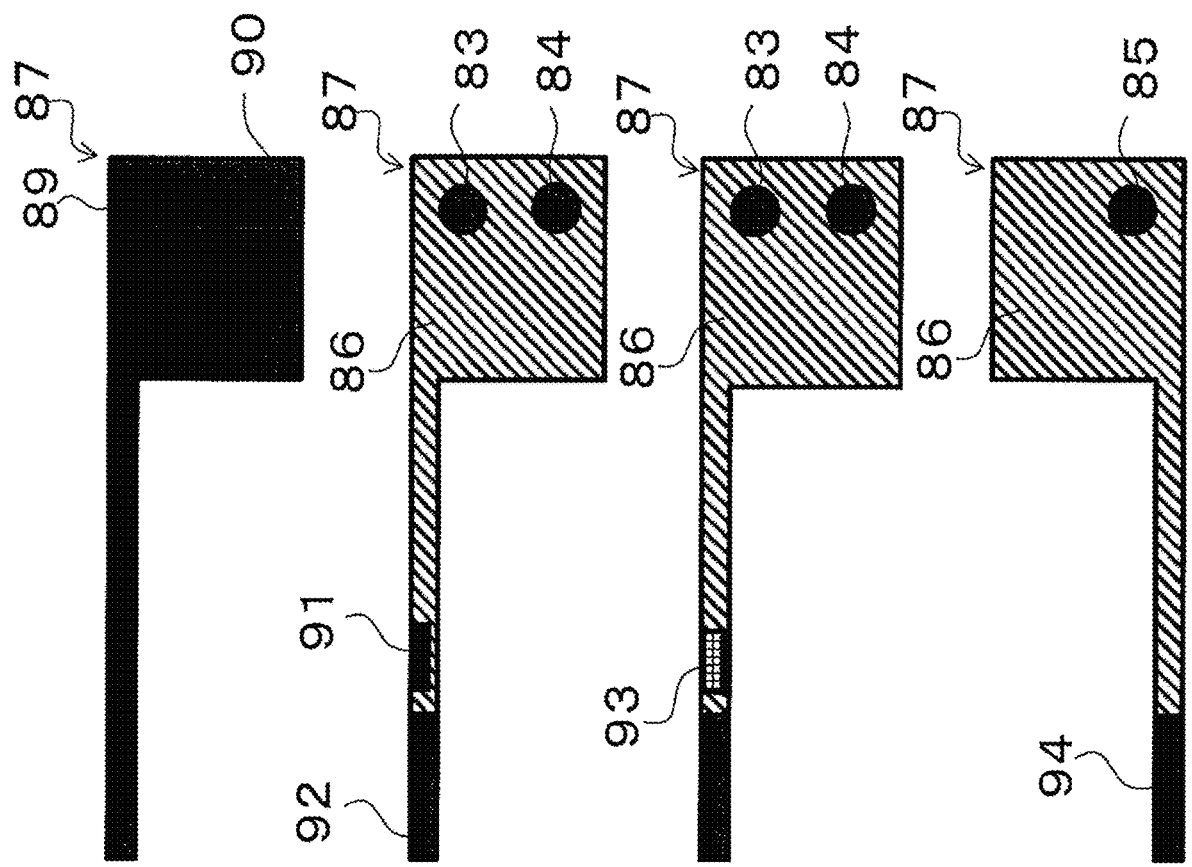
FIG. 38 is a diagram of the steps for manufacturing the sensor main body in FIG. 36A.

In the step shown in FIG. 38A, the gold electrode 88 on the upper face of the substrate 87 is divided by laser scribing to form a reference electrode conductor 89 and a working electrode conductor 90.

In the step shown in FIG. 38B, the resist film 86 is formed by screen printing or the like everywhere except in a reference electrode forming region 91 and the regions of a working electrode 92, the reference electrode connecting terminal 83, and the working electrode connecting terminal 84.

In the step shown in FIG. 38C, silver/silver chloride is formed in the reference electrode forming region 91 to form a reference electrode 93.

In the step shown in FIG. 38D, the resist film 86 is formed on the lower face except for in the regions of a counter electrode 94 and the counter electrode connecting terminal 85.

Figure 39A:
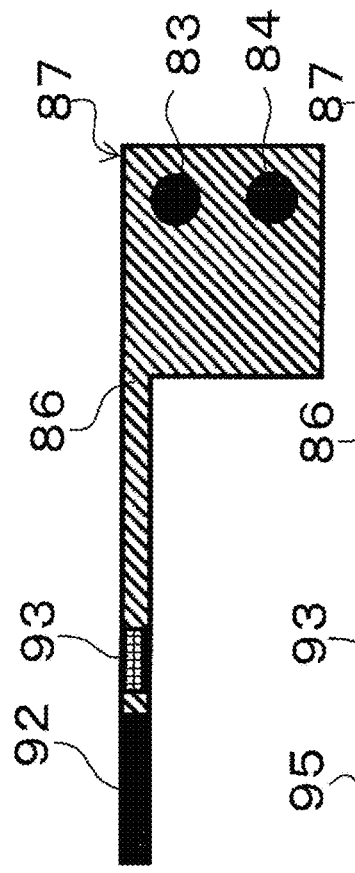
FIG. 39 is a diagram of the steps for manufacturing the sensor main body in FIG. 36A.
Figure 39B:
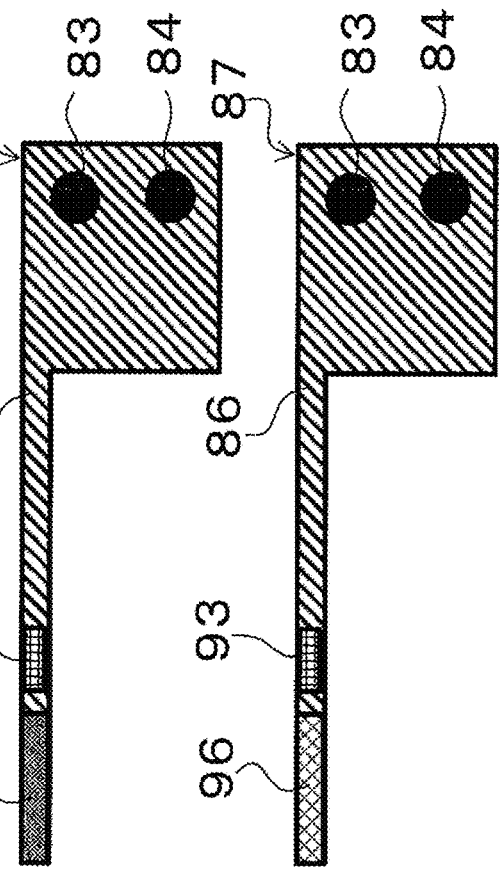

In the step shown in FIG. 39A, the surface of the working electrode 92 is coated with 0.3 uL of a mediator solution to form the mediator layer 95 shown in FIG. 39B.

More specifically, 5 mg/mL ruthenium complex, 5 mg/mL poly-L-lysine, 0.125% polyethylene glycol diglycidyl ether (made by Sigma-Aldrich), 0.125% glutaraldehyde (made by Wako Pure Chemical Industries), and 10 mM (pH 7.5) potassium phosphate buffer (made by Wako Pure Chemical Industries) are prepared as the mediator solution, and 0.3 μL of this solution was fixed to the working electrode surface.

Figure 39C:
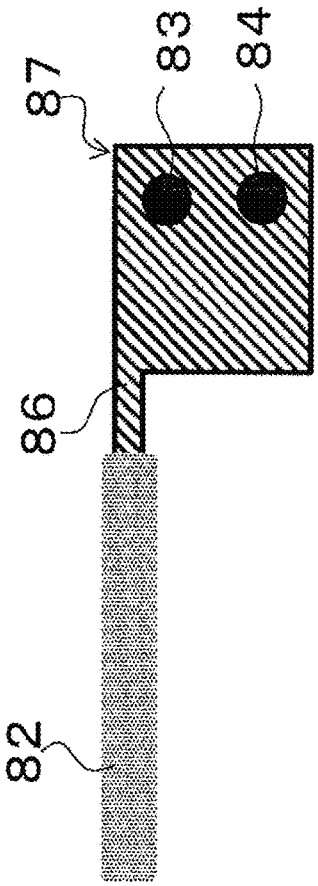

In the step shown in FIG. 39C, the mediator layer 95 shown in FIG. 39B is coated with 0.3 μL of an enzyme solution containing sodium polyacrylate, to form an enzyme layer 96.

More specifically, 25 mg/mL glucose oxidase (from *Aspergillus niger*; made by Sigma-Aldrich) and 0.001% sodium polyacrylate (made by Wako Pure Chemical Industries), were prepared, and 0.3 uL of enzyme solution was fixed on the mediator layer 95.

Sodium polyacrylate can be used as an additive in the enzyme layer 96, but trehalose and glucomannan can also be used as additives.

Figure 39D:
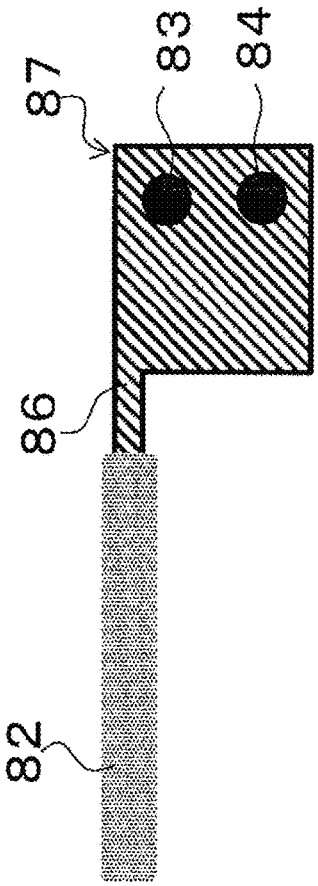
Figure 40A:
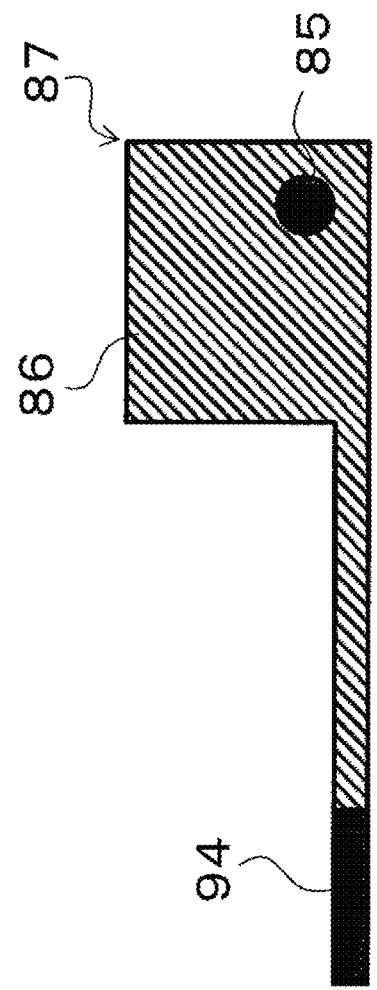
FIG. 40 is a diagram of the steps for manufacturing the sensor main body in FIG. 36A.
Figure 40B:
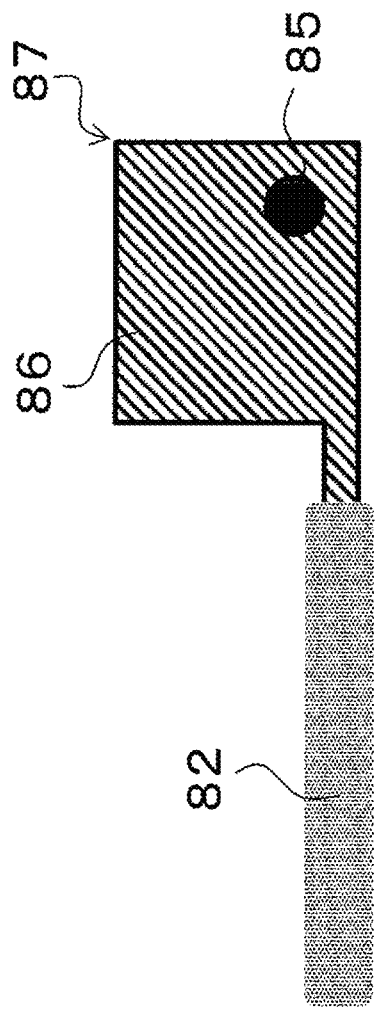

In the step shown in FIG. 39D, the substrate 87 on which the enzyme layer 96 has been formed is dipped in a poly-4-vinylpyridine solution to form the protective film 82.

More specifically, the protective film 82 is formed by dipping a sensor in 4% poly-4-vinylpyridine (ethanol solvent) (made by Sigma-Aldrich) and drying the coating. This treatment is performed six times to form a six-ply protective film 82. The protective film 82 on the lower face is also formed at the same in the steps shown in FIG. 40A and FIG. 40B.

Sensor Configuration

Figure 41A:
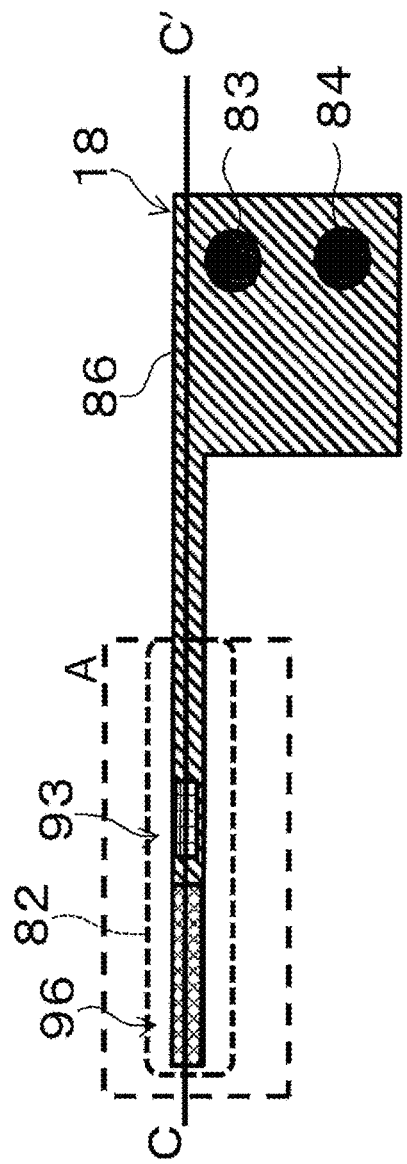
FIG. 41A is a top view of the sensor main body in FIG. 36A.
Figure 41B:
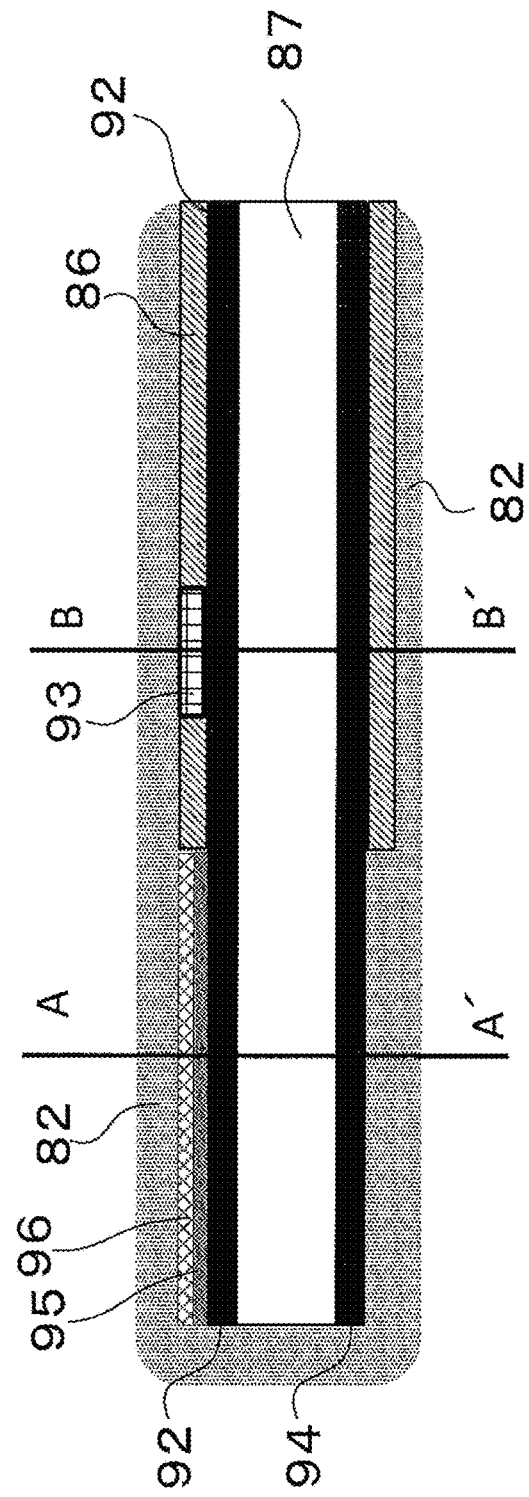
FIG. 41B is a cross section along the C-C' line in FIG. 41A.

FIG. 41A is a top view of the sensor main body 18. In this drawing, for ease of explanation, the protective film 82 is indicated by a dotted line. FIG. 41B is a vertical section along the C-C' line of the portion indicated by the box A.

Figure 42:
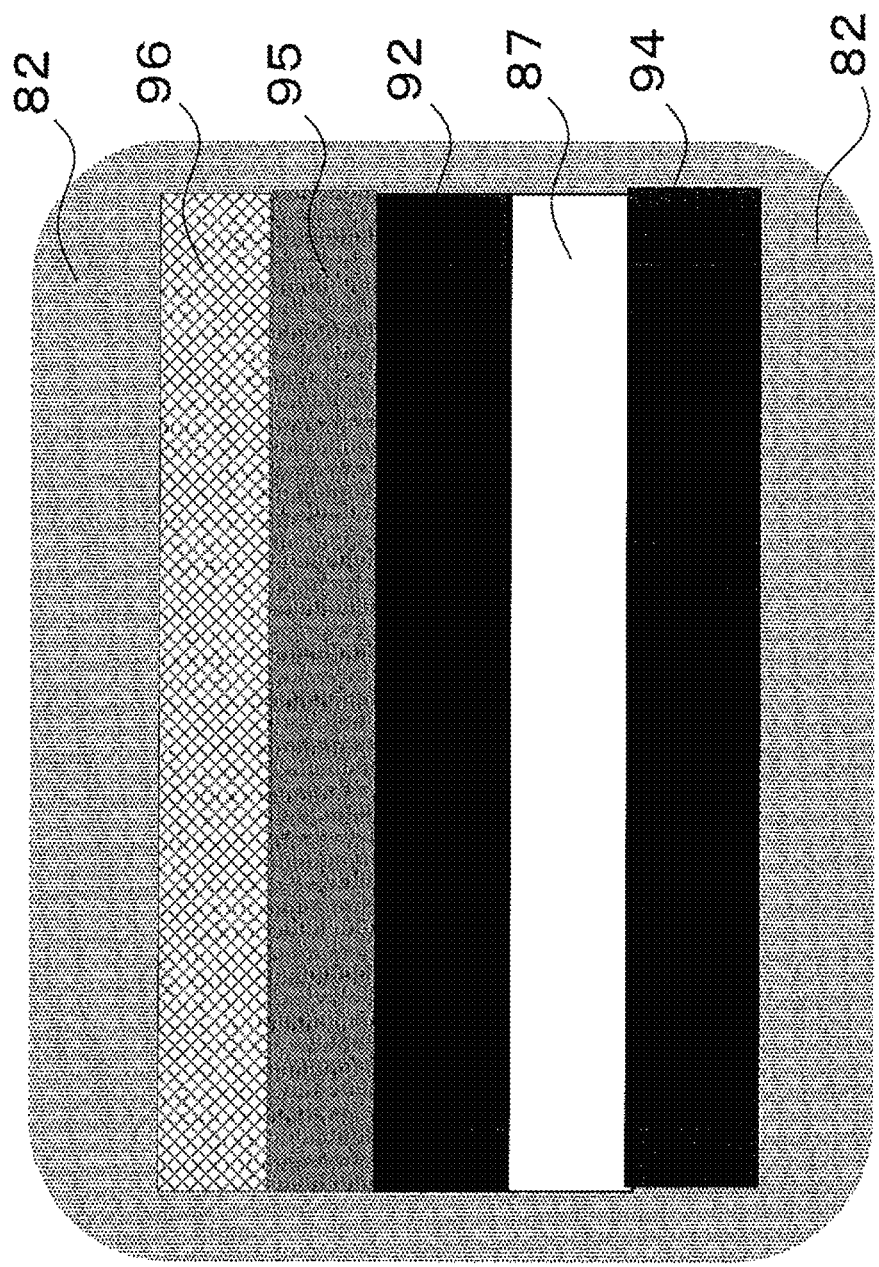
FIG. 42 is a cross section along the A-A' line in FIG. 41B.

FIG. 42 is a lateral cross section along A-A' line in FIG. 41B.

As shown in FIG. 42, in the A-A' cross section, the substrate 87 formed from PET (polyethylene terephthalate; a resin material) is disposed in the center. The working electrode 92 formed by a gold electrode as an electrode layer, the mediator layer 95, the enzyme layer 96 to which sodium polyacrylate has been added, and the protective film 82 are formed in that order above the substrate 87.

The counter electrode 94 formed by a gold electrode, and the protective film 82 are formed in that order as electrode layers under the substrate 87 in the A-A' cross section.

Figure 43:
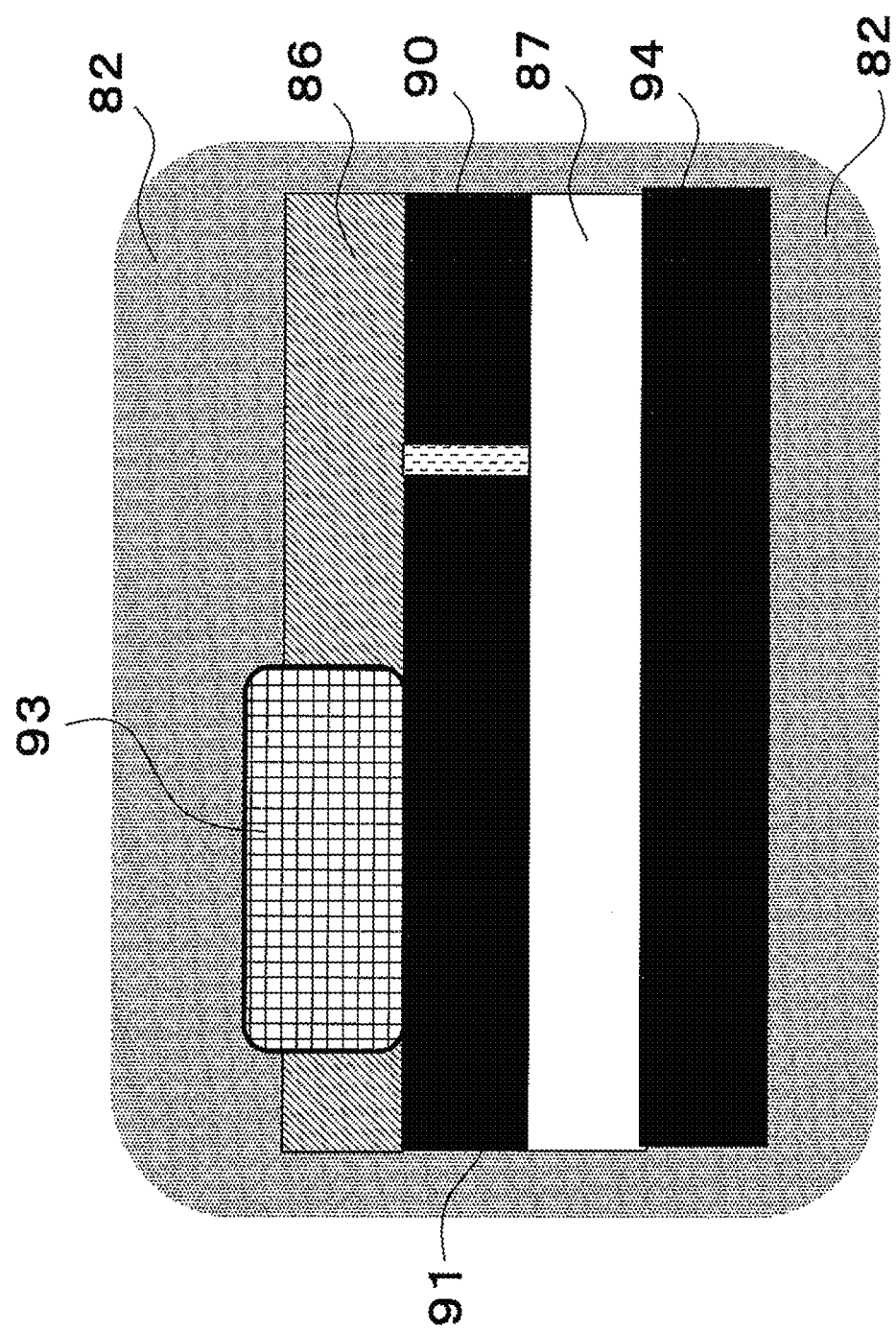
FIG. 43 is a cross section taken along line BB' in FIG. 41B.

FIG. 43 is a lateral cross section along the B-B' line in FIG. 41B.

As shown in FIG. 43, the substrate 87 formed of PET (polyethylene terephthalate; a resin material) is disposed in the center in the B-B' cross section. The working electrode 92 formed by a gold electrode as an electrode layer, the reference electrode 93 formed by a silver/silver chloride electrode similarly as an electrode layer, the resist film 86, and the protective film 82 are formed in that order above the substrate 87.

On the side of the working electrode conductor 90 divided by the laser (the right side in the drawing), the working electrode conductor 90 formed by a gold electrode as an electrode layer, the resist film 86, and the protective film 82 are formed in that order above the substrate 87.

The counter electrode 94 formed by a gold electrode and the protective film 82 are formed in that order below the substrate 87 in the B-B' cross section.

In this embodiment, ruthenium is used as the electron acceptor of the mediator layer 95, but ferrocene, osmium, cobalt, and vanadium can also be selected.

In this embodiment, glucose oxidase is used as the enzyme of the enzyme layer 96, but glucose dehydrogenase can also be selected.

In this embodiment, gold is used as the electrode material of the electrode layer, but platinum, platinum black, palladium, and carbon can also be selected.

Sensor Measurement Principle

Figure 44:
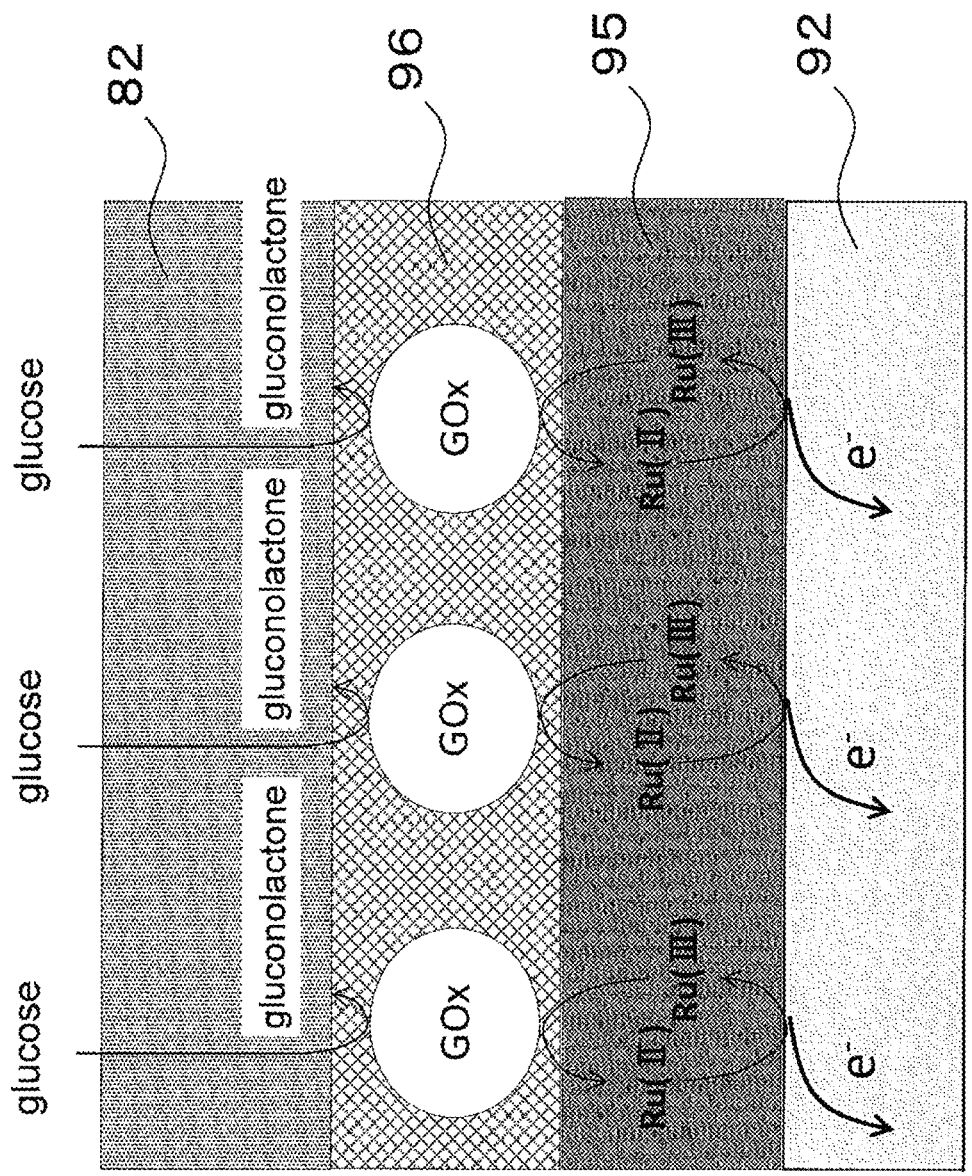
FIG. 44 shows the measurement principle of the sensor in FIG. 36A.

FIG. 44 shows the measurement principle of the sensor.

FIG. 44 is a detail view of the working electrode 92 from above, taken along the A-A' line in FIG. 41B.

The protective film 82 contains poly-4-vinylpyridine and limits the permeation of glucose in the interstitial fluid.

The enzyme layer 96 contains an oxidase or a dehydrogenase. More specifically, it contains glucose oxidase or glucose dehydrogenase. In this embodiment, glucose oxidase is used.

The mediator layer 95 contains an electron acceptor. In this embodiment, the mediator layer 95 uses a ruthenium complex (trivalent) as an electron acceptor.

The enzyme layer 96 is in contact with the mediator layer 95, and the mediator layer 95 is provided on the surface of an electrode.

The glucose measurement principle in this configuration will now be described.

First, the glucose in the subcutaneous interstitial fluid permeates the protective film 82 and reaches the enzyme layer 96. Next, glucose is oxidized to produce gluconolactone, and at the same time, in the mediator layer 95, the ruthenium complex (trivalent) fixed to the electrode is reduced to a ruthenium complex (divalent).

Then, the electrons when the reduced ruthenium complex (divalent) is oxidized on the surface of the gold electrode at the working electrode 92 are measured as the current value.

The enzyme layer 96 is in contact with the mediator layer 95, and the mediator layer 95 is provided on the surface of the electrode.

Consequently, the ruthenium complex (trivalent), which is an electron acceptor, is to reduced at the interface between the enzyme layer 96 and the mediator layer 95 by the enzyme (glucose oxidase) that has reacted with the glucose (substrate) and can instantly act as a reduced ruthenium complex (divalent).

Then, the reduced ruthenium complex (divalent) is oxidized into a ruthenium complex (trivalent) at the interface between the mediator layer 95 and the working electrode 92, and the electrons emitted from the ruthenium complex (divalent) at that time can be measured as a current value. This current value corresponds to the glucose concentration.

Experiment Result 1: Addition of Sodium Polyacrylate to Enzyme Layer

Figure 45:
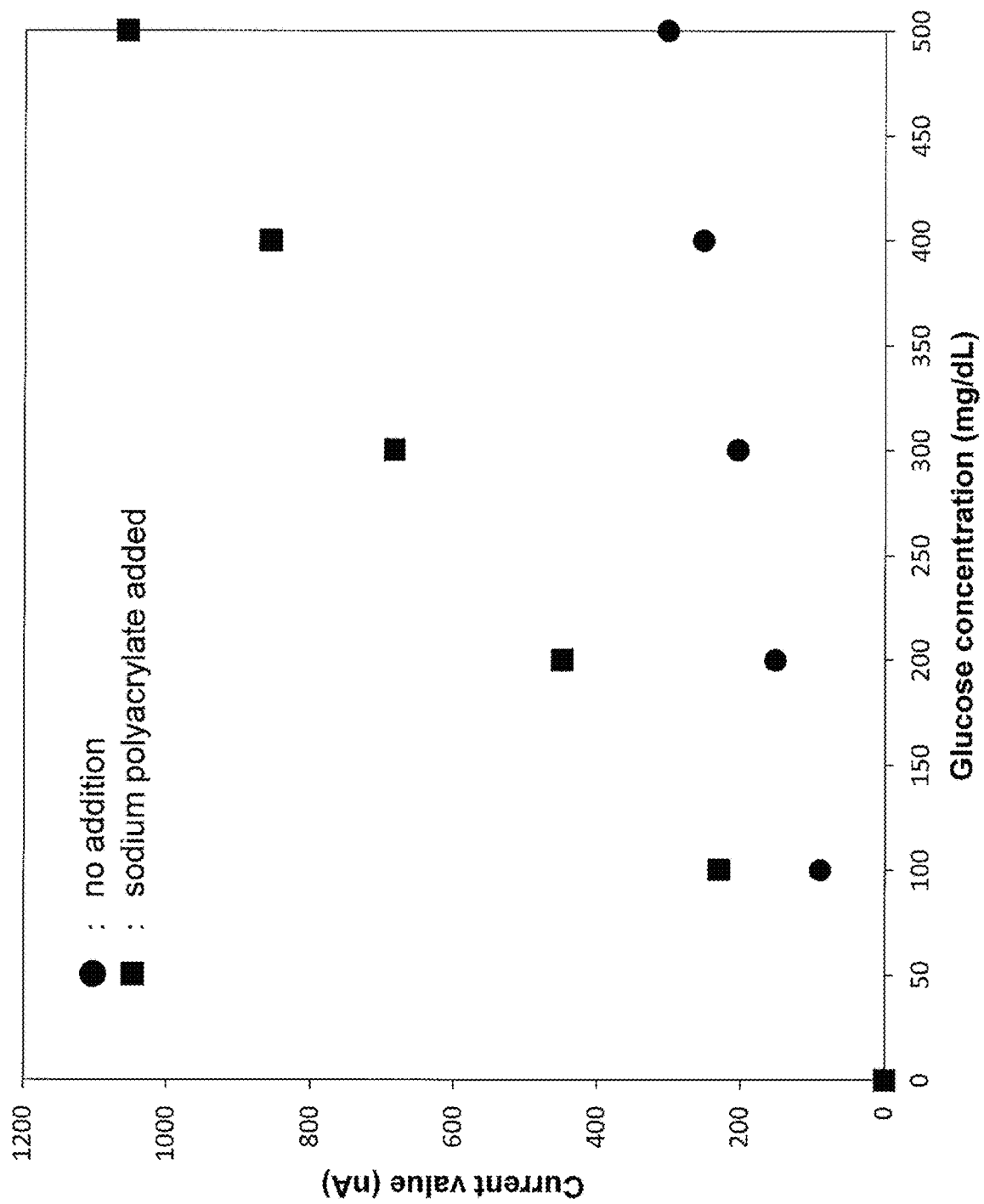
FIG. 45 is a diagram of an experiment result 1.

FIG. 45 shows the result of examining the change in the response current flowing to the sensor when the glucose concentration is varied in order to confirm how well the measurement sensitivity of the biosensor was improved in this embodiment.

In the experiment, a working electrode in which sodium polyacrylate was added and fixed to an enzyme (as an enzyme layer), a silver/silver chloride electrode (as a reference electrode), and a counter electrode were immersed in physiological saline, the glucose concentration contained in the physiological saline was measured at an application potential of 1.1 V (versus the silver/silver chloride), and the relation between the glucose concentration and the response current was evaluated.

Batch amperometry was used to measure the response current.

Glucose was added to a phosphate buffer solution in amounts of 100 mg/dL, 200 mg/dL, 300 mg/dL, 400 mg/dL, and 500 mg/dL, and the current value 10 minutes after the addition was taken as the measurement value.

As a comparative example, the same experiment was conducted using a sensor in which nothing was added to the enzyme layer.

The measured current value (nA) was plotted on the Y axis, and the glucose concentration (mg/dL) was plotted on the X axis, the result being that the response of the glucose sensor was about four times better with the sensor in which sodium polyacrylate was added in an amount of 0.001%.

This proves that adding sodium polyacrylate to the enzyme layer improves the sensitivity of the biosensor, and allows for more accurate concentration measurement.

In Experiments 2 and 3 below, trehalose and glucomannan were used as additives in the enzyme layer. Even with those additives, the sensitivity of the biosensor was improved just as when sodium polyacrylate was added, and it was proved that more accurate concentration measurement could be performed.

The experiment results are shown below.

Experiment Result 2: Addition of Trehalose to Enzyme Layer

Figure 46:
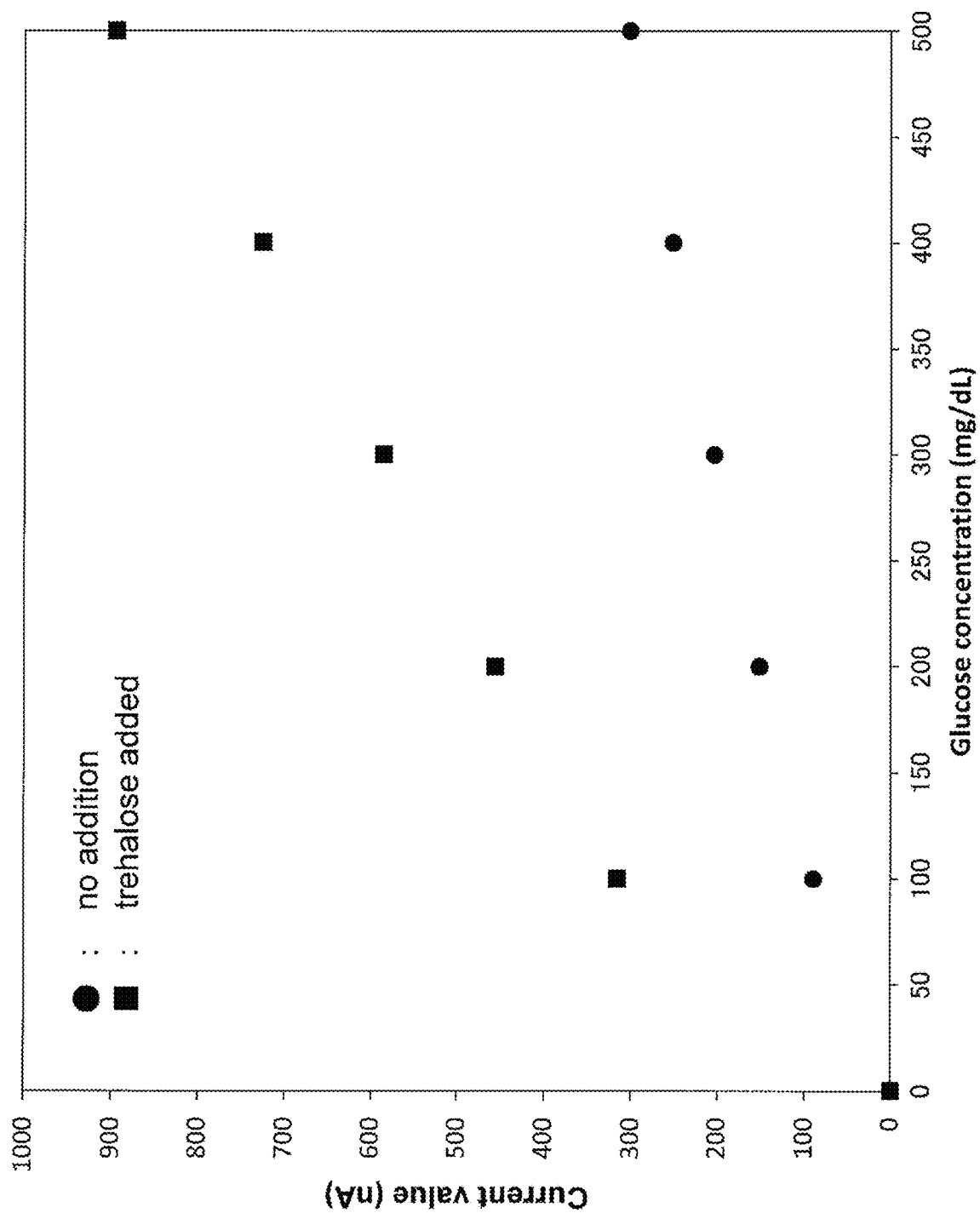
FIG. 46 is a diagram of an experiment result 2.

FIG. 46 shows the result of examining the change in the response current flowing to the sensor when the glucose concentration is varied in order to confirm how well the measurement sensitivity of the biosensor was improved in this embodiment.

In the experiment, a working electrode in which trehalose was added and fixed to an enzyme (as an enzyme layer), a silver/silver chloride electrode (as a reference electrode), and a counter electrode were immersed in physiological saline, the glucose concentration contained in the physiological saline was measured at an application potential of 1.1 V (versus the silver/silver chloride), and the relation between the glucose concentration and the response current was evaluated.

Batch amperometry was used to measure the response current.

Glucose was added to a phosphate buffer solution in amounts of 100 mg/dL, 200 mg/dL, 300 mg/dL, 400 mg/dL, and 500 mg/dL, and the current value 10 minutes after the addition was taken as the measurement value.

As a comparative example, the same experiment was conducted using a sensor in which nothing was added to the enzyme layer.

The measured current value (nA) was plotted on the Y axis, and the glucose concentration (mg/dL) was plotted on the X axis, the result being that the response of the glucose sensor was about three times better with the sensor in which trehalose was added in an amount of 0.001%.

This proves that adding trehalose to the enzyme layer improves the sensitivity of the biosensor, and allows for more accurate concentration measurement.

Experiment Result 3: Addition of Glucomannan to Enzyme Layer

Figure 47:
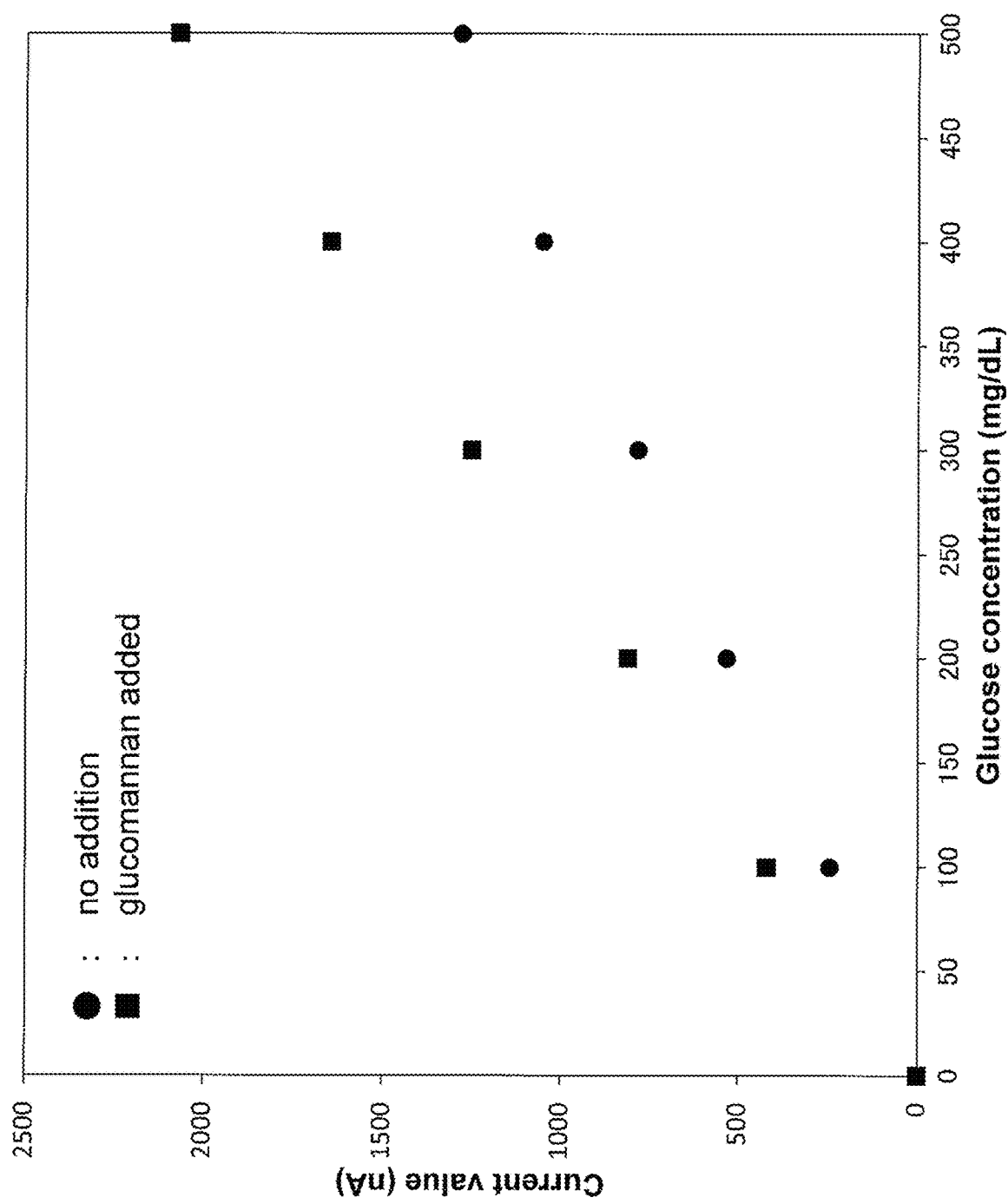
FIG. 47 is a diagram of an experiment result 3.

FIG. 47 shows the result of examining the change in the response current flowing to the sensor when the glucose concentration is varied in order to confirm how well the measurement sensitivity of the biosensor was improved in this embodiment.

In the experiment, a working electrode in which glucomannan was added and fixed to an enzyme (as an enzyme layer), a silver/silver chloride electrode (as a reference electrode), and a counter electrode were immersed in physiological saline, the glucose concentration contained in the physiological saline was measured at an application potential of 1.1 V (versus the silver/silver chloride), and the relation between the glucose concentration and the response current was evaluated.

Batch amperometry was used to measure the response current.

Glucose was added to a phosphate buffer solution in amounts of 100 mg/dL, 200 mg/dL, 300 mg/dL, 400 mg/dL, and 500 mg/dL, and the current value 10 minutes after the addition was taken as the measurement value.

As a comparative example, the same experiment was conducted using a sensor in which nothing was added to the enzyme layer.

The measured current value (nA) was plotted on the Y axis, and the glucose concentration (mg/dL) was plotted on the X axis, the result being that the response of the glucose sensor was about three times better with the sensor in which glucomannan was added in an amount of 0.001%.

This proves that adding glucomannan to the enzyme layer improves the sensitivity of the biosensor, and allows for more accurate concentration measurement.

Supplemental Note

The present invention encompasses not only to the sensor insertion device and biosensor described above, but also the sensor supply unit, container, biosensor, wearable unit, sensor attachment device, sensor insertion device, sensor supply unit discussed below.

The sensor supply unit pertaining to the first invention is a sensor supply unit supplied in a state of being housed in a container, comprising:

a sensor main body;

a sensor support that supports the sensor main body;

a needle that is detachably inserted into the sensor main body;

a needle support that fixes and supports the needle and detachably supports the sensor support; and a support body that slidably supports the needle support, wherein the support body has an engagement component that engages with the container in which it is housed.

The sensor supply unit pertaining to the second invention is the sensor supply unit pertaining to the first invention, wherein the support body has a base component and a head that is provided above the base component, and the engagement component is provided to the upper face of the base component.

The sensor supply unit pertaining to the third invention is the sensor supply unit pertaining to the first invention, wherein the support body has a truncated cone-shaped base component and a cylindrical head that is provided above the base component.

The sensor supply unit pertaining to the fourth invention is the sensor supply unit pertaining to the first invention, wherein the support body has a truncated cone-shaped base component and a cylindrical head that is provided above the base component, and the radius of a circle on the upper face of the base component is larger than the radius of a circle on the lower face of the head.

The sensor supply unit pertaining to the fifth invention is the sensor supply unit pertaining to any of the second to fourth inventions, wherein the engagement component is provided to the upper face of the base component of the support body.

The sensor supply unit pertaining to the sixth invention is the sensor supply unit pertaining to any of the first to fifth inventions, wherein the sensor main body is a biosensor for electrochemically measuring glucose.

The sensor supply unit pertaining to the seventh invention is the sensor supply unit pertaining to any of the first to sixth inventions, wherein the sensor main body has a rod-like measurement component and a substrate-shaped contact that is linked to the rod-like measurement component.

The sensor supply unit pertaining to the eighth invention is the sensor supply unit pertaining to any of the first to seventh inventions, wherein the sensor support has an electrode that connects electric signals from the sensor main body.

The sensor supply unit pertaining to the ninth invention is the sensor supply unit pertaining to any of the first to eighth inventions, wherein the needle opens in the longitudinal direction.

The sensor supply unit pertaining to the tenth invention is the sensor supply unit pertaining to any of the first to ninth inventions, wherein the needle support has a rod shape and has a holder that supports the needle at a first end portion and supports the sensor support projecting laterally from the first end.

The sensor supply unit pertaining to the eleventh invention is the sensor supply unit pertaining to the seventh invention, wherein the sensor support has a first container for inserting the contact of the sensor main body, and a connector for sandwiching the contact of the sensor main body provided in the first container.

The container pertaining to the twelfth invention is a container that houses a sensor supply unit having an opening at its upper part, the container comprising:

an engagement component that detachably engages with the sensor supply unit provided on the inner bottom face of the container;

an opening component that is provided above the engagement component and opens up the engagement component; and legs that support the opening component and the engagement component with respect to the inner bottom face.

The container pertaining to the thirteenth invention is the container pertaining to the twelfth invention, wherein the opening portion is provided at a position opened toward the outer peripheral edge of the engagement component.

The container pertaining to the fourteenth invention is the container pertaining to the twelfth or thirteenth invention, wherein the opening portion and the engagement component are connected via an inclined face that is inclined inward from the outside of the container.

The sensor supply unit pertaining to the fifteenth invention comprises:

a sensor main body;

a sensor support that supports the sensor main body;

a needle that is detachably inserted into the sensor main body;

a needle support that fixes and supports the needle and detachably supports the sensor support; and a support body that slidably supports the needle support, wherein the support body has a grip portion that is gripped when the support body is taken out.

The sensor supply unit pertaining to the sixteenth invention is the sensor supply unit pertaining to the fifteenth invention, wherein the support body has a base component and a head that is provided above the base component.

The sensor supply unit pertaining to the seventeenth invention is the sensor supply unit pertaining to the fifteenth invention, wherein the support body has a truncated cone-shaped base component and a cylindrical head that is provided above the base component.

The sensor supply unit pertaining to the eighteenth invention is the sensor supply unit pertaining to the fifteenth invention, wherein the support body has a truncated cone-shaped base component and a cylindrical head that is provided above the base component, and the radius of a circle on the upper face of the base component is larger than the radius of a circle on the lower face of the head.

The sensor supply unit pertaining to the nineteenth invention is the sensor supply unit pertaining to any of the fifteenth to eighteenth inventions, wherein the grip portion is provided to the head of the support body.

The sensor supply unit pertaining to the twentieth invention is the sensor supply unit pertaining to any of the fifteenth to nineteenth inventions, wherein the sensor main body is a biosensor that electrochemically measures glucose.

The sensor supply unit pertaining to the twenty-first invention is the sensor supply unit pertaining to any of the fifteenth to twentieth inventions, wherein the sensor main body has a rod-like measurement component and a substrate-shaped contact that is linked to the measurement component.

The sensor supply unit pertaining to the twenty-second invention is the sensor supply unit pertaining to any of the fifteenth to twenty-first inventions, wherein the sensor support has a connection terminal for connecting electric signals from the sensor main body.

The sensor supply unit pertaining to the twenty-third invention is the sensor supply unit pertaining to any of the fifteenth to twenty-second inventions, wherein the needle opens in the longitudinal direction.

The sensor supply unit pertaining to the twenty-fourth invention is the sensor supply unit pertaining to any of the fifteenth to twenty-third inventions, wherein the needle support has a rod shape and has a holder that supports the needle at a first end portion and supports the sensor support projecting laterally from the first end portion.

The sensor supply unit pertaining to the twenty-fifth invention is the sensor supply unit pertaining to the twenty-first invention, wherein the sensor support has a first container for inserting the contact of the sensor main body, and a connector for sandwiching onto the contact of the sensor main body provided in the first container.

The biosensor pertaining to the twenty-sixth invention comprises:

a sensor main body that senses biological information and converts it into electric signals; and a sensor support that supports the sensor main body and to which electric signals from the sensor main body are inputted, wherein the sensor main body has a measurement component that is inserted into an organism, and a substrate-shaped contact that is fixed and connected to the measurement component, and the sensor support has a first container into which the contact of the sensor main body is inserted, and a connector that sandwiches the contact of the sensor main body provided in the first container.

The biosensor pertaining to the twenty-seventh invention is the biosensor pertaining to the twenty-sixth invention, wherein the sensor main body is a biosensor that is inserted into an organism and electrochemically measures glucose.

The biosensor pertaining to the twenty-eighth invention is the biosensor pertaining to the twenty-sixth or twenty-seventh invention, wherein the sensor support has a connection terminal that connects electric signals from the sensor main body.

The biosensor pertaining to the twenty-ninth invention comprises:

a sensor main body that senses biological information and converts it into electric signals; and a sensor support that supports the sensor main body and to which electric signals from the sensor main body are inputted, wherein the sensor main body has a measurement component that is inserted into an organism, and a substrate-like contact that is connected to the measurement component, and the sensor support has a cylindrical first container into which the contact of the sensor main body is inserted, a connector that is provided in the first container to sandwich the contact portion of the sensor main body, and a cylindrical second container that covers the first container.

The biosensor pertaining to the thirtieth invention is the biosensor pertaining to the twenty-ninth invention, wherein ribs are formed on the side face of the first container that comes into contact with the second container.

The biosensor pertaining to the thirty-first invention is the biosensor pertaining to the twenty-ninth or thirtieth invention, wherein the first container is made of a softer material than the second container.

The biosensor pertaining to the thirty-second invention is the biosensor pertaining to any of the twenty-ninth to thirty-first inventions, wherein the sensor main body is a biosensor that is inserted into an organism and electrochemically measures glucose.

The biosensor pertaining to the thirty-third invention is the biosensor pertaining to any of the twenty-ninth to thirty-second inventions, wherein the sensor support has a connection terminal that connects electric signals from the sensor main body.

The biosensor pertaining to the thirty-fourth invention is the biosensor pertaining to any of the twenty-ninth to thirty-third inventions, wherein the portion of the sensor main body other than the contact is covered with a nonconductive material.

The wearable unit pertaining to the thirty-fifth invention comprises:

a substantially circular main body;

an outer bottom face that is coated with an adhesive to allow attachment to a patient's body;

a through-hole into which a sensor unit to be inserted into the patient's body is inserted; and a mating groove that grips a transmitter provided to the peripheral edge of the main body.

The wearable unit pertaining to the thirty-sixth invention is the wearable unit pertaining to the thirty-fifth invention, wherein the wearable unit is molded from an elastomer resin.

The wearable unit pertaining to the thirty-seventh invention is the wearable unit pertaining to the thirty-fifth or thirty-sixth invention, wherein the through-hole is provided at a position away from the center of the circular shape.

The sensor attachment device pertaining to the thirty-eighth invention comprises, in a detachable state:

a wearable unit that is worn on a patient's body;

a sensor unit that includes a sensor main body that is less in the patient's body; and a transmitter that calculates biological information from a signal inputted from the sensor unit, and stores this information.

The sensor attachment device pertaining to the thirty-ninth invention is the sensor attachment device pertaining to the thirty-eighth invention, further comprising a substantially circular wearable unit having:

an outer bottom face that is coated with an adhesive to allow attachment to a patient's body;

a through-hole into which the sensor unit to be inserted into the patient's body is inserted; and a convex groove that grips a transmitter provided to the peripheral edge.

The sensor attachment device pertaining to the fortieth invention is the sensor attachment device pertaining to the thirty-eighth or thirty-ninth invention, wherein the wearable unit is molded from an elastomer resin.

The sensor attachment device pertaining to the forty-first invention is the sensor attachment device pertaining to any of the thirty-eighth to fortieth inventions, wherein the transmitter has a substantially circular shape and has a convex wearable unit mating component at a position away from the center position of the lower face, and the wearable unit has a concave mounting hole that mates with the wearable unit mating component of the transmitter.

The sensor attachment device pertaining to the forty-second invention is the sensor attachment device pertaining to any of the thirty-eighth to forty-first inventions, wherein the wearable unit has a first arrow provided at a visible location, and a second arrow that matches the direction of the first arrow is provided on the upper face of the transmitter.

The sensor attachment device pertaining to the forty-third invention is the sensor attachment device pertaining to any of the thirty-eighth to forty-second inventions, wherein a concave groove is provided to the peripheral edge of the lower side face of the transmitter, and a convex part that mates with the concave groove is provided to the peripheral edge of the wearable unit.

The sensor attachment device pertaining to the forty-fourth invention is the sensor attachment device pertaining to the thirty-ninth invention, wherein the through-hole into which the sensor unit is inserted is provided at a position away from the center of the substantially circular shape.

The sensor insertion device pertaining to the forty-fifth invention is a sensor insertion device that takes out a sensor supply unit in a state of supporting a sensor from a container, and inserts the sensor supported by the sensor supply unit into a patient's body, comprising:

a main body case; and a sensor supply unit grip portion that is provided below the main body case and grips the sensor supply unit, wherein the sensor supply unit grip portion has a sensor supply unit insertion portion having an opening underneath.

The sensor insertion device pertaining to the forty-sixth invention is the sensor insertion device pertaining to the forty-fifth invention, wherein the inside diameter of the opening portion of the sensor supply unit insertion portion is substantially the same as the outside diameter of the grip portion of the sensor supply unit, the outside diameter of the lower face of the sensor supply unit insertion portion is shorter than the length between a pair of opening prongs provided to the container and longer than the length between engagement prongs, and the length of the sensor supply unit insertion portion in the longitudinal direction is greater than the length of the grip portion of the sensor supply unit.

The sensor supply unit pertaining to the forty-seventh invention is the sensor supply unit pertaining to the forty-fifth or forty-sixth invention, comprising:

a rod-like sensor main body;

a sensor support that supports the sensor main body;

a needle that detachably inserts the sensor main body;

a needle support that fixes and supports the needle and detachably supports the sensor support; and a support body that supports the needle support, wherein the support body has a grip portion that is gripped when the support body is taken out.

The container pertaining to the forty-eighth invention is a container that houses the sensor supply unit pertaining to the forty-fifth invention, which has an opening at the top and comprises:

a mounting face that is provided to the inner bottom face and detachably supports a sensor supply unit;

an engagement prong that detachably engages with the sensor supply unit;

an opening prong that is provided above the engagement prong and disengages the engagement prong; and legs that support the opening prong and the engagement prong with respect to the inner bottom face.

The sensor insertion device pertaining to the forty-ninth invention comprises:

a main body case;

a needle slider that is provided in the main body case, grips a sensor at the front end, and is provided slidably in the direction in which the sensor is inserted into a patient's body;

a disposal slider that biases the needle slider in the opposite direction from the sensor insertion direction; and a puncture knob that hits the rear end of the needle slider to push the needle slider in the sensor insertion direction, wherein the puncture knob is provided with a detector that detects that the needle slider has slid forward by a specific distance in order to insert the sensor into the patient's body, and a controller that opens up the contact portion of the rear end of the needle slider according to the status of the detector.

The sensor insertion device pertaining to the fiftieth invention is the sensor insertion device pertaining to the forty-ninth invention, wherein the detector detects that the front end of the puncture knob has hit the rear end of the disposal slider.

The sensor insertion device pertaining to the fifty-first invention is the sensor insertion device pertaining to the forty-ninth or fiftieth invention, wherein the opening mechanism has an insertion hole in which the rear end portion of the needle slider is inserted, a lid of the insertion hole, and an opening/closing component that opens and closes the lid by detecting that the front end of the puncture knob has hit the rear end of the disposal slider.

The sensor insertion device pertaining to the fifty-second invention is the sensor insertion device pertaining to any of the forty-ninth to fifty-first inventions, wherein the device is used as an auxiliary device for a continuous glucose monitoring (CGM) device that leaves a sensor in a patient's body, and after the sensor has been inserted into the patient's body along with the needle gripped by the needle slider, just the needle is pulled out.

The sensor insertion device pertaining to the fifty-third invention comprises:

a main body case;

a needle slider that is provided in the main body case, grips a sensor at the front end, and is provided slidably in the direction in which the sensor is inserted into a patient's body;

a disposal slider that biases the needle slider in the opposite direction from the sensor insertion direction; and a puncture knob having an opening mechanism that opens up the contact portion of the rear end of the needle slider by hitting the rear end of the needle slider to push in the needle slider in the sensor insertion direction, and detecting that it has hit the rear end of the disposal slider, wherein the opening mechanism of the puncture knob has an insertion hole into which the rear end portion of the needle slider is inserted, a window body that slides to open and close the opening of the insertion hole, an elastic body that biases the window body in the closing direction, and a handle that slides in contact with the end of the disposal slider and slides the window body in the direction of opening.

The sensor insertion device pertaining to the fifty-fourth invention is the sensor insertion device pertaining to the fifty-third invention, wherein the device is used as an auxiliary device for a continuous glucose monitoring (CGM) device that leaves a sensor in a patient's body, and after the sensor has been inserted into the patient's body along with the needle gripped by the needle slider, just the needle is pulled out.

The sensor insertion device according to the fifty-fifth invention comprises:

a main body case;

a needle slider that is provided in the main body case, grips a sensor at the front end, and slides the needle in the direction in which the sensor is inserted into a patient's body;

a disposal slider that biases the needle slider in the opposite direction from the sensor insertion direction; and a puncture knob having an opening mechanism that opens up the contact portion of the rear end of the needle slider by hitting the rear end of the needle slider to push in the needle slider in the sensor insertion direction, and detecting that it has hit the rear end of the disposal slider, wherein the opening mechanism of the puncture knob has an insertion hole into which the rear end portion of the needle slider is inserted, a window body that rotates the opening of the insertion hole to open and close it, an elastic body that biases the window body in the closing direction, and a handle that slides in contact with the end of the disposal slider and rotates the window body in the direction of opening.

The sensor insertion device pertaining to the fifty-sixth invention is the sensor insertion device pertaining to the fifty-fourth invention, wherein the device is used as an auxiliary device for a continuous glucose monitoring (CGM) device that leaves a sensor in a patient's body, and after the sensor has been inserted into the patient's body along with the needle gripped by the needle slider, just the needle is pulled out.

The sensor insertion device according to the fifty-seventh invention comprises:

a main body case;

a sensor supply unit grip portion that is provided in front of the main body case and grips the sensor supply unit;

a needle slider that is provided in the main body case, grips the sensor supply unit inserted at the front end, and slides in the direction in which the sensor in the sensor supply unit is inserted into a patient's body;

a disposal slider that biases the needle slider in the opposite direction from the direction of insertion of the sensor and hits the sensor supply unit inserted at the front end; and a puncture knob that hits the rear end of the needle slider to push in the needle slider in the sensor insertion direction, wherein, in a state in which the sensor supply unit has been inserted into the sensor supply unit grip portion, the disposal slider slides rearward.

The sensor insertion device pertaining to the fifty-eighth invention is the sensor insertion device pertaining to the fifty-seventh invention, wherein, in a state where the sensor supply unit has been inserted into the sensor supply unit grip portion, the distance that the disposal slider slides rearward is longer than the distance that the needle slider slides rearward.

The sensor insertion device pertaining to the fifty-ninth invention is the sensor insertion device pertaining to the fifty-seventh or fifty-eighth invention, wherein, in a state in which the sensor supply unit has been inserted into the sensor supply unit grip portion, the grip portion of the sensor supply unit is inserted into the front end opening of the needle slider in a state in which the rear end of the needle slider is in contact with the front end of the puncture knob.

The sensor insertion device pertaining to the sixtieth invention is the sensor insertion device pertaining to any of the fifty-seventh to fifty-ninth inventions, the device is used as an auxiliary device for a continuous glucose monitoring (CGM) device that leaves a sensor in a patient's body, and after the sensor has been inserted into the patient's body along with the needle gripped by the needle slider, just the needle is pulled out.

The sensor insertion device pertaining to the sixty-first invention comprises:

a main body case;

a needle slider that is provided in the main body case and is provided slidably in the direction in which a sensor gripped at the front end is inserted into a patient's body;

a puncture knob that hits the rear end of the needle slider to push in the needle slider in the sensor insertion direction; and a load mechanism that requires a specific load from the pushing start position of the puncture knob until it starts to move forward.

The sensor insertion device pertaining to the sixty-second invention is the sensor insertion device pertaining to the sixty-first invention, wherein the puncture knob has a slider that slides within the main body case, and the load mechanism causes an elastic body to hit the slider.

The sensor insertion device pertaining to the sixty-third invention is the sensor insertion device pertaining to the sixty-first invention, wherein the puncture knob has a slider that slides within the main body case, and a plunger that sandwiches the side faces of the slider from both sides, and the load mechanism causes the movable distal end of the plunger to hit the side face of the slider.

The sensor insertion device pertaining to the sixty-fourth invention is the sensor insertion device pertaining to the sixty-first invention, wherein the puncture knob has a slider that slides within the main body case, and a plunger that sandwiches the side faces of the slider from both sides, and the load mechanism has a recess that is provided to the side face of the slider touching the movable distal end of the plunger at the insertion start position of the sensor.

The sensor insertion device pertaining to the sixty-fifth invention is the sensor insertion device pertaining to the sixty-first invention, wherein the puncture knob has a slider that slides within the main body case, and a plunger that sandwiches the side faces of the slider from both sides, and an inclined face that is inclined rearward from the position where the movable distal end of the plunger comes into contact with the side face of the slider is provided at the insertion start position of the sensor.

The sensor supply unit pertaining to the sixty-sixth invention comprises:

a sensor main body;

a sensor support that supports the sensor main body;

a needle that detachably inserts the sensor main body;

a needle support that fixes and supports the needle and detachably supports the sensor support; and a support body that slidably supports the needle support, wherein the support body has a grip portion that is provided on a first end side and grips the support body, and an opening that is provided on a second end side on the opposite side from the first end, for allowing the needle to stick out.

The sensor supply unit pertaining to the sixty-seventh invention is the sensor supply unit pertaining to the sixty-sixth invention, wherein the support body has a base component and a head that is provided on the first end side of the base component, and the opening is provided on the second end side of the base component.

The sensor supply unit pertaining to the sixty-eighth invention is the sensor supply unit pertaining to the sixty-sixth or sixty-seventh invention, wherein the support body has a base component and a head that is provided on the first end side of the base component, and the grip portion is provided on the first end side of the head.

The sensor supply unit pertaining to the sixty-ninth invention is the sensor insertion device pertaining to any of the sixty-sixth to sixty-eighth inventions, wherein the support body has a truncated cone-shaped base component and a cylindrical head that is provided on the first end side of the base component.

The sensor supply unit pertaining to the seventieth invention is the sensor insertion device pertaining to any of the sixty-sixth to sixty-ninth inventions, wherein the inside diameter of the opening is less than the length of the needle.

The sensor supply unit pertaining to the seventy-first invention comprises:

a sensor main body;

a sensor support that supports the sensor main body;

a needle that detachably inserts the sensor main body;

a needle support that fixes and supports the needle and detachably supports the sensor support; and a support body that slidably supports the needle support.

The sensor supply unit pertaining to the seventy-second invention is the sensor insertion device pertaining to the seventy-first invention, wherein the support body has a base component, a head that is provided on a first end side of the base component, and an engagement component that is provided to the upper face of the base component.

The sensor supply unit pertaining to the seventy-third invention is the sensor insertion device pertaining to the seventy-first invention, wherein the support body has a truncated cone-shaped base component and a cylindrical head that is provided on a first end side of the base component.

The sensor supply unit pertaining to the seventy-fourth invention is the sensor insertion device pertaining to the seventy-first invention, wherein the support body has a truncated cone-shaped base component and a cylindrical head that is provided on a first end side of the base component, and the radius of a circle on the upper face of the base component is larger than the radius of a circle on the lower face of the head.

The sensor supply unit pertaining to the seventy-fifth invention is the sensor insertion device pertaining to the seventy-second invention, wherein the engagement component is provided to the upper face of the base component.

The sensor supply unit pertaining to the seventy-sixth invention is the sensor insertion device pertaining to any of the seventy-first to seventy-fifth inventions, wherein the sensor main body is a biosensor that electrochemically measures glucose.

The sensor supply unit pertaining to the seventy-seventh invention is the sensor insertion device pertaining to any of the seventy-first to seventy-sixth inventions, wherein the sensor main body has a rod-like measurement component and a substrate-shaped contact that is connected to the rod-like measurement component.

The sensor supply unit pertaining to the seventy-eighth invention is the sensor insertion device pertaining to any of the seventy-first to seventy-seventh inventions, wherein the sensor support has a connection terminal that connects electric signals from the sensor main body.

The sensor supply unit pertaining to the seventy-ninth invention is the sensor insertion device pertaining to any of the seventy-first to seventy-eighth inventions, wherein the needle opens in the longitudinal direction.

The sensor supply unit pertaining to the eightieth invention is the sensor insertion device pertaining to any of the seventy-first to seventy-ninth inventions, wherein the needle support has a rod shape and has a holder that supports the needle on the second end side and supports the sensor support projecting laterally from the second end.

The sensor supply unit pertaining to the eight-first invention is the sensor insertion device pertaining to the seventy-seventh invention, wherein the sensor support has a first container into which the contact of the sensor main body is inserted, and a connector that is provided in the first container and sandwiches the contact of the sensor main body.

The sensor supply unit pertaining to the eighty-second invention comprises:

a sensor;
a needle that detachably inserts the sensor; and
a support body that slidably supports the needle.

INDUSTRIAL APPLICABILITY

The sensor insertion device of the present invention is expected to find application to blood glucose level sensors in continuous glucose monitoring systems, for example.

REFERENCE SIGNS LIST 1 sensor attachment device
2 upper arm
3 measurement device
4 sensor
5 base unit (wearable unit)
6 sensor unit
7 transmitter
8 through-hole
9 mounting hole
9a concave groove
10 convex part
11 mating component
12 mating component
13 concave groove
13a arrow
14 convex part
14a arrow
15 first container
16 second container
16 a sensor support body (sensor support)
17 opening
18 sensor main body (biosensor)
19a, 19b. 19c terminal
20 rib
21 connector
21a, 21b, 21c terminal
22 lid
23 first end
24 second end
25 contact
26 opening
27 opening
28 nonconductive material
29 container
30 sensor supply unit
31 support body
31a base component
31b head
32 opening
32a, 32b engagement groove
33 needle unit
33a. 33b engagement blade
34 grip portion
35 needle
36 sensor unit support
38a, 38b engagement component
39a, 39b engagement component
40 support
41a, 41b leg
42a, 42b engagement prong
43a, 43b opening prong
44 sensor unit insertion device (sensor insertion device)
45 main body case
46 puncture knob
47 disposal knob
48 sensor supply unit grip portion
49 insertion component
50 slider
52 needle slider
52a latching portion
52b opposing face (first opposing face)
53 disposal slider
53a engagement component
53b opposing face (second opposing face)
55 front end
56a. 56b plunger
57a, 57b movable distal end
58a, 58b recess
59a, 59b inclined face
60 insertion hole
61 window body (opening mechanism)
62 elastic body (return mechanism)
63 handle (opening mechanism)
65 window body (opening mechanism)
66 elastic body (return mechanism)
67 handle (opening mechanism)
68 spring (biasing member)
68a first end
68b second end
70 engagement component
71 engagement component
80 sensor insertion component
81 sensor connector
82 protective film
83 reference electrode connection terminal
84 working electrode connecting terminal
85 counter electrode connection terminal
86 resist film
87 substrate
88 gold electrode
89 reference electrode conductor 90 working electrode conductor
91 reference electrode forming region
92 working electrode
93 reference electrode
94 counter electrode
95 mediator layer
96 enzyme layer

The invention claimed is:

1. A sensor insertion device that uses a needle for puncturing a skin on a first end side to insert a sensor into a patient's body, the sensor insertion device comprising:
   a main body case;
   a needle slider configured to grip the needle and the sensor on the first end side, the needle slider provided inside the main body case in a state of being able to slide in a sensor insertion direction of the sensor;
   a disposal slider that is provided inside the main body case in a state of being able to slide in parallel with the needle slider;
   a biasing member that is provided between the needle slider and the disposal slider, the biasing member configured to bias the needle slider which has moved in the sensor insertion direction in an opposite direction from the sensor insertion direction;
   a puncture knob configured to push the needle slider to a specific puncture position by sliding the needle slider in the sensor insertion direction in a state of being in contact with a second end side of the needle slider that is on an opposite side from the first end side, the puncture knob having an insertion hole into which a rear end portion of the needle slider can be inserted; and
   an opening mechanism configured to put the insertion hole in a closed state when the needle slider is slid a specific length in the sensor insertion direction, and put the insertion hole in an open state in which the second end side of the needle slider has been inserted into the insertion hole by opening up a contact portion between the puncture knob and the second end side of the needle slider when a puncture operation is complete.

2. The sensor insertion device according to claim 1, wherein the opening mechanism has a window body configured to put an opening side of the insertion hole into the closed state so that the rear end portion of the needle slider will not be inserted into the insertion hole, and a handle configured to move the window body in a direction of opening the insertion hole by contacting a part of the disposal slider.

3. The sensor insertion device according to claim 2, wherein the opening mechanism is configured to slide the window body, which is configured to open and close the opening side of the insertion hole, in a direction in which the opening side of the insertion hole opens, by means of the handle that is in sliding contact with the end of the disposal slider.

4. The sensor insertion device according to claim 2, wherein the opening mechanism is configured to rotate the window body, that is configured to open and close the opening side of the insertion hole, in a direction in which the opening side of the insertion hole opens, by means of the handle that is in sliding contact with the end of the disposal slider.

5. The sensor insertion device according to claim 1, further comprising a return mechanism configured to return the open state of the insertion hole produced by the opening mechanism to the closed state after the puncture knob has been pushed in to the specific puncture position and the puncture operation of the needle slider is complete.

6. The sensor insertion device according to claim 5, wherein the second end of the needle slider is held inside the insertion hole of the puncture knob from when the puncture operation is completed until the return mechanism returns the insertion hole to the closed state.

7. The sensor insertion device according to claim 5, wherein the return mechanism includes an elastic configured to bias a part of the opening mechanism in a direction in which the insertion hole is closed.

8. The sensor insertion device according to claim 1, wherein a length (L1) over which the puncture knob slides in the sensor insertion direction is shorter than a length (L2) over which the needle slider is inserted into the insertion hole of the puncture knob.

9. The sensor insertion device according to claim 1, further comprising:
   a sensor supply unit that is configured to mount to the needle slider and supply a sensor to the first end side of the needle slider,
   wherein, a length over which the disposal slider slides in the opposite direction from the sensor insertion direction to the opposite side from the first end side is longer than a length over which the needle slider slides to the opposite side from the first end side during mounting of the sensor supply unit.

10. The sensor insertion device according to claim 1, wherein the needle slider has a first opposing face that is opposite the disposal slider,
    the disposal slider has a second opposing face that is opposite the needle slider, and
    the needle slider and the disposal slider slide along the puncture direction in a state in which the first opposing face and the second opposing face are in contact on an inner peripheral face side of the main body case.

11. The sensor insertion device according to claim 1, wherein the needle slider and the disposal slider are configured as a first substantially half-cylindrical member and a second substantially half-cylindrical member.

12. The sensor insertion device according to claim 1, wherein the biasing member is disposed in a space formed in an interior between the needle slider and the disposal slider when the needle slider and the disposable slider are disposed together within the main body case.

13. The sensor insertion device according to claim 12, wherein the biasing member has a first end that is latched to a first latching portion provided on an inner peripheral face side of the needle slider, and a second end that is latched to a second latching portion provided on an inner peripheral face side of the disposal slider.

14. The sensor insertion device according to claim 1, wherein the opening mechanism opens is configured to open up a portion where the puncture knob and the second end of the needle slider are in contact, thereby moving the insertion hole into the open state, when the needle slider slides a specific distance in the puncture direction to the first end side to insert the sensor into a Patient's body.

15. The sensor insertion device according to claim 14, wherein, the opening mechanism is configured to open up the portion where the puncture knob and the second end of the needle slider are in contact when the first end side of the puncture knob hits the second end side of the disposal slider.

16. The sensor insertion device according to claim 1, further comprising
a disposal knob configured to slide the needle slider in the sensor insertion direction during disposal of a component including a needle that has completed puncture.

17. The sensor insertion device according to claim 16, wherein a length (L1) over which the puncture knob slides in the sensor insertion direction is shorter than a length (L2) over which the needle slider is inserted into the insertion hole of the puncture knob, and a length (L5) over which the disposal knob slides in the sensor insertion direction is longer than a difference between the length L2 and the length L1.

18. The sensor insertion device according to claim 1, wherein the disposal slider slides rearward in a state in which the needle and the sensor are gripped.

19. The sensor insertion device according to claim 1, further comprising
a load mechanism configured to require a specific load until the puncture knob starts to move forward from a pushing start position of the puncture knob.

20. The sensor insertion device according to claim 19, wherein the puncture knob has a slider configured to slide within the main body case, and
the load mechanism has an elastic body configured to come into contact with the slider.

21. The sensor insertion device according to claim 19, wherein the puncture knob has a slider configured to slide in the main body case, and plungers configured to pinch side faces of the slider from both sides, and
the load mechanism brings movable distal ends of the plungers into contact with the side faces of the slider.

22. The sensor insertion device according to claim 1, wherein the puncture knob has a slider configured to slide in the main body case, and plungers configured to pinch side faces of the slider from both sides, and has recesses provided on the side faces of the slider touching movable distal ends of the plungers at an insertion start position of the sensor.

23. The sensor insertion device according to claim 1, wherein the puncture knob has a slider that slides in the main body case, and plungers that pinch the side faces of the slider from both sides, and
the side faces of the slider have inclined faces that are inclined rearward from positions touching the movable distal ends of the plungers at an insertion start position of the sensor.

24. The sensor insertion device according to claim 1, wherein only the needle is withdrawn by a biasing force of the biasing member while leaving the sensor in the body after the sensor is inserted into the body together with the needle gripped on the first end side by the needle slider.

* * * * *

UNITED STATES PATENT AND TRADEMARK OFFICE
CERTIFICATE OF CORRECTION

| | |
|---|---|
| PATENT NO. | : 11,369,412 B2 |
| APPLICATION NO. | : 16/094329 |
| DATED | : June 28, 2022 |
| INVENTOR(S) | : Yoshiteru Ii |

It is certified that error appears in the above-identified patent and that said Letters Patent is hereby corrected as shown below:

On the Title Page

Item (72), please delete the following inventors:
"1. Takashi ENDOH
2. Kazuaki EDAGAWA
3. Tetsuya NORIKANE
4. Junko IKEDA"

Signed and Sealed this
Twenty-fourth Day of January, 2023

Katherine Kelly Vidal
*Director of the United States Patent and Trademark Office*